(12) United States Patent
Blancafort

(10) Patent No.: US 10,201,610 B2
(45) Date of Patent: Feb. 12, 2019

(54) INTERFERENCE PEPTIDES AND USE THEREOF

(71) Applicant: The University of Western Australia, Nedlands (AU)

(72) Inventor: Pilar Blancafort, East Fremantle (AU)

(73) Assignee: THE UNIVERSITY OF WESTERN AUSTRALIA, Nedlands, Western Australia (AU)

( * ) Notice: Subject to any disclaimer, the term of this patent is extended or adjusted under 35 U.S.C. 154(b) by 0 days.

(21) Appl. No.: 14/518,632

(22) Filed: Oct. 20, 2014

(65) Prior Publication Data
US 2016/0108100 A1 Apr. 21, 2016

(51) Int. Cl.
| | | |
|---|---|---|
| *C07K 4/00* | (2006.01) | |
| *A61K 38/00* | (2006.01) | |
| *A61K 45/06* | (2006.01) | |
| *C07K 14/82* | (2006.01) | |
| *C07K 14/47* | (2006.01) | |

(52) U.S. Cl.
CPC .......... *A61K 45/06* (2013.01); *C07K 14/4702* (2013.01); *C07K 14/82* (2013.01); *A61K 38/00* (2013.01); *C07K 2319/43* (2013.01)

(58) Field of Classification Search
None
See application file for complete search history.

(56) References Cited

U.S. PATENT DOCUMENTS

| | | | | |
|---|---|---|---|---|
| 6,841,535 B2 * | 1/2005 | Divita | .............. | A61K 47/48246 424/130.1 |
| 2007/0042945 A1 * | 2/2007 | Bodary | .................. | C07K 14/47 536/23.2 |
| 2011/0177557 A1 * | 7/2011 | Edenhofer | ........... | C12N 5/0696 435/69.7 |
| 2014/0147440 A1 * | 5/2014 | Ruiz Altaba | ....... | A61K 31/7105 424/133.1 |

OTHER PUBLICATIONS

Wells, J.A. Additivity of Mutational Effects in Proteins. Biochemistry 29:8509-8517 (1990).*
Ngo et al. Computational Complexity, Protein Structure Prediction and the Levinthal Paradox. The Protein Folding Problem and Tertiary Structure Prediction, pp. 433-440 and 492-495 (1994).*
Tokuriki et al. Stability effects of mutations and protein evolvability; Current Opinion in Structural Biology, 19:596-604 (2009).*
Beltran et al. Novel role of Engrailed 1 as a prosurvival transcription factor in basal-like breast cancer and engineering of interference peptides block its oncogenic function. Oncogene 33, 4767-4777 (2014).*
Georgoulias et al. Docetaxel (Taxotere) in the Treatment of Non-Small Cell Lung Cancer. Current Medicinal Chemistry vol. 9, 869-877 (2002).*
Lawrence et al. Comparison of DX-8951f and toptecan effects on tumor colony formation from freshly explanted adult and pediatric human tumor cells. 1999, Anti-Cancer Drugs 10:655-661 (1999).*
Depenbrock et al. Preclinical activity of trans-indazolium {tetrachlorobisindazoleruthenate (III)] (NSC 666158; IndCR; KP 1019) against tumour colony-forming units and progenitor cells. European Journal of Cancer 33:2404-2410 (1997).*
Kornblith et al. In vitro responses of ovarian cancers to platinums and taxanes. Anticancer Research 23:543-548 (2003).*
Evans, et al. "Multimodal analysis of PEI-mediated endocytosis of nanoparticles in neural cells." ACS nano. Nov. 22, 2011;5(11):8640-8.
Li, et al. "Surface-modified LPD nanoparticles for tumor targeting." Annals of the New York Academy of Sciences. Oct. 2006;1082:1-8.
Banerjee, et al. "Anisamide-targeted stealth liposomes: a potent carrier for targeting doxorubicin to human prostate cancer cells." International journal of cancer Journal international du cancer. Nov. 20, 2004;112(4):693-700.
Sugahara, et al. "Tissue-penetrating delivery of compounds and nanoparticles into tumors." Cancer cell. Dec. 8, 2009;16(6):510-20.
Harrison, et al. "In vivo imaging and biodistribution of multimodal polymeric nanoparticles delivered to the optic nerve." Small. May 21, 2012;8(10):1579-89).
Lara, et al. "Targeting serous epithelial ovarian cancer with designer zinc finger transcription factors." J Biol Chem. Aug. 24, 2012;287(35):29873-86.
Zhou, et al. "ATP-directed capture of bioactive herbal-based medicine on human tRNA synthetase." Nature. Feb. 7, 2013;494(7435):121-4).
Prat, et al., "Phenotypic and molecular characterization of the claudin-low intrinsic subtype of breast cancer", 2010, pp. 1-18, vol. 12, No. R68, Breast Cancer Research.
Beltran, et al., "Generation of tumor-initiating cells by exogenous delivery of OCT4 transcription factor", 2001, pp. 1-21, vol. 12, No. R94, Breast Cancer Research.
Beltran, et al., "Suppression of Breast Tumor Growth and Metastasis by an Engineered Transcription Factor", Sep. 2011, pp. 1-14, vol. 6, issue 6, PLoS One.

* cited by examiner

*Primary Examiner* — Elizabeth C. Kemmerer
*Assistant Examiner* — Regina M DeBerry
(74) *Attorney, Agent, or Firm* — Stephen J. Weyer, Esq.; Stites & Harbison, PLLC

(57) ABSTRACT

A purified and isolated peptide comprises an amino acid sequence of SEQ ID NOs: 1 to 8. A method is also provided for preventing interaction, e.g. binding, of EN1 with EPRS in a cell by introducing, into the cell, a peptide having a sequence of SEQ ID NOs: 1 to 8, which results in the peptide interacting with EPRS thereby preventing an interaction of EPRS with EN1. Apoptosis can be induced in a cell expressing either or both of EN1 and EN2, by introducing into the cell, a peptide of SEQ ID NOs: 1 to 8.

4 Claims, 26 Drawing Sheets
Specification includes a Sequence Listing.

Figure 12

| Gene symbol | Gene Name | p value* |
|---|---|---|
| ADNP | activity-dependent neuroprotector homeobox | p=6.51e$^{-11}$ |
| ALX1 | cartilage paired-class homeoprotein 1 | p=3.77e$^{-05}$ |
| BARX1 | BarH-like homeobox 1 | p=0.0416 |
| BARX2 | BARX homeobox 2 | p=3.62e$^{-04}$ |
| CDX2 | caudal type homeobox 2 | p=0.0467 |
| CDX4 | caudal type homeo box 4 | p=0.00262 |
| CRX | cone-rod homeobox containing gene | p=0.0363 |
| CUX1 | cut-like homeobox 1 | p=1.3e$^{-07}$ |
| CUX2 | cut-like homeobox 2 | p=1.66e$^{-04}$ |
| DLX3 | distal-less homeobox 3 | p=4.18e$^{-05}$ |
| DLX4 | distal-less homeobox 4 | p=3.78e$^{-07}$ |
| DLX5 | distal-less homeobox 5 | p=1.96e$^{-14}$ |
| DLX6 | distal-less homeobox 6 | p=2.79e$^{-08}$ |
| EMX2 | empty spiracles homeobox 2 | p=1.51e$^{-04}$ |
| EN1 | engrailed homeobox 1 | p=4.65e$^{-52}$ |
| EN2 | engrailed homeobox 2 | p=5.67e$^{-06}$ |
| EVX1 | even-skipped homeobox 1 | p=7.42e$^{-05}$ |
| GBX2 | gastrulation brain homeobox 2 | p=5.24e$^{-05}$ |
| GCLC | glutamate-cysteine ligase, catalytic subunit | p=9.33e$^{-04}$ |
| GSC | goosecoid homeobox | p=5.11e$^{-08}$ |
| HESX1 | HESX homeobox 1 | p=2.51e$^{-04}$ |
| HHEX | hematopoietically expressed homeobox | p=1.6e$^{-11}$ |
| HLX | H2.0-like homeobox | p=1.02e$^{-14}$ |
| HNF1A | HNF1 homeobox A | p=1.45e$^{-04}$ |
| HOMEZ | homeobox and leucine zipper encoding | p=4.53e$^{-13}$ |
| HOPX | HOP homeobox | p=1.52e$^{-05}$ |
| HOXA3 | homeobox A3 | p=0.0111 |
| HOXA4 | homeobox A4 | p=1.38e$^{-21}$ |
| HOXA5 | homeobox A5 | p=8.04e$^{-12}$ |
| HOXA7 | homeobox A7 | p=4.04e$^{-12}$ |
| HOXB13 | homeobox B13 | p=0.00288 |
| HOXB2 | homeobox B2 | p=2.54e$^{-23}$ |

Figure 12 (Continued)

| | | |
|---|---|---|
| HOXB3 | homeobox B3 | p=0.0013 |
| HOXB5 | homeobox B5 | p=7.3e$^{-05}$ |
| HOXB6 | homeobox B6 | p=5.4e$^{-07}$ |
| HOXB8 | homeobox B8 | p=0.00194 |
| HOXB9 | homeobox B9 | p=0.00332 |
| HOXC10 | homeobox C10 | p=1.61e$^{-07}$ |
| HOXC11 | homeobox C11 | p=2.41$^{-04}$ |
| HOXC13 | homeobox C13 | p=4.3e$^{-11}$ |
| HOXC8 | homeobox C8 | p=0.00291 |
| HOXC9 | homeobox C9 | p=1.61e$^{-07}$ |
| HOXD1 | homeobox D1 | p=0.00637 |
| HOXD13 | homeobox D13 | p=0.0229 |
| HOXD3 | homeobox D3 | p=0.027 |
| HOXD8 | homeobox D8 | p=3.97e$^{-09}$ |
| HOXD9 | homeobox D9 | p=1.66$^{-04}$ |
| IRX1 | iroquois homeobox 1 | p=1.15e$^{-11}$ |
| IRX2 | iroquois homeobox 2 | p=3.7e$^{-07}$ |
| IRX3 | iroquois homeobox 3 | p=5.97e$^{-16}$ |
| IRX4 | iroquois homeobox 4 | p=1.63e$^{-05}$ |
| IRX5 | iroquois homeobox 5 | p=1.28e$^{-15}$ |
| IRX6 | iroquois homeobox 6 | p=0.0434 |
| LASS2 | LAG1 homolog, ceramide synthase 2 | p=1.25e$^{-23}$ |
| LASS4 | LAG1 homolog, ceramide synthase 4 | p=3.14e$^{-15}$ |
| LBX1 | LIM homeobox 1 | p=0.00544 |
| LHX1 | LIM homeobox 1 | p=0.00542 |
| LHX2 | LIM homeobox 2 | p=4.65e$^{-08}$ |
| LHX6 | LIM homeobox 6 | p=6.08e$^{-10}$ |
| LMX1A | LIM homeobox transcription factor 1, alpha | p=0.0216 |
| MEIS1 | Meis homeobox 1 | p=0.0129 |
| MEIS2 | Meis homeobox 2 | p=5.43e$^{-11}$ |
| MEIS3 | Meis homeobox 3; Meis homeobox 3 pseudogene 2 | p=3.41e$^{-04}$ |
| MEOX1 | mesenchyme homeobox 1 | p=1.39e$^{-09}$ |
| MEOX2 | mesenchyme homeobox 2 | p=5.18e$^{-09}$ |
| MIXL1 | Mix1 homeobox-like 1 (Xenopus laevis) | p=0.0368 |
| MNX1 | motor neuron and pancreas homeobox 1 | p=0.1 |
| MSX2 | msh homeobox 2 | p=2.04e$^{-09}$ |
| NANOG | Nanog homeobox pseudogene 8; Nanog | p=0.0055 |

Figure 12 (Continued)

| | homeobox | |
|---|---|---|
| NKX2.3 | NK2 homeobox 3 | p=0.00476 |
| NKX2.5 | NK2 homeobox 5 | p=5.94e$^{-08}$ |
| NKX3.1 | NK3 homeobox 1 | p=0.00374 |
| NKX6.1 | NK6 homeobox 1 | p=0.0353 |
| ONECUT2 | one cut homeobox 2 | p=9.76e$^{-05}$ |
| OTP | orthopedia homeobox | p=0.00464 |
| OTX1 | orthodenticle homeobox 1 | p=7.85e$^{-05}$ |
| OTX2 | orthodenticle homeobox 2 | p=0.0561 |
| PBX1 | pre-B-cell leukemia homeobox 1 | p=6.32e$^{-23}$ |
| PBX3 | pre-B-cell leukemia homeobox 3 | p=4.42e$^{-07}$ |
| PBX4 | pre-B-cell leukemia homeobox 4 | p=3.39e$^{-13}$ |
| PHOX2A | paired-like homeobox 2a | p=3.62e$^{-3}$ |
| PHOX2B | paired-like homeobox 2b | p=1.56e$^{-04}$ |
| PHTF1 | putative homeodomain transcription factor 1 | p=1.18e$^{-08}$ |
| PITX1 | paired-like homeodomain 1 | p=1.06e$^{-04}$ |
| PITX3 | paired-like homeodomain 3 | p=3.18e$^{-05}$ |
| PKNOX2 | Pbx/knotted 1 homeobox 2 | p=0.0233 |
| POU2F1 | POU class 2 homeobox 1 | p=0.00603 |
| POU2F2 | POU class 2 homeobox 2 | p=2.02e$^{-07}$ |
| POU3F2 | POU class 3 homeobox 2 | p=3.53e$^{-06}$ |
| POU3F4 | POU class 3 homeobox 4 | p=7.78e$^{-04}$ |
| POU4F1 | POU class 4 homeobox 1 | p=2.19e$^{-09}$ |
| POU5F1 | POU class 5 homeobox 1 | p=9.64e$^{-12}$ |
| PROP1 | PROP paired-like homeobox 1 | p=5.42e$^{-16}$ |
| PROX1 | prospero homeobox 1 | 1.73e$^{-08}$ |
| PRRX1 | paired related homeobox 1 | p=1.12e$^{-06}$ |
| PRRX2 | paired related homeobox 2 | p=0.00114 |
| RAX | retina and anterior neural fold homeobox | p=0.00368 |
| RHOXF1 | Rhox homeobox family, member 1 | p=6.03e$^{-09}$ |
| SATB1 | SATB homeobox 1 | p=4.79e$^{-16}$ |
| SHOX | short stature homeobox | p=0.00296 |
| SHOX2 | short stature homeobox 2 | p=7.17e$^{-09}$ |
| SIX1 | SIX homeobox 1 | p=9.78e$^{-07}$ |
| SIX3 | SIX homeobox 3 | p=2.5e$^{-05}$ |
| SIX4 | SIX homeobox 4 | p=7.88e$^{-05}$ |
| SIX6 | SIX homeobox 6 | p=.66e$^{-04}$ |

Figure 12 (Continued)

| TGIF1 | TGFB-induced factor homeobox 1 | p=4.47e$^{-08}$ |
|---|---|---|
| TGIF2 | TGFB-induced factor homeobox 2 | p=8.61e$^{-05}$ |
| TLX1 | T-cell leukemia homeobox 1 | p=2.55e$^{-05}$ |
| TSHZ1 | teashirt zinc finger homeobox 1 | p=2.36e$^{-15}$ |
| VENTX | VENT homeobox homolog (Xenopus laevis) | p=4.62e$^{-10}$ |
| VSX1 | visual system homeobox 1 | p=8.61e$^{-35}$ |
| ZFHX2 | zinc finger homeobox 2 | p=1.36e$^{-05}$ |
| ZHX1 | zinc fingers and homeoboxes 1 | p=2.59e$^{-05}$ |
| ZHX3 | zinc fingers and homeoboxes 3 | p=0.00664 |

# P < 0.05 Probability of expression in any breast cancer subtype.

Figure 13

| GENES UP-REGULATED | | | |
|---|---|---|---|
| GENE ID | GENE SYMBOL | FOLD CHANGE | GENE NAME |
| 2570 | GABRR2 | 6.2985 | gamma-aminobutyric acid (GABA) receptor, rho 2 |
| 6373 | CXCL11 | 5.3025 | chemokine (C-X-C motif) ligand 11 |
| 11082 | ESM1 | 5.2902 | endothelial cell-specific molecule 1 |
| 1437 | CSF2 | 5.1778 | colony stimulating factor 2 (granulocyte-macrophage) |
| 84674 | CARD6 | 5.1515 | caspase recruitment domain family, member 6 |
| 5473 | PPBP | 4.8810 | pro-platelet basic protein (chemokine (C-X-C motif) ligand 7) |
| 969 | CD69 | 4.8182 | CD69 molecule |
| 140690 | CTCFL | 3.9577 | CCCTC-binding factor (zinc finger protein)-like |
| 5328 | PLAU | 3.9267 | plasminogen activator, urokinase |
| 26053 | AUTS2 | 3.7451 | autism susceptibility candidate 2 |
| 29785 | CYP2S1 | 3.7201 | cytochrome P450, family 2, subfamily S, polypeptide 1 |
| 51561 | IL23A | 3.5431 | interleukin 23, alpha subunit p19 |
| 4907 | NT5E | 3.5105 | 5'-nucleotidase, ecto (CD73) |
| 3170 | FOXA2 | 3.4862 | forkhead box A2 |
| 3885 | KRT34 | 3.4172 | keratin 34 |
| 3037 | HAS2 | 3.3519 | hyaluronan synthase 2 |
| 151254 | ALS2CR11 | 3.3273 | amyotrophic lateral sclerosis 2 (juvenile) chromosome region, candidate 11 |
| 3641 | INSL4 | 3.3211 | insulin-like 4 (placenta) |
| 6447 | SCG5 | 3.3068 | secretogranin V (7B2 protein) |
| 79589 | RNF128 | 3.2577 | ring finger protein 128 |
| 118429 | ANTXR2 | 3.1932 | anthrax toxin receptor 2 |
| 53836 | GPR87 | 3.1492 | G protein-coupled receptor 87 |
| 54827 | KIAA1383 | 3.1449 | KIAA1383 |
| 7850 | IL1R2 | 3.1347 | interleukin 1 receptor, type II |
| 6372 | CXCL6 | 3.0234 | chemokine (C-X-C motif) ligand 6 (granulocyte chemotactic protein 2) |
| 1009 | CDH11 | 2.9554 | cadherin 11, type 2, OB-cadherin (osteoblast) |
| 84419 | C15orf48 | 2.9349 | chromosome 15 open reading frame 48 |
| 5744 | PTHLH | 2.9316 | parathyroid hormone-like hormone |
| 50486 | G0S2 | 2.9201 | G0/G1switch 2 |
| 81029 | WNT5B | 2.8879 | wingless-type MMTV integration site family, member 5B |
| 57214 | KIAA1199 | 2.8845 | KIAA1199 |
| 3589 | IL11 | 2.8745 | interleukin 11 |
| 4674 | NAP1L2 | 2.8603 | nucleosome assembly protein 1-like 2 |
| 55107 | ANO1 | 2.8547 | anoctamin 1, calcium activated chloride channel |
| 149111 | CNIH3 | 2.8448 | cornichon homolog 3 (Drosophila) |
| 114801 | TMEM200A | 2.8076 | transmembrane protein 200A |

Figure 13 (Continued)

| 1305 | COL13A1 | 2.7352 | collagen, type XIII, alpha 1 |
|---|---|---|---|
| 29126 | CD274 | 2.7201 | CD274 molecule |
| 6567 | SLC16A2 | 2.7038 | solute carrier family 16, member 2 (monocarboxylic acid transporter 8) |
| 3576 | IL8 | 2.6882 | interleukin 8 |
| 53831 | GPR84 | 2.6858 | G protein-coupled receptor 84 |
| 4688 | NCF2 | 2.6721 | neutrophil cytosolic factor 2 |
| 139411 | PTCHD1 | 2.6565 | patched domain containing 1 |
| 64648 | SPANXD | 2.6329 | SPANX family, member E; SPANX family, member D |
| 11174 | ADAMTS6 | 2.6027 | ADAM metallopeptidase with thrombospondin type 1 motif, 6 |
| 4153 | MBL2 | 2.5767 | mannose-binding lectin (protein C) 2, soluble (opsonic defect) |
| 151258 | SLC38A11 | 2.5624 | solute carrier family 38, member 11 |
| 6351 | CCL4 | 2.5140 | chemokine (C-C motif) ligand 4 |
| 84189 | SLITRK6 | 2.5053 | SLIT and NTRK-like family, member 6 |
| 8862 | APLN | 2.4967 | apelin |
| 5055 | SERPINB2 | 2.4938 | serpin peptidase inhibitor, clade B (ovalbumin), member 2 |
| 57829 | ZP4 | 2.4880 | zona pellucida glycoprotein 4 |
| 80215 | C21orf96 | 2.4817 | chromosome 21 open reading frame 96 |
| 3157 | HMGCS1 | 2.4794 | 3-hydroxy-3-methylglutaryl-Coenzyme A synthase 1 (soluble) |
| 203859 | ANO5 | 2.4774 | anoctamin 5 |
| 57458 | TMCC3 | 2.4594 | transmembrane and coiled-coil domain family 3 |
| 51086 | C3orf32 | 2.4509 | chromosome 3 open reading frame 32 |
| 64663 | SPANXC | 2.4504 | SPANX family, member C |
| 3689 | ITGB2 | 2.4116 | integrin, beta 2 (complement component 3 receptor 3 and 4 subunit) |
| 27147 | DENND2A | 2.3977 | DENN/MADD domain containing 2A |
| 558 | AXL | 2.3804 | AXL receptor tyrosine kinase |
| 64232 | MS4A5 | 2.3743 | membrane-spanning 4-domains, subfamily A, member 5 |
| 185 | AGTR1 | 2.3820 | angiotensin II receptor, type 1 |
| 639 | PRDM1 | 2.3820 | PR domain containing 1, with ZNF domain |
| 54796 | BNC2 | 2.3349 | basonuclin 2 |
| 3294 | HSD17B2 | 2.3107 | hydroxysteroid (17-beta) dehydrogenase 2 |
| 5999 | RGS4 | 2.2947 | regulator of G-protein signaling 4 |
| 22822 | PHLDA1 | 2.2815 | pleckstrin homology-like domain, family A, member 1 |
| 256979 | SUNC1 | 2.2799 | Sad1 and UNC84 domain containing 1 |
| 1026 | CDKN1A | 2.2789 | cyclin-dependent kinase inhibitor 1A (p21, Cip1) |
| 9915 | ARNT2 | 2.2679 | aryl-hydrocarbon receptor nuclear translocator 2 |
| 26585 | GREM1 | 2.2527 | gremlin 1, cysteine knot superfamily, homolog (Xenopus laevis) |
| 9173 | IL1RL1 | 2.2475 | interleukin 1 receptor-like 1 |
| 3932 | LCK | 2.2460 | lymphocyte-specific protein tyrosine kinase |

Figure 13 (Continued)

| 84407 | RGS18 | 2.2405 | regulator of G-protein signaling 18 |
|---|---|---|---|
| 283316 | CD163L1 | 2.2243 | CD163 molecule-like 1 |
| 1308 | COL17A1 | 2.2243 | collagen, type XVII, alpha 1 |
| 344558 | SH3RF3 | 2.2232 | SH3 domain containing ring finger 3 |
| 4314 | MMP3 | 2.2199 | matrix metallopeptidase 3 (stromelysin 1, progelatinase) |
| 84364 | ARFGAP3 | 2.2078 | ADP-ribosylation factor GTPase activating protein 2 |
| 7122 | CLDN5 | 2.2039 | claudin 5 |
| 144406 | WDR66 | 2.1987 | WD repeat domain 66 |
| 3936 | LCP1 | 2.1987 | lymphocyte cytosolic protein 1 (L-plastin) |
| 23209 | MLC1 | 2.1873 | megalencephalic leukoencephalopathy with subcortical cysts 1 |
| 220 | ALDH1A3 | 2.1785 | aldehyde dehydrogenase 1 family, member A3 |
| 56131 | PCDHB4 | 2.1772 | protocadherin beta 4 |
| 7422 | VEGFA | 2.1680 | vascular endothelial growth factor A |
| 7462 | LAT2 | 2.1618 | linker for activation of T cells family, member 2 |
| 6751 | SSTR1 | 2.1550 | somatostatin receptor 1 |
| 57580 | PREX1 | 2.1497 | phosphatidylinositol-3,4,5-trisphosphate-dependent Rac exchange factor 1 |
| 7429 | VIL1 | 2.1480 | villin 1 |
| 157310 | PEBP4 | 2.1455 | phosphatidylethanolamine-binding protein 4 |
| 29881 | NPC1L1 | 2.1411 | NPC1 (Niemann-Pick disease, type C1, gene)-like 1 |
| 11009 | IL24 | 2.1358 | interleukin 24 |
| 23743 | BHMT2 | 2.1214 | betaine-homocysteine methyltransferase 2 |
| 273 | AMPD3 | 2.1165 | adenosine monophosphate deaminase (isoform E) |
| 8876 | VNN1 | 2.1118 | vanin 1 |
| 284467 | FAM19A3 | 2.1118 | family with sequence similarity 19 (chemokine (C-C motif)-like), member A3 |
| 256691 | MAMDC2 | 2.1094 | MAM domain containing 2 |
| 1960 | EGR3 | 2.0888 | early growth response 3 |
| 10242 | KCNMB2 | 2.0869 | potassium large conductance calcium-activated channel, subfamily M, beta member 2 |
| 93953 | ACRC | 2.0818 | acidic repeat containing |
| 27071 | DAPP1 | 2.0753 | dual adaptor of phosphotyrosine and 3-phosphoinositides |
| 5053 | PAH | 2.0724 | phenylalanine hydroxylase |
| 256076 | COL29A1 | 2.0722 | collagen, type XXIX, alpha 1 |
| 84953 | MICALCL | 2.0618 | MICAL C-terminal like |
| 2335 | FN1 | 2.0562 | fibronectin 1 |
| 9582 | APOBEC3B | 2.0491 | apolipoprotein B mRNA editing enzyme, catalytic polypeptide-like 3B |
| 23090 | ZNF423 | 2.0477 | zinc finger protein 423 |
| 164668 | APOBEC3H | 2.0477 | apolipoprotein B mRNA editing enzyme, catalytic polypeptide-like 3H |
| 6580 | SLC22A1 | 2.0430 | solute carrier family 22 (organic cation transporter), member 1 |

Figure 13 (Continued)

| GENE ID | GENE SYMBOL | FOLD CHANGE | GENE NAME |
|---|---|---|---|
| 56953 | NT5M | 2.0359 | 5',3'-nucleotidase, mitochondrial |
| 80380 | PDCD1LG2 | 2.0350 | programmed cell death 1 ligand 2 |
| 881 | CCIN | 2.0298 | calicin |
| 374918 | IGFL1 | 2.0246 | IGF-like family member 1 |
| 8647 | ABCB11 | 2.0229 | ATP-binding cassette, sub-family B (MDR/TAP), member 11 |
| 2828 | GPR4 | 2.0162 | G protein-coupled receptor 4 |
| 122786 | FRMD6 | 2.0139 | FERM domain containing 6 |
| 200150 | PLD5 | 2.0104 | phospholipase D family, member 5 |
| 1901 | S1PR1 | 2.0093 | sphingosine-1-phosphate receptor 1 |
| 90576 | ZNF799 | 2.0058 | zinc finger protein 799 |
| 91120 | ZNF662 | 2.0048 | zinc finger protein 662 |
| GENES DOWN REGULATED | | | |
| GENE ID | GENE SYMBOL | FOLD CHANGE | GENE NAME |
| 51438 | MAGEC2 | 0.1109 | melanoma antigen family C, 2 |
| 4948 | OCA2 | 0.2298 | oculocutaneous albinism II |
| 26223 | FBXL21 | 0.2321 | F-box and leucine-rich repeat protein 21 |
| 143662 | MUC15 | 0.2393 | mucin 15, cell surface associated |
| 5179 | PENK | 0.2576 | proenkephalin |
| 8424 | BBOX1 | 0.2719 | butyrobetaine (gamma), 2-oxoglutarate dioxygenase (gamma-butyrobetaine hydroxylase) 1 |
| 64881 | PCDH20 | 0.2835 | protocadherin 20 |
| 9627 | SNCAIP | 0.2914 | synuclein, alpha interacting protein |
| 1580 | CYP4B1 | 0.2948 | cytochrome P450, family 4, subfamily B, polypeptide 1 |
| 22914 | KLRK1 | 0.2951 | killer cell lectin-like receptor subfamily K, member 1 |

Genes listed are those with a more than 2-fold change either up- or down-regulated.

| Term | RT | Count | % | P-Value | Benjamini |
|---|---|---|---|---|---|
| KEGG_PATHWAY | Cytokine-cytokine receptor interaction | 11 | 9 | 3.80E-03 | 2.40E-01 |
| KEGG_PATHWAY | Chemokine signaling pathway | 6 | 4.9 | 1.80E-02 | 4.50E-01 |
| KEGG_PATHWAY | Bladder cancer | 3 | 2.5 | 4.70E-02 | 6.40E-01 |
| KEGG_PATHWAY | Cell adhesion molecules (CAMs) | 4 | 3.3 | 9.40E-02 | 8.00E-01 |

| RT | Genes | Count | % | P-Value | Benjamini |
|---|---|---|---|---|---|
| GOTERM_MF_FAT | cytokine activity | 11 | 9 | 6.80E-07 | 1.80E-04 |
| GOTERM_MF_FAT | chemokine activity | 5 | 4.1 | 2.50E-04 | 3.20E-02 |
| GOTERM_MF_FAT | chemokine receptor binding | 5 | 4.1 | 3.20E-04 | 2.70E-02 |
| GOTERM_MF_FAT | glycosaminoglycan binding | 5 | 4.1 | 1.40E-02 | 6.10E-01 |
| GOTERM_MF_FAT | hydrolase activity, acting on carbon-nitrogen (but not peptide) bonds, in cyclic amidines | 3 | 2.5 | 1.80E-02 | 6.20E-01 |
| GOTERM_MF_FAT | polysaccharide binding | 5 | 4.1 | 2.00E-02 | 5.80E-01 |
| GOTERM_MF_FAT | pattern binding | 5 | 4.1 | 2.00E-02 | 5.80E-01 |
| GOTERM_MF_FAT | growth factor activity | 5 | 4.1 | 2.30E-02 | 5.80E-01 |
| GOTERM_MF_FAT | carbohydrate binding | 7 | 5.7 | 3.10E-02 | 6.50E-01 |
| GOTERM_MF_FAT | heparin binding | 4 | 3.3 | 3.20E-02 | 6.10E-01 |
| GOTERM_MF_FAT | interleukin-1 receptor activity | 2 | 1.6 | 4.60E-02 | 7.10E-01 |
| GOTERM_MF_FAT | 5'-nucleotidase activity | 2 | 1.6 | 5.20E-02 | 7.20E-01 |
| GOTERM_MF_FAT | hedgehog receptor activity | 2 | 1.6 | 5.90E-02 | 7.30E-01 |
| GOTERM_MF_FAT | nucleotidase activity | 2 | 1.6 | 5.90E-02 | 7.30E-01 |
| GOTERM_MF_FAT | interleukin-1 binding | 2 | 1.6 | 6.50E-02 | 7.40E-01 |
| GOTERM_MF_FAT | enzyme activator activity | 6 | 4.9 | 7.40E-02 | 7.60E-01 |
| GOTERM_MF_FAT | chloride channel activity | 3 | 2.5 | 8.40E-02 | 7.80E-01 |
| GOTERM_MF_FAT | chloride ion binding | 3 | 2.5 | 9.40E-02 | 8.00E-01 |
| GOTERM_MF_FAT | anion channel activity | 3 | 2.5 | 9.60E-02 | 7.90E-01 |

Figure 14

Figure 18
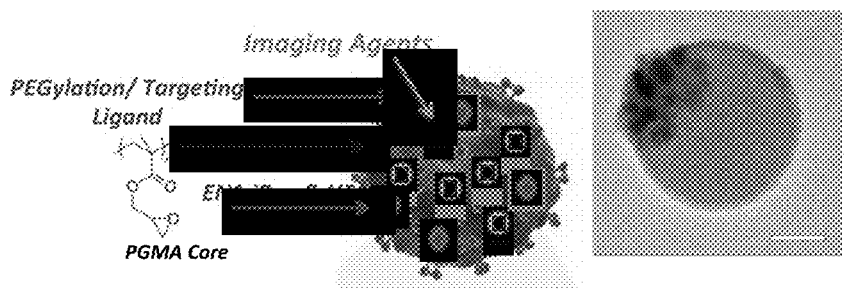
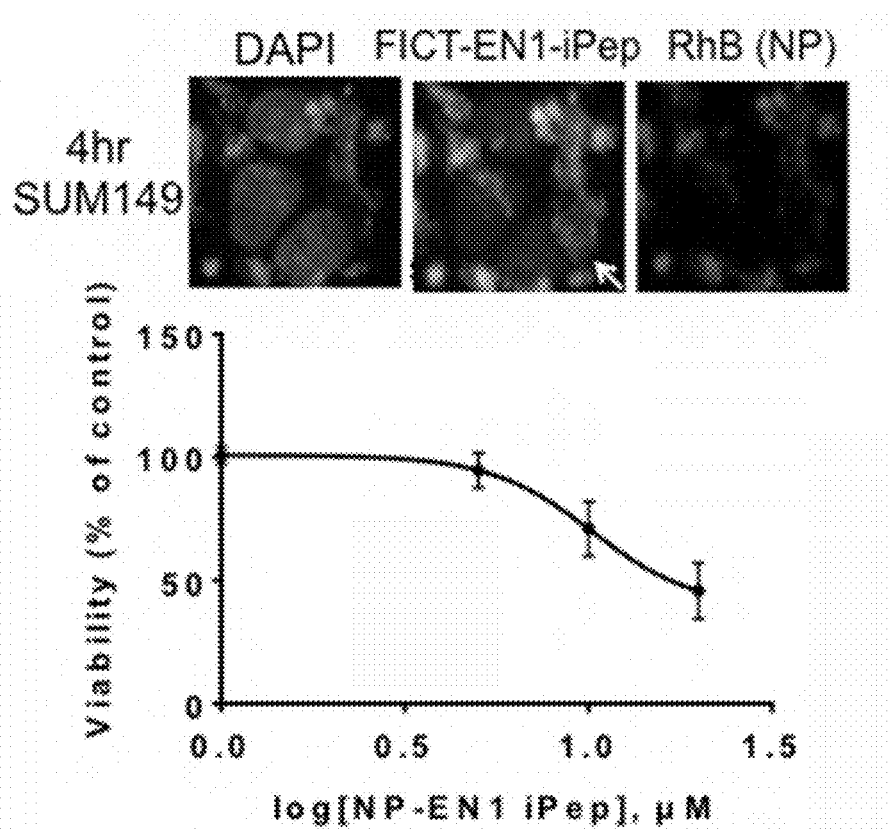

Figure 19
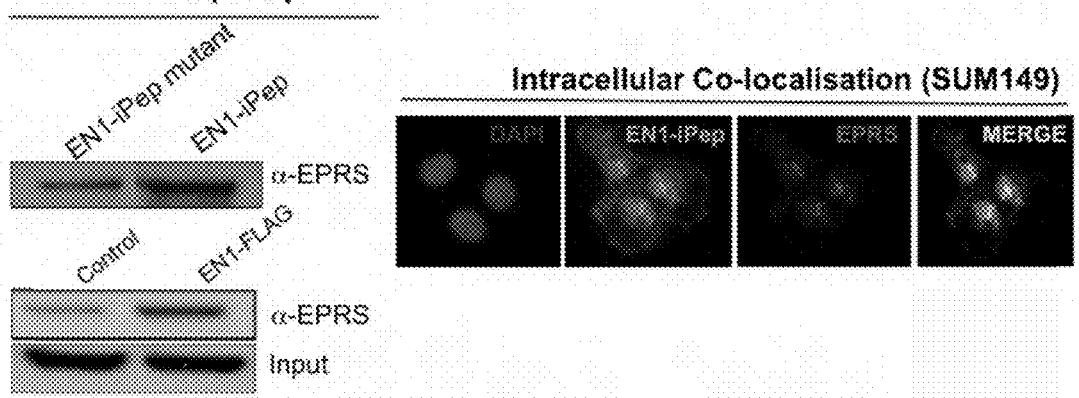
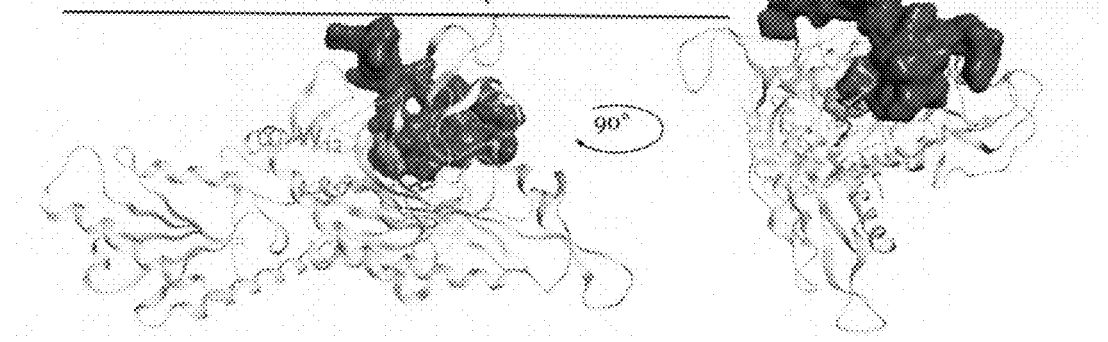

SEQUENCE LISTING

<160> NUMBER OF SEQ ID NOS: 23

<210> SEQ ID NO 1
<211> LENGTH: 23
<212> TYPE: PRT
<213> ORGANISM: Homo sapiens

<400> SEQUENCE: 1

Thr Asp Ser Gln Gln Pro Leu Val Trp Pro Ala Trp Val Tyr Cys Thr
1               5                   10                  15

Arg Tyr Ser Asp Arg Pro Ser
            20

<210> SEQ ID NO 2
<211> LENGTH: 18
<212> TYPE: PRT
<213> ORGANISM: Homo sapiens

<400> SEQUENCE: 2

```
Pro Leu Val Trp Pro Ala Trp Val Tyr Cys Thr Arg Tyr Ser Asp Arg
1               5                   10                  15

Pro Ser
```

<210> SEQ ID NO 3
<211> LENGTH: 13
<212> TYPE: PRT
<213> ORGANISM: Homo sapiens

<400> SEQUENCE: 3

```
Trp Pro Ala Trp Val Tyr Cys Thr Arg Tyr Ser Asp Arg
1               5                   10
```

<210> SEQ ID NO 4
<211> LENGTH: 15
<212> TYPE: PRT
<213> ORGANISM: Homo sapiens

<400> SEQUENCE: 4

```
Pro Leu Val Trp Pro Ala Trp Val Tyr Cys Thr Arg Ser Asp Arg
1               5                   10                  15
```

<210> SEQ ID NO 5
<211> LENGTH: 29
<212> TYPE: PRT
<213> ORGANISM: Homo sapiens

<400> SEQUENCE: 5

```
Lys Lys Lys Arg Lys Val Thr Asp Ser Gln Gln Pro Leu Val Trp Pro
1               5                   10                  15

Ala Trp Val Tyr Cys Thr Arg Tyr Ser Asp Arg Pro Ser
            20                  25
```

<210> SEQ ID NO 6
<211> LENGTH: 24
<212> TYPE: PRT
<213> ORGANISM: Homo sapiens

<400> SEQUENCE: 6

```
Lys Lys Lys Arg Lys Val Pro Leu Val Trp Pro Ala Trp Val Tyr Cys
1               5                   10                  15

Thr Arg Tyr Ser Asp Arg Pro Ser
            20
```

<210> SEQ ID NO 7
<211> LENGTH: 19
<212> TYPE: PRT
<213> ORGANISM: Homo sapiens

<400> SEQUENCE: 7

```
Lys Lys Lys Arg Lys Val Trp Pro Ala Trp Val Tyr Cys Thr Arg Tyr
1               5                   10                  15

Ser Asp Arg
```

<210> SEQ ID NO 8
<211> LENGTH: 20
<212> TYPE: PRT
<213> ORGANISM: Homo sapiens

<400> SEQUENCE: 8

```
Lys Lys Lys Arg Lys Pro Leu Val Trp Pro Ala Trp Val Tyr Cys Thr
1               5                   10                  15
```

Arg Ser Asp Arg
            20

<210> SEQ ID NO 9
<211> LENGTH: 15
<212> TYPE: PRT
<213> ORGANISM: Artificial Sequence
<220> FEATURE:
<223> OTHER INFORMATION: artificially engineered sequence based on homo
      sapiens sequence
<220> FEATURE:
<221> NAME/KEY: Lsub2
<222> LOCATION: (2)..(2)
<223> OTHER INFORMATION: Amino acid is L, M, or I
<220> FEATURE:
<221> NAME/KEY: Vsub3
<222> LOCATION: (3)..(3)
<223> OTHER INFORMATION: Amino acid is V or L
<220> FEATURE:
<221> NAME/KEY: Wsub4
<222> LOCATION: (4)..(4)
<223> OTHER INFORMATION: Amino acid is W, Y, or W analog
<220> FEATURE:
<221> NAME/KEY: Vsub8
<222> LOCATION: (8)..(8)
<223> OTHER INFORMATION: Amino acid is V or I
<220> FEATURE:
<221> NAME/KEY: Ysub9
<222> LOCATION: (9)..(9)
<223> OTHER INFORMATION: Amino acid is Y or F
<220> FEATURE:
<221> NAME/KEY: YCsub10
<222> LOCATION: (10)..(10)
<223> OTHER INFORMATION: Amino acid is C or S

<400> SEQUENCE: 9

Pro Xaa Xaa Xaa Pro Ala Trp Xaa Xaa Xaa Thr Arg Ser Asp Arg
1               5                   10                  15

<210> SEQ ID NO 10
<211> LENGTH: 6
<212> TYPE: PRT
<213> ORGANISM: Artificial Sequence
<220> FEATURE:
<223> OTHER INFORMATION: engineered sequence from homo sapiens

<400> SEQUENCE: 10

Lys Lys Lys Arg Lys Val
1               5

<210> SEQ ID NO 11
<211> LENGTH: 5
<212> TYPE: PRT
<213> ORGANISM: Artificial Sequence
<220> FEATURE:
<223> OTHER INFORMATION: engineered from homo sapiens

<400> SEQUENCE: 11

Lys Lys Lys Arg Lys
1               5

<210> SEQ ID NO 12
<211> LENGTH: 20
<212> TYPE: PRT
<213> ORGANISM: Artificial Sequence
<220> FEATURE:
<223> OTHER INFORMATION: engineered from homo sapiens
<220> FEATURE:
<221> NAME/KEY: Lsub2
<222> LOCATION: (7)..(7)
<223> OTHER INFORMATION: aminio acid is L, M or I

```
<220> FEATURE:
<221> NAME/KEY: Vsub3
<222> LOCATION: (8)..(8)
<223> OTHER INFORMATION: aminio acid is V or L
<220> FEATURE:
<221> NAME/KEY: Wsub4
<222> LOCATION: (9)..(9)
<223> OTHER INFORMATION: aminio acid is W, Y or W analog
<220> FEATURE:
<221> NAME/KEY: Vsub8
<222> LOCATION: (13)..(13)
<223> OTHER INFORMATION: aminio acid is V or I
<220> FEATURE:
<221> NAME/KEY: Ysub9
<222> LOCATION: (14)..(14)
<223> OTHER INFORMATION: aminio acid is Y or F
<220> FEATURE:
<221> NAME/KEY: Csub10
<222> LOCATION: (15)..(15)
<223> OTHER INFORMATION: aminio acid is C or S

<400> SEQUENCE: 12

Lys Lys Lys Arg Lys Pro Xaa Xaa Xaa Pro Ala Trp Xaa Xaa Xaa Thr
1               5                   10                  15

Arg Ser Asp Arg
            20

<210> SEQ ID NO 13
<211> LENGTH: 6
<212> TYPE: PRT
<213> ORGANISM: Homo sapiens

<400> SEQUENCE: 13

Trp Pro Ala Trp Val Tyr
1               5

<210> SEQ ID NO 14
<211> LENGTH: 6
<212> TYPE: PRT
<213> ORGANISM: Artificial Sequence
<220> FEATURE:
<223> OTHER INFORMATION: engineered from homo sapiens

<400> SEQUENCE: 14

Gly Gly Ala Gly Ala Gly
1               5

<210> SEQ ID NO 15
<211> LENGTH: 6
<212> TYPE: PRT
<213> ORGANISM: Artificial Sequence
<220> FEATURE:
<223> OTHER INFORMATION: engineered from homo sapiens

<400> SEQUENCE: 15

Gly Ala Ala Gly Ala Gly
1               5

<210> SEQ ID NO 16
<211> LENGTH: 9
<212> TYPE: PRT
<213> ORGANISM: Homo sapiens

<400> SEQUENCE: 16

Cys Thr Arg Tyr Ser Asp Arg Pro Ser
1               5

<210> SEQ ID NO 17
```

```
<211> LENGTH: 8
<212> TYPE: PRT
<213> ORGANISM: Homo sapiens

<400> SEQUENCE: 17

Asp Tyr Lys Asp Asp Asp Asp Lys
1               5

<210> SEQ ID NO 18
<211> LENGTH: 29
<212> TYPE: PRT
<213> ORGANISM: Artificial Sequence
<220> FEATURE:
<223> OTHER INFORMATION: engineered from homo sapiens

<400> SEQUENCE: 18

Lys Lys Lys Arg Lys Val Thr Asp Ser Gln Gln Pro Leu Val Gly Ala
1               5                   10                  15

Ala Gly Ala Gly Cys Thr Arg Tyr Ser Asp Arg Pro Ser
            20                  25

<210> SEQ ID NO 19
<211> LENGTH: 29
<212> TYPE: PRT
<213> ORGANISM: Artificial Sequence
<220> FEATURE:
<223> OTHER INFORMATION: engineered from homo sapiens

<400> SEQUENCE: 19

Lys Lys Lys Arg Lys Val Thr Asp Ser Gln Gln Pro Leu Val Trp Pro
1               5                   10                  15

Ala Ala Val Tyr Cys Thr Arg Tyr Ser Asp Arg Pro Ser
            20                  25

<210> SEQ ID NO 20
<211> LENGTH: 29
<212> TYPE: PRT
<213> ORGANISM: Artificial Sequence
<220> FEATURE:
<223> OTHER INFORMATION: engineered from homo sapiens

<400> SEQUENCE: 20

Lys Lys Lys Arg Lys Val Thr Asp Ser Gln Gln Pro Leu Val Ala Pro
1               5                   10                  15

Ala Trp Val Tyr Cys Thr Arg Tyr Ser Asp Arg Pro Ser
            20                  25

<210> SEQ ID NO 21
<211> LENGTH: 24
<212> TYPE: PRT
<213> ORGANISM: Homo sapiens

<400> SEQUENCE: 21

Lys Lys Lys Arg Lys Val Pro Leu Val Trp Pro Ala Trp Val Tyr Cys
1               5                   10                  15

Thr Arg Tyr Ser Asp Arg Pro Ser
            20

<210> SEQ ID NO 22
<211> LENGTH: 19
<212> TYPE: PRT
<213> ORGANISM: homo sapiens

<400> SEQUENCE: 22
```

```
Lys Lys Lys Arg Lys Val Trp Pro Ala Trp Val Tyr Cys Thr Arg Tyr
1               5                   10                  15

Ser Asp Arg

<210> SEQ ID NO 23
<211> LENGTH: 19
<212> TYPE: PRT
<213> ORGANISM: Artificial Sequence
<220> FEATURE:
<223> OTHER INFORMATION: engineered from homo sapiens

<400> SEQUENCE: 23

Lys Lys Lys Arg Lys Val Ala Pro Ala Ala Val Tyr Cys Thr Arg Tyr
1               5                   10                  15

Ser Asp Arg
```

INTERFERENCE PEPTIDES AND USE THEREOF

FIELD OF THE INVENTION

The present invention relates generally to interference peptides for treating cancers. More specifically, the invention relates to interference peptides that selectively induce apoptosis of EN1 and EN2 expressing cancer cells and their use thereof.

BACKGROUND TO THE INVENTION

Basal-like breast tumors are aggressive cancers associated with high proliferation and metastasis. Basal-like breast cancers lack expression of estrogen receptor (ER), progesterone receptor (PR), and epidermal growth factor receptor-2 (HER2). Some extremely aggressive basal-like breast cancers are also associated with hypoxia, inflammation and high leukocyte infiltration. The presence of stem-cell-like signatures is a hallmark of these tumors. The response of these cancer types to first-line chemotherapy is often hindered by developed resistance to treatment, recurrence, and metastatic disease. High expression of inflammation and angiogenesis-related metagenes are associated with poor prognosis. Importantly, there is a lack of selective therapeutic agents to target these tumors and patients are left only with chemotherapy options.

Recent large-scale studies of breast carcinomas have elucidated the fundamental role of Transcription Factors (TFs) as driving forces of oncogenesis in basal-like cancers. Notably, many developmental Homeodomain (HD) containing TFs ($TF_{HD}$s) are aberrantly expressed in cancer and are drivers of cancer initiation, disease recurrence, and resistance to treatment. However, despite their critical role in cancer, TFs have not been successfully targeted with conventional small molecules and have been considered "undruggable".

The preceding discussions of the background art is intended to facilitate an understanding of the present invention only. The discussion is not an acknowledgement or admission that any of the material referred to is or was part of the common general knowledge as at the priority date of the application.

SUMMARY OF THE INVENTION

The inventors have identified the critical role of the neural-specific $TF_{HD}$, EN1, in controlling inflammatory signals, survival and resistance to cell death in highly aggressive basal-like breast cancers having stem/progenitor cell characteristics. More specifically, the inventors have unveiled EN1 as an activator of intrinsic inflammatory pathways associated with pro-survival in the highly resistant basal-like breast tumours. The inventors built upon this discovery by engineering interference peptides comprising the highly conserved EN1-hexamotif sequence involved in protein-protein interactions as a new, selective therapeutic strategy for inducing potent and selective apoptosis in basal-like breast tumours and other cancers overexpressing EN1 and EN2.

Accordingly, the present invention provides isolated and purified peptides comprising:
(i) an amino acid sequences of any one of SEQ ID NOs: 1 to 8; or
(ii) the amino acid sequence $PL_2V_3W_4PAWV_8Y_9C_{10}TRSDR$ (SEQ ID NO: 9), wherein:
$L_2$ is one of: L, M, or I;
$V_3$ is one of: V or L;
$W_4$ is one of: W, Y, or W analog;
$V_8$ is one of: V or I;
$Y_9$ is one of: Y or F; and
$C_{10}$ is one of: C or S.

In an embodiment, the invention provides peptides comprising the amino acid sequences of any one of SEQ ID NOs: 1 to 4, attached to a cell penetrating peptide. In a preferred form, the invention provides isolated and purified peptides comprising:
(i) an amino acid sequences of SEQ 1D NOs: 1 to 4; or
(ii) the amino acid sequence $PL_2V_3W_4PAWV_8Y_9C_{10}TRSDR$ (SEQ ID NO: 9), wherein:
$L_2$ is one of: L, M, or I;
$V_3$ is one of: V or L;
$W_4$ is one of: W, Y, or W analog;
$V_8$ is one of: V or I;
$Y_9$ is one of: Y or F; and
$C_{10}$ is one of: C or S;
attached to a means for introducing the one or more peptides into a cell, and particularly a cancer cell.

In a highly preferred embodiment of the invention, the means for introducing the one or more peptides into a cell is preferably also capable of nuclear localisation of the peptide. Desirably, nuclear localisation is achieved by attaching to the peptide(s), herein described, the amino acid sequence: KKKRKV (SEQ ID NO: 10) or KKKRK (SEQ ID NO: 11).

The present invention also provides an isolated polynucleotide encoding a peptide of the invention as described herein.

Also provided is an expression vector encoding a peptide of the invention as described herein, and a host cell comprising nucleic acid encoding a peptide of the invention as described herein.

The present invention provides a composition comprising a peptide of the invention as described herein. Also provided is said composition and a means for introducing the peptide into a cell. The means for introducing the peptide into a cell is preferably a nanoparticle, and more preferably a tumor-specific nanoparticle.

The present invention further provides a method for preventing interaction of EN1 to EPRS in a cell, comprising introducing into the cell a peptide of the invention as described herein which interacts with EPRS therein preventing interaction of EPRS to EN1. The present invention provides a method of inducing apoptosis in a cell expressing either or both of EN1 and EN2, the method comprising introducing into the cell a peptide of the invention as described herein. The present invention provides a method of activating the caspase 3 pathway in a cell expressing either or both of EN1 and EN2, the method comprising introducing into the cell a peptide of the invention as described herein. Preferably, the cell is a cancer cell. More preferably, the cancer cell expresses EN1 and is a: breast cancer cell, basal-like breast cancer cell, ovarian cancer cell, salivary gland adenoid cystic carcinoma cell, medulloblastoma cell, or a cell from a tumor originating in the cerebellum; or a cancer cell expressing EN2 and is a neuroblastoma cell, a breast cancer cell, or a prostate cancer cell.

The present invention also provides a method of treating an EN1 or EN2 expressing cancer in a subject including the step of introducing one or more peptides of the invention as described herein into the cancer cells. Preferably, the cancer is an EN1 expressing basal-like breast cancer. More preferably, the subject is a human.

The present invention provides a use of a peptide of the invention as described herein to interact with EPRS and prevent binding of EN1 to EPRS in a cell. The present invention also provides a use of a peptide of the invention as described herein for inducing death, and preferably apoptosis, of an EN1 or EN2 expressing cell. The invention also provides a use of a peptide of the invention as described herein for activating the caspase 3 pathway in an EN1 or EN2 expressing cell. Preferably the cell is a cancer cell. More preferably, the cancer cell expresses EN1 and is a: breast cancer cell, a basal-like breast cancer cell, an ovarian cancer cell, a medulloblastoma cell or a cell from another tumor originating in the cerebellum, or a salivary gland adenoid cystic carcinoma cell; or the cancer cell expresses EN2 and is a neuroblastoma cell, a breast cancer cell, or a prostate cancer cell. In one embodiment, the peptide of the invention as described herein is introduced into a cell. A nanoparticle, and more preferably a tumor-specific nanoparticle may be used to introduce the peptide into the cell. In another embodiment, the peptide of the invention as described herein is expressed in the cell. Preferably, the peptide of the invention as described herein is expressed in the cell using an expression vector encoding the peptide.

The present invention further provides a use of a peptide of the invention as described herein for treating an EN1 or EN2 expressing cancer in a subject. Preferably, the cancer is an EN1 expressing basal-like breast cancer cell.

The present invention also provides a use of a combination of one or more chemotherapeutic drugs, and a peptide of the invention as described herein, for treating a subject with cancer, wherein the cancer cells express either or both of EN1 and EN2. Preferably, the IC50 of the chemotherapeutic drugs is reduced when compared to use of the one or more chemotherapeutic drugs for treating the subject without the peptide. The combination treatment may be administered to the subject concomitantly or sequentially. Preferably, the peptide is administered to the subject following treatment with the one or more chemotherapeutic drugs. More preferably, the subject is a human.

The present invention provides a use of an effective amount of a peptide of the invention as described herein in the manufacture of a medicament for treating an EN1 or EN2 expressing cancer. Preferably, the cancer is a EN1 expressing basal-like breast cancer.

The present invention further provides a pharmaceutical composition comprising a peptide of the invention as described herein.

The present invention also provides a kit for treating an EN1 or EN2 expressing cancer in a subject, comprising at least one of:
(i) a peptide of the invention as described herein;
(ii) an isolated or synthetic polynucleotide encoding a peptide of the invention as described herein;
(iii) an expression vector encoding a peptide of the invention as described herein; or
(iv) a host cell comprising nucleic acid encoding a peptide of the invention as described herein. Preferably, the subject is a human.

The present invention further provides a pharmaceutical composition comprising a peptide of the invention as described herein.

The present invention provides a use of EN1 as a biomarker for identifying EN1-expressing cancer cells. Preferably, the cancer is: breast cancer, basal-like breast cancer, ovarian cancer, salivary gland adenoid cystic carcinoma medulloblastoma, or a tumor originating in the cerebellum. More preferably, the cancer cells are one or more of: breast cancer cells, basal-like breast cancer cells, ovarian cancer cells, medulloblastoma cells or cells from other tumors originating in the cerebellum, salivary gland adenoid cystic carcinoma cells; that are in or have been removed from a subject.

The present invention further provides a method for identifying cancer cells in a subject comprising the steps of:
(i) quantifying the levels of expression of EN1 in cells that are in or have been removed from a subject; and
(ii) comparing the expression levels to EN1 expression levels of known cancer cells. Preferably, the cancer cells are EN1 expressing: breast cancer cells, basal-like breast cancer cells, ovarian cancer cells, medulloblastoma cells, cells from a tumor originating in the cerebellum, or salivary gland adenoid cystic carcinoma cells.

BRIEF DESCRIPTION OF THE DRAWINGS

Further features of the invention will now become apparent from the following description, by way of example only, with reference to the accompanying Figures and SEQ ID NOs: 1 to 8. In the figures.

Figure 3:
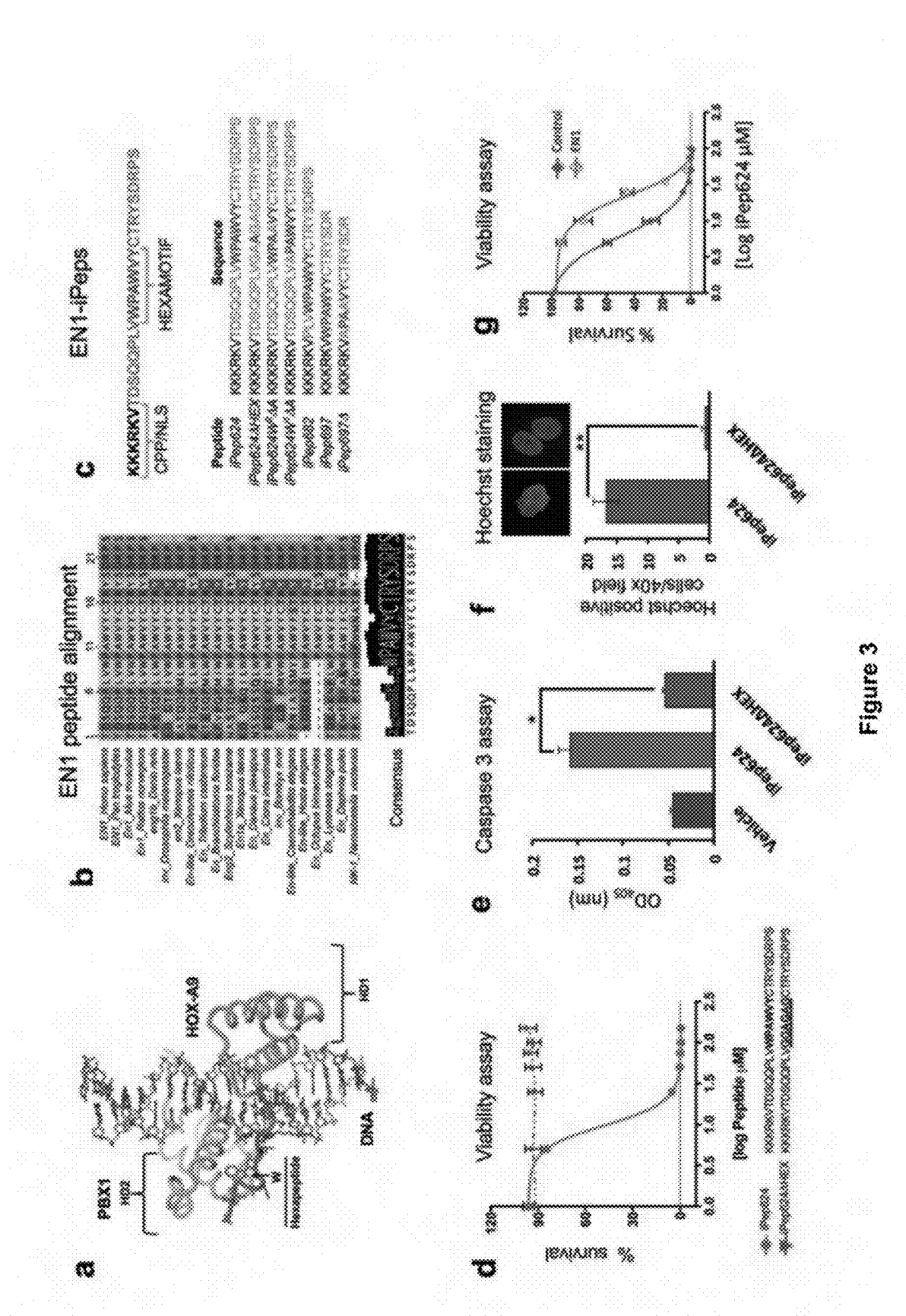

FIG. 3 Design of an EN1-specific interference peptide (EN1-iPep). (a) Molecular model of HOXA9 and PBX1 tertiary complex formation with the DNA (PDB: 1PUF). HOXA9 (hexapeptide "donor") is shown in green; PBX ("partner") in blue. The N-terminal peptide of HOXA9 (magenta) is essential to make contact with the DNA minor groove, as well as to stabilize the binding of HOXA9 with PBX1. The conserved tryptophan residue (W, arrow) is shown within the hexapeptide and it is responsible for anchoring the loop in PBX1. HD=Homeodomain. (b) A multiple alignment of the EN1-iPeps across species, with the consensus sequence of the iPep indicated below. (c) Design of the EN1 specific interference peptide iPep composed of 23 amino acids; the hexamotif is shown in blue and the six amino acid cell penetration/nuclear localization sequence (CPP/NLS) is indicated in black in which; Pep624 has sequence KKKRKVTDSQQPLVWPAWVYCTRYSDRPS (SEQ ID NO:5), iPep624ΔHEX has sequence KKKRK-VTDSQQPLVGAAGAGCTRYSDRPS (SEQ ID NO: 18), iPep624W$^2$ΔA has sequence KKKRKVTDSQQPLVW-PAAVYCTRYSDRPS (SEQ ID NO: 19), iPep624W$^1$ ΔA has sequence KKKRKVTDSQQPLVAPAWVYCTRYS-DRPS (SEQ ID NO: 20), iPep682 has sequence KKKRK-VPLVWPAWVYCTRYSDRPS (SEQ ID NO: 21), iPep697 KKKRKVWPAWVYCTRYSDR (SEQ ID NO: 22), and iPep697Δ has sequence KKKRKVAPAAVYCTRYSDR (SEQ ID NO: 23). (d) Dose-response curve showing cell viability against increasing concentrations of active iPep624 (SEQ ID NO: 5) or mutant iPep624ΔHEX (SEQ ID NO: 18) peptide in SUM149PT cells. Cells were treated for 8 hours and cell viability assessed by Cell Titer Glo assay (CTG). Percentage of survival (%) was normalized to the vehicle treated cells. Determination of fifty percent inhibitory concentrations (IC50) was performed using a nonlinear regression method (curve fit) with the GraphPath software. (e) Caspase 3 activity in SUM149PT cells measured after eight hours of iPep624 (SEQ ID NO: 5) or iPep624ΔHEX (SEQ 11 NO: 18) treatment. Average and standard deviation of three independent experiments is indicated. Statistical significance was analyzed using the Student t-Test (*** p<0.001). (f) Hoechst positive cells in iPep624 (SEQ ID NO: 5) or iPep624ΔHEX (SEQ ID NO: 18) treated cells. Pictures on the top show the morphology of the nucleus after eight hours of iPep treatment. Histogram represents the quantification of Hoechst positive cells per field of view at 40× magnification. (g) Dose-response plots of stable SUM149PT cell lines overexpressing the EN1 cDNA or EGFP (control cells) treated with increasing concentrations of the iPep624 for 72 hours. Cell viability was assessed by Cell Titer Glo (CTG) assay and percentage of survival (%) was normalized to the control treated cells. Determination of fifty percent inhibitory concentrations (IC50) was performed using a non-linear regression method.

Figure 4:
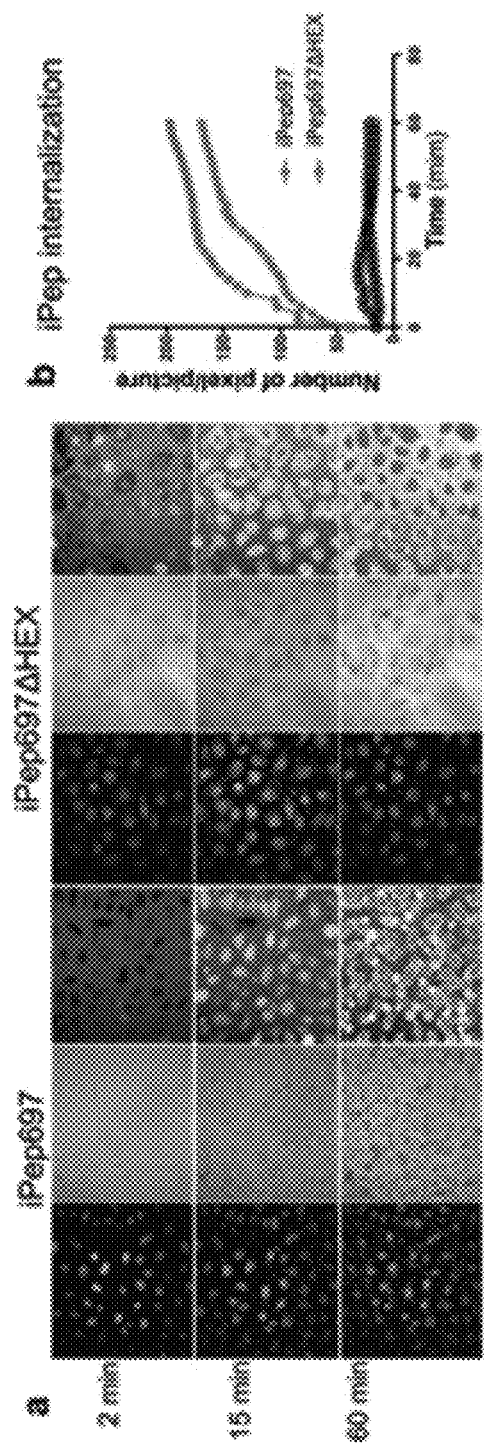

FIG. 4 Internalization kinetics of fluorescently labeled iPeps in SUM149-PT cells. (a) Real-time imaging of the EN1-specific iPep697 (SEQ ID NO: 22) and the mutant iPep697ΔHEX (SEQ ID NO: 23) conjugated with a C-terminal fluorescein by confocal microscopy. Cells were treated with 15 μM of iPep and imaged every two minutes during one hour. Images at 2 min, 15 min and 60 min were taken at 40× magnification.
(b) Quantification of pixels during the real-time imaging of the iPep697 (SEQ ID NO: 22) and iPep697ΔHEX (SEQ ID NO: 23) in either green or blue channel over a 60 min period.

Figure 5:
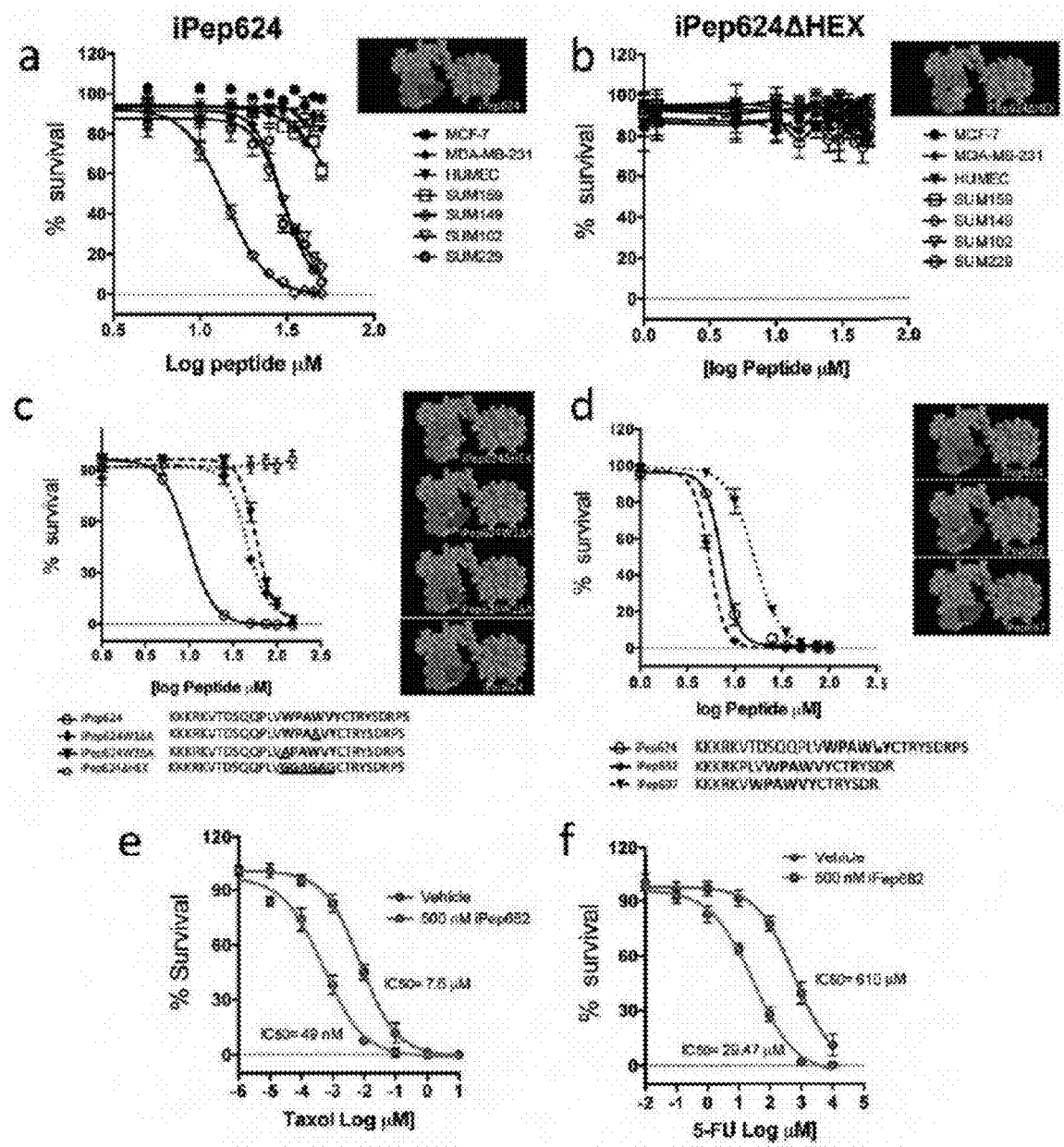

FIG. 5 EN1-iPeps selectively target basal-like breast cancer lines expressing EN1. (a-b) Dose-response plots showing cell viability against increasing concentrations of iPep624 (a) or iPep624ΔHEX (b, hexamotif WPAWVY (SEQ ID NO: 13) mutated to GGAGAG (SEQ ID NO: 14)) in a panel of breast cancer cell lines. Cells were treated with the iPep for 8 hours and cell viability assessed by Cell Titer Glo (CTG) assays. Percentage of survival (%) was normalized to the vehicle treated cells. Determination of fifty percent inhibitory concentrations (IC50) was performed using a non-linear regression method. (c) Dose-response plot of SUM149PT cells treated with increasing concentrations of iPep624 (SEQ ID NO: 5), iPep624W1ΔA (SEQ ID NO: 20) (first tryptophan mutated to alanine), iPep624W2ΔA (SEQ ID NO: 19) (second tryptophan mutated to alanine) and iPep624ΔHEX (SEQ ID NO: 18) (hexamoti WPAWVY (SEQ ID NO: 13) mutated to GGA-GAG (SEQ ID NO: 14)). Percentage of survival and IC50s were calculated as described above. (d) Dose-response plot of SUM149PT cell treated the iPep624 (SEQ ID NO: 5) (29-mer) iPep682 (SEQ ID NO: 21) (22-mer), and iPep697 (SEQ ID NO: 22) (19-mer). Percentage of survival and 1050s were calculated as describe above. (e) Dose-response plots of SUM149PT treated with 500 nM iPep682 (SEQ ID NO: 21) and increasing concentrations of Taxol or 5-fluouracil (5-FU, f). Cells were challenged with Taxol or 5-FU for 60 hours and then treated with the iPep682 (SEQ ID NO: 21) for 8 additional hours. Cell viability was assessed by a Cell Titter Glo (CTG) assay and percentage of survival (%) was normalized to the fixed iPep concentration.

Figure 6:
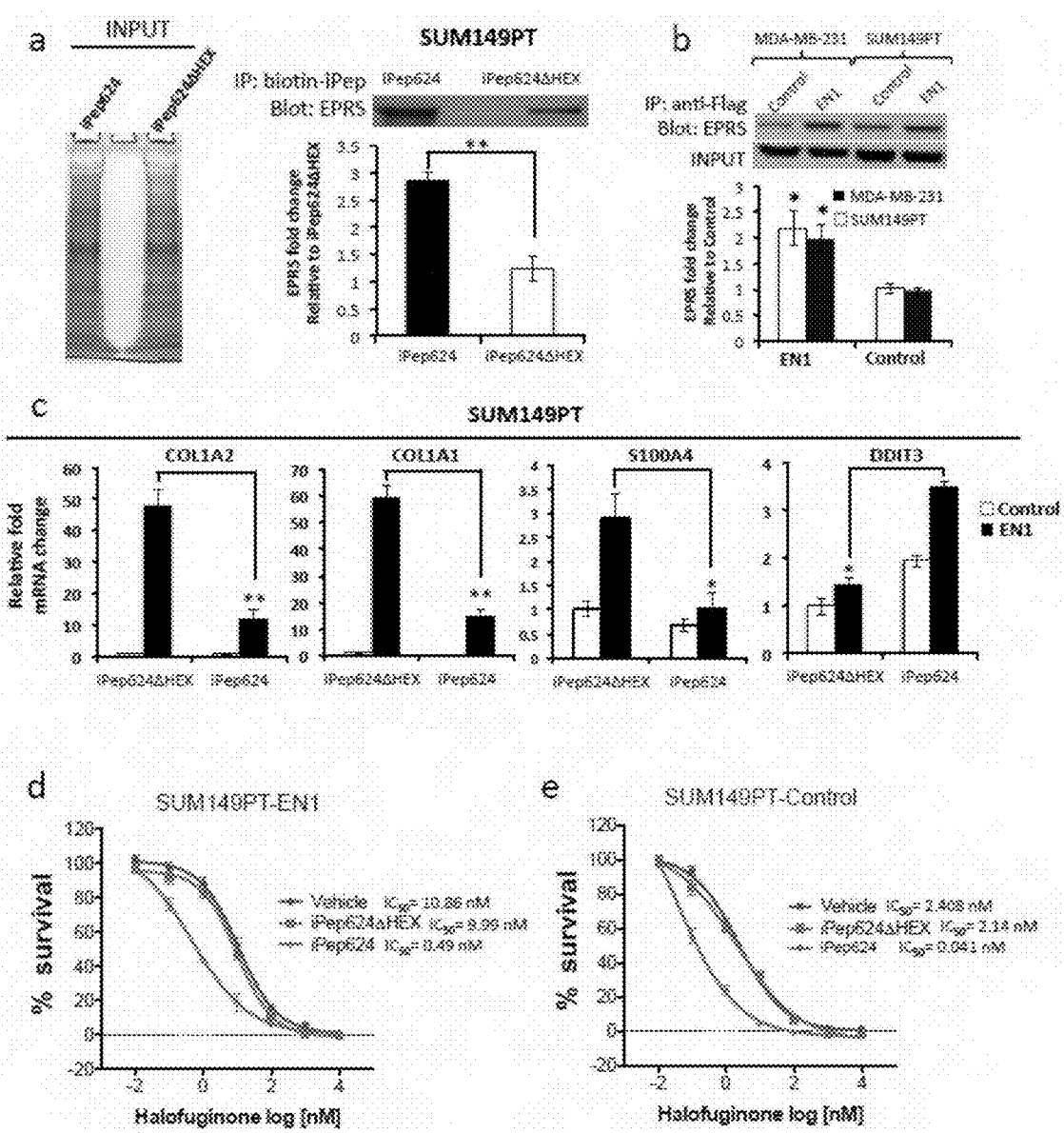

FIG. 6 EN1-Ipeps binds the endogenous Glutamyl-Prolyl tRNA synthetase (EPRS) target and regulates downstream EPRS effectors in breast cancer cells. (a) EN1-iPep624 (SEQ ID NO: 5) captures and binds EPRS from total extracts of SUM149-PT cells. Affinity-capture immunoprecipitation and western blot detection of EPRS using biotinylated iPeps as bait, and total extracts of SUM149-PT cells. Same input loading of extract is shown in the SDS-PAGE gel on the left. The enrichment of the immunoprecipitated products was quantitated using IMAGE J software and normalized to inactive iPep624ΔHEX (SEQ ID NO: 18) peptide. The immunoprecipitations were done at least three times and averages and standard errors between experiments are indicated (p<0.01*, p<0.001**). (b) Full length EN1 binds the endogenous EPRS in MDA-MB-231 and SUM149PT cells. Total extracts of MDA-MB-231 and SUM149PT expressing either a full length EN1 cDNA engineered with a N-terminal FLAG tag or an empty-vector control were processed by immunoprecipitation with an anti-FLAG antibody. Immunoprecipitated complexes were blotted with an EPRS-specific antibody to detect endogenous EPRS. The same amount of loaded extracts (INPUT) is shown with anti-tubulin as endogenous control. The enrichment of the immunoprecipitated products was determined by quantification of the bands by densitometry as described above, and data was normalized to iPep624ΔHEX (SEQ ID NO: 18) control. The immunoprecipitations were independently-performed at least three times and averages and standard errors between experiments are indicated (p<0.01*, p<0.001**).

(c) EN1-iPep624 (SEQ ID NO: 5) regulates well-known downstream effectors of EPRS. SUM149PT cells overexpressing either the EN1-cDNA or an empty vector control (control) were challenged to 15 µM of active EN1-iPep624 (SEQ ID NO: 5) or inactive iPep624ΔHEX (SEQ ID NO: 18) control peptide. Cells were processed for qPCR expression analysis to detect mRNA levels. Fold change mRNA regulation was normalized for each detector to iPep624ΔHEX (SEQ ID NO: 18) control (p<0.01*, p<0.001**). (d) EN1-iPep624 (SEQ ID NO: 5) but not iPep624ΔHEX (SEQ ID NO: 18) control sensitizes SUM149PT cells to the EPRS inhibitor halofuginone. EN1-cDNA and control vector overexpressing cells were treated with 500 nM of iPep and challenged with increasing concentrations of halofuginone for a total period of 48 hours. Cell viability was determined by a Cell Titer Glo assay and IC50 concentrations determined as described in FIG. 5. SUM149PT cells overexpressing either the EN1-cDNA (FIG. 6(d)) or an empty vector control (control) (FIG. 6(e)) were challenged to 15 µM of active EN1-iPep624 or inactive . . . iPep624ΔHEX control (p<0.01*, p<0.001**). In FIG. 6(d) EN1-iPep624 but not iPep624ΔHEX control sensitizes SUM149PT cells to the EPRS inhibitor halofuginone. EN1-cDNA (FIG. 6(d)) and control vector (FIG. 6(e)).

Figure 7:
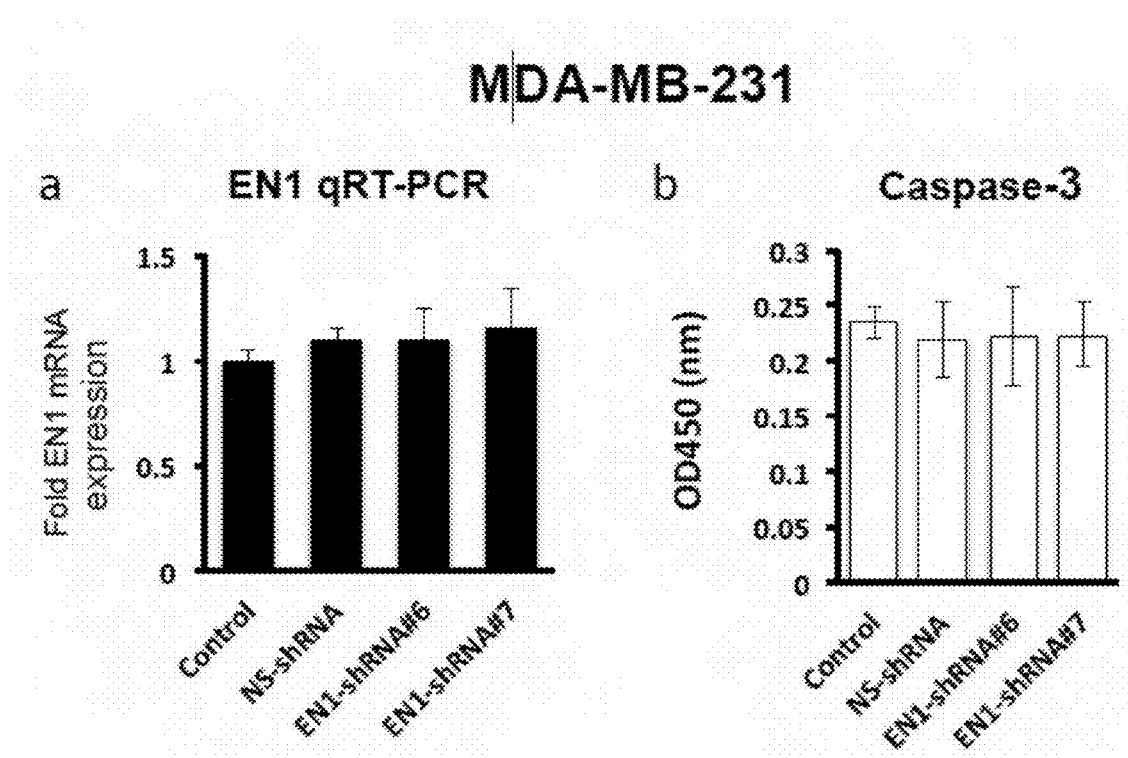

FIG. 7 ShRNA-mediated knockdown of EN1 in MDA-MB-231 cells. (a) EN1 mRNA levels by qRT-PCR in shRNA-transfected MDA-MB-231 breast cancer cells. (b) Caspase 3 activity in transfected cells after 72 hours of shRNA treatment. MDA-MB-231 cells were transduced with a non-specific shRNA or with EN1-specific shRNAs (shRNA#6 and shRNA #7).

Figure 8:
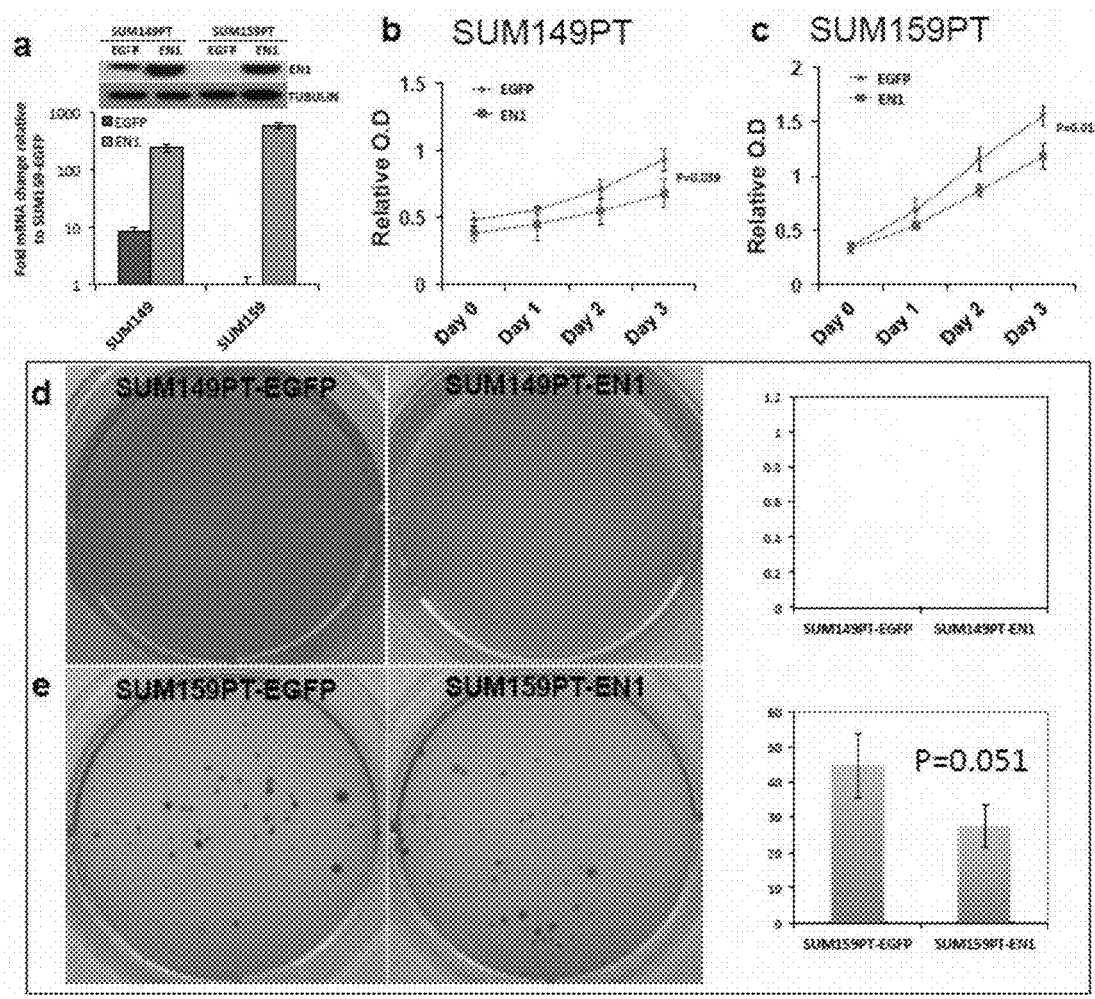

FIG. 8 Overexpression of EN1 cDNA does not result in an increase of tumorigenic potential in vitro. A. EN1 expression levels by qRT-PCR and WB in SUM149PT and SUM159PT cells transduced with either control (EGFP vector) or EN1 cDNA. (b-c) Cell viability assays of SUM149PT (b) and SUM159PT (c) cells transduced cells. Stable cell lines were plated in 96-wells (4 wells per sample set) and cell viability was monitored over time using a Cell Titer Glo assay. The experiment was repeated three times. Statistically significant differences in cell viability were detected at day 3 (72 hrs post-seeding of the cells); SUM149PT, p=0.039 and SUM159PT, p=0.013 relative to the EGFP control d-e. Tumor formation assays on soft-agar in SUM149PT (d) and SUM159PT (e) cell lines stably expressing EGFP or EN1 cDNAs. Tumor cells were seeded in soft agar and incubated for 21 days, then stained with 0.005% crystal violet. A quantification of the number of soft agar colonies is shown. No significant differences in colony numbers between the EN1 cDNA and control EGFP samples were found in three independent experiments (p=0.051).

Figure 9:
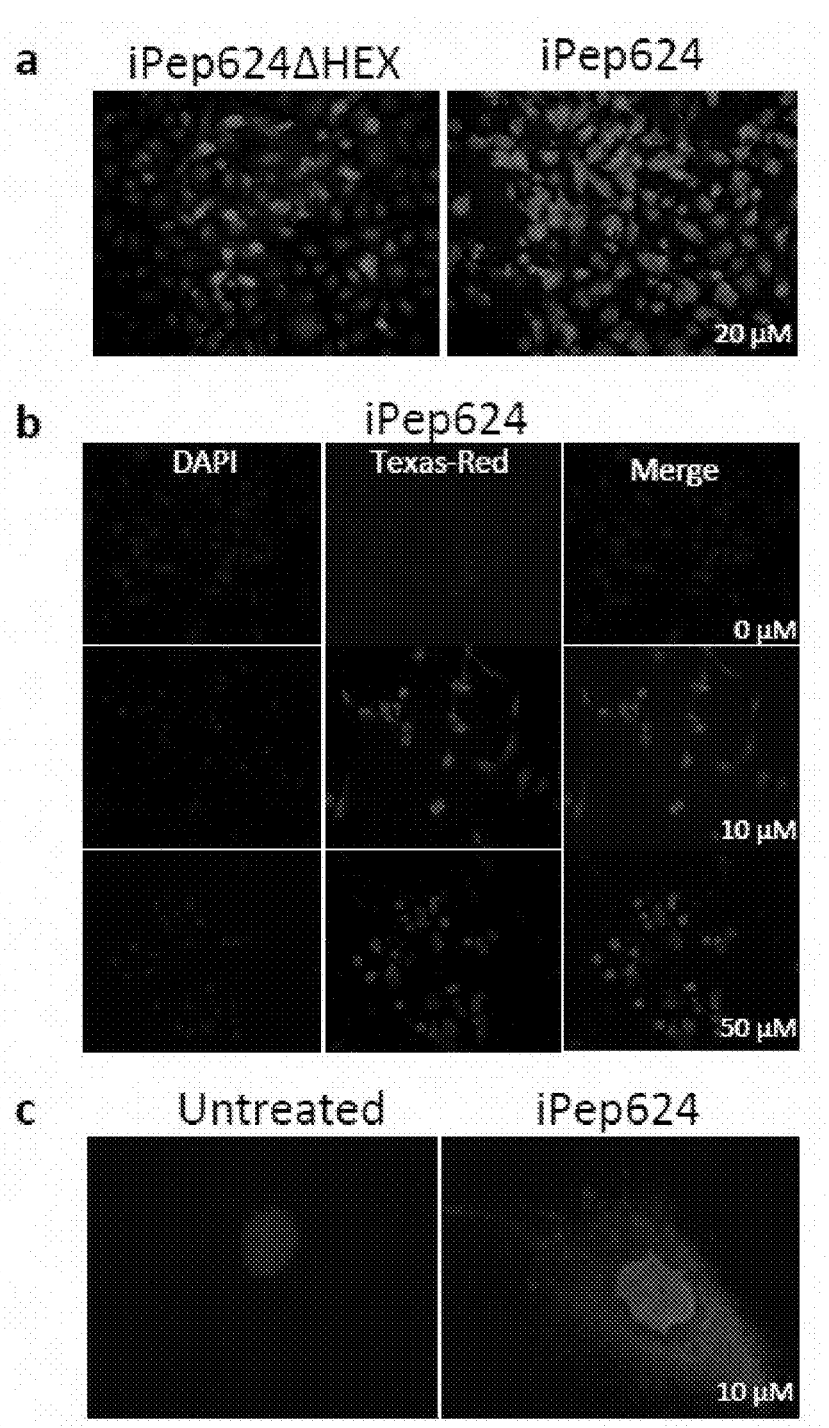

FIG. 9 Delivery of EN1-iPeps and mutant iPeps results in both, nuclear and cytoplasmic localization. (a) SUM149PT cells treated with 20 µM iPep624 (SEQ ID NO: 5) or iPep624ΔHEX (SEQ ID NO: 18), for 8 hours incubation time. The C-terminal of the peptide was labeled with a Biotin to allow the intracellular detection of the peptide with streptavidin-Texas red conjugates. (b) SUM149PT cells treated with 0, 10 and 50 µM concentrations of biotin-labeled iPep624 (SEQ ID NO: 5) showing a concentration-dependent internalization in the cancer cells. Images were taken at 40×. (c) Detail of a single SUM149PT cell treated with 10 µM of iPep624 (SEQ ID NO: 5) outlining both, nuclear and cytoplasmic localization. An untreated SUM149PT cell is indicated as control to show morphological differences between the nucleus of untreated and iPep-treated cells.

Figure 10:
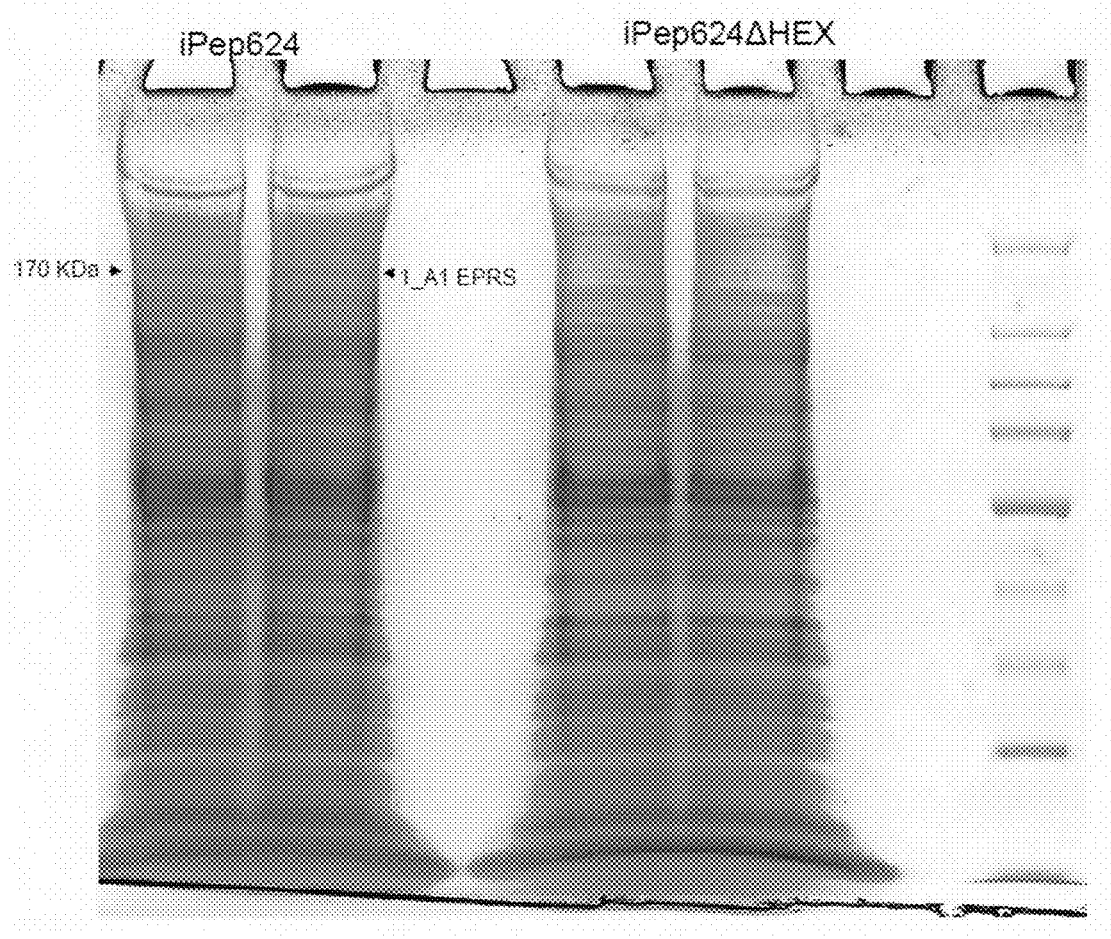

FIG. 10 SDS-PAGE gel outlining the bands differentially bound to iPep624 (SEQ ID NO: 5) and not in control iPep624ΔHEX (SEQ ID NO: 18). Experiments were done in duplicate. Extracts of SUM149PT cells were immunoprecipitated using biotinylated iPep624 (SEQ ID NO: 5) or iPep624ΔHEX (SEQ ID NO: 18) peptides as bait, as described in methods, and elutes applied to a SDS-PAGE (10% acrylamide; Supplementary FIG. S5). Gels were stained with Coomassie brilliant blue and the select band unique to the active iPep624 (SEQ ID NO: 5) immunoprecipitates (band A1) was excised, digested with trypsin, and analyzed using a MALDI-TOF/TOF mass spectrometer (AB Sciex 4800 Plus). The identity of Band 1 was validated to be Glutamyl-prolyl tRNA synthetase (EPRS), and was found to be differentially bound by the active peptide over control by western blot experiments using an EPRS specific antibody.

Figure 11:
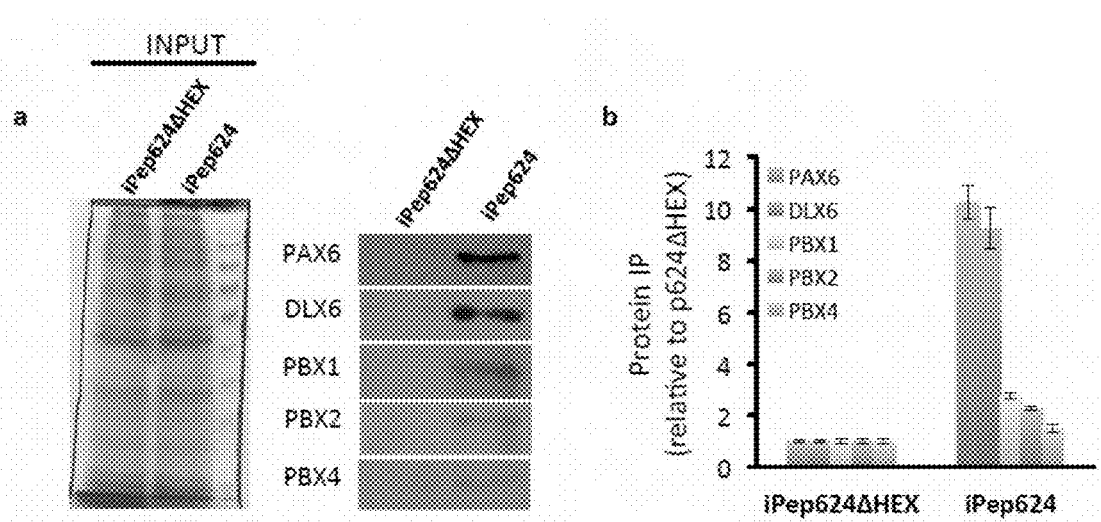

FIG. 11 The EN1 specific peptide (iPep624) (SEQ ID NO: 5) binds homeodomain-containing transcription factors (TF-HDs) from SUM149PT cell extracts in vitro. (a) Western Blot detection of several TFHDs immunoprecipitated with the EN1 specific interference peptide iPep624 (SEQ ID NO: 5), and its hexamotif mutant iPep624ΔHEX (SEQ ID NO: 18). SUM149PT total protein extracts were incubated for two hours with either the iPep624 (SEQ ID NO: 5) or iPep624ΔHEX (SEQ ID NO: 18). Elutes were processed for immunoblotting with specific antibodies for paired box 6 (PAX6), Distalless 6 (DLX6), pre-B-cell leukemia homeobox 1 (PBX1), pre-B-cell leukemia homeobox 2 (PBX2) and pre-B-cell leukemia homeobox 4 (PBX4). A representative SDSPAGE gel stained with Coomassie brilliant blue is shown to indicate equal uploading of the SUM149PT extracts used for immunodetection. (b) Quantification of the WB bands from (A) using image J. Total quantified pixels in the iPep624-bands were normalized to those detected in iPep624ΔHEX.

FIG. 12 Transcription Factors containing homeoboxes differentially expressed in breast cancer subtypes.

FIG. 13 Differentially regulated genes in SUM149PT overexpressing EN1;

FIG. 14 Gene ontology analysis of pathways significantly regulated in SUM149PT cells ectopically expressing the EN1 cDNA using the DAVID database.

Figure 15:
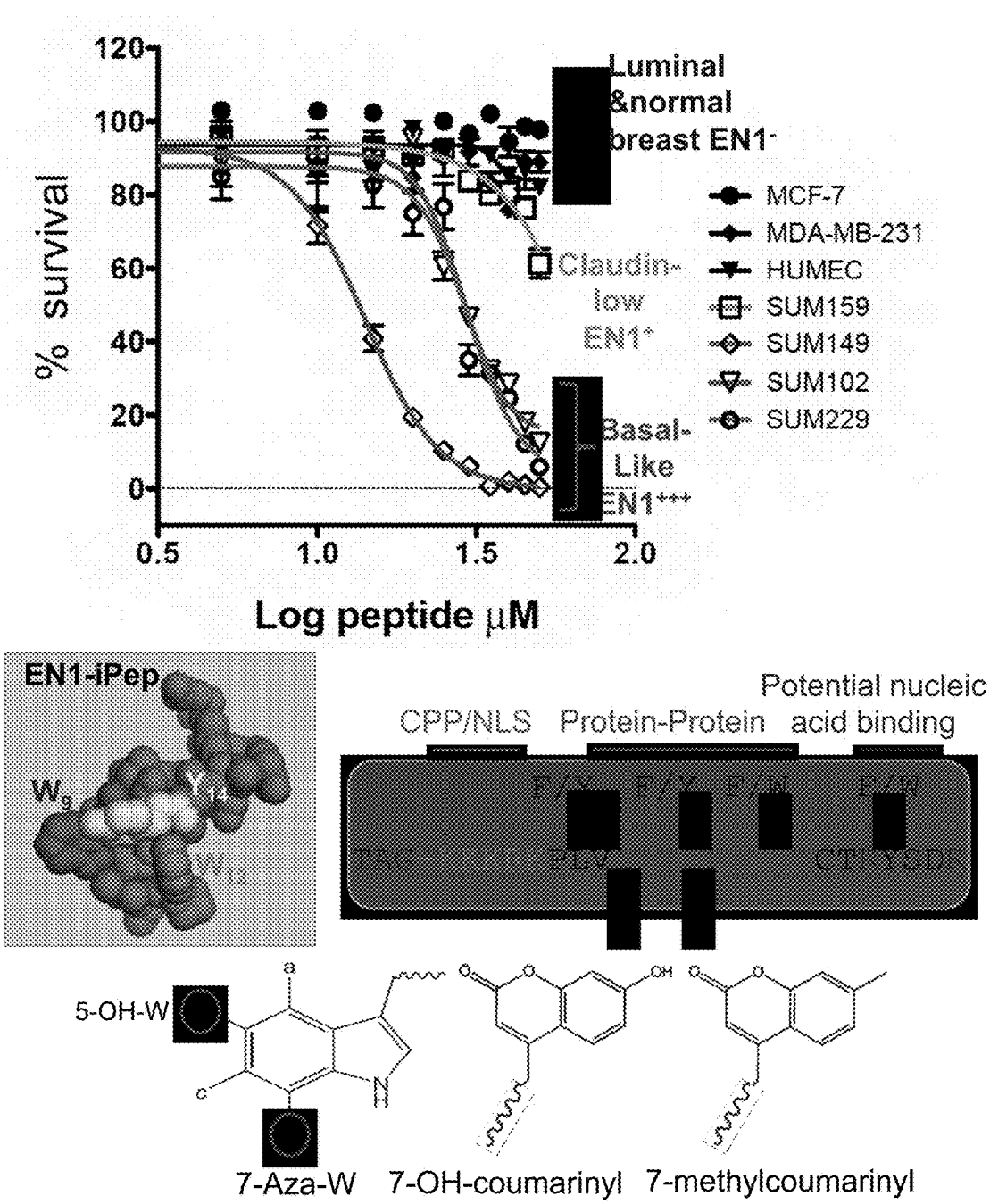

FIG. 15 Selective anti-cancer activity of the parent EN1-iPep.

Figure 16:
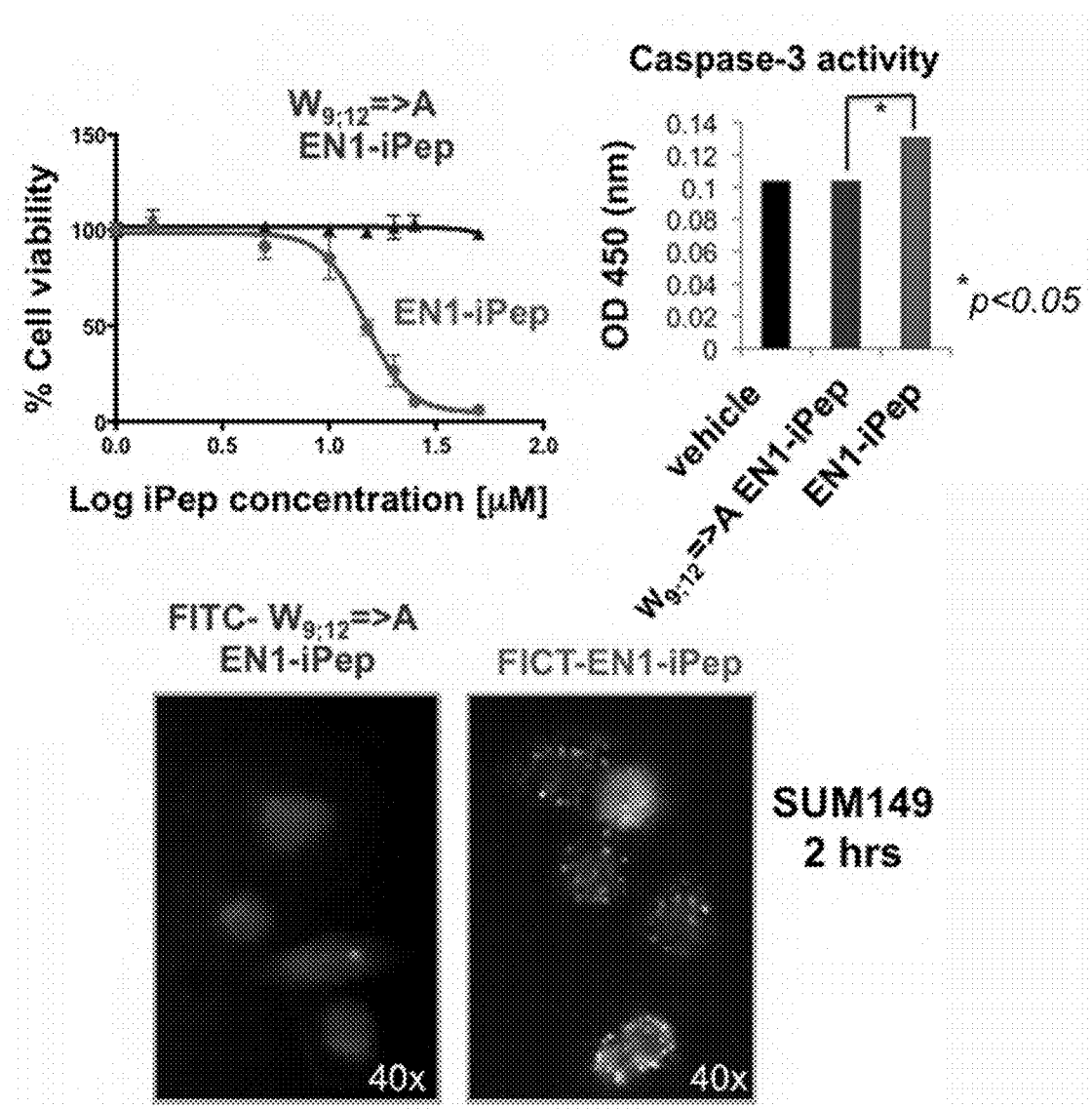

FIG. 16 The W residues in the hexamotif of the parent EN1-iPep are necessary for anticancer activity in SUM149 cells.

Figure 17:
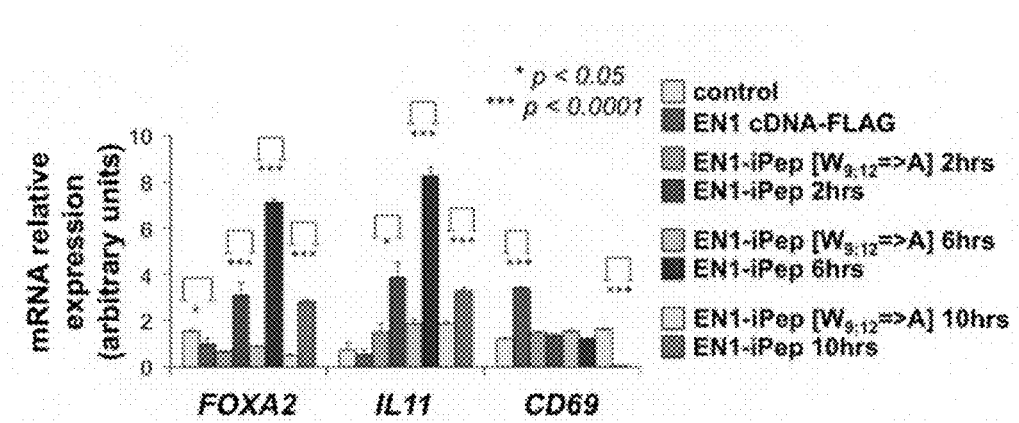

FIG. 17 EN1-iPep differentially regulates the transcription of specific mRNAs, as assessed by qRT-PCR.

FIG. 18 Assembly of PGMA-NPs for the encapsulation of EN1-iPeps and HF (top). Internalization of RhB NPs (red) in SUM149 cells releases the EN1-iPeps in ~4 hrs (green; middle). Decrease of cell viability of NPs encapsulating EN1-iPeps 12 hrs after treatment (bottom).

FIG. 19 EN1-iPep physically associates with EPRS in SUM149 cells (Top panels). A model of interaction between EN1-iPep and EPRS locking HF in the binding pocket of the enzyme (bottom). W12 is shown in cyan, HF in dark blue.

Figure 20:
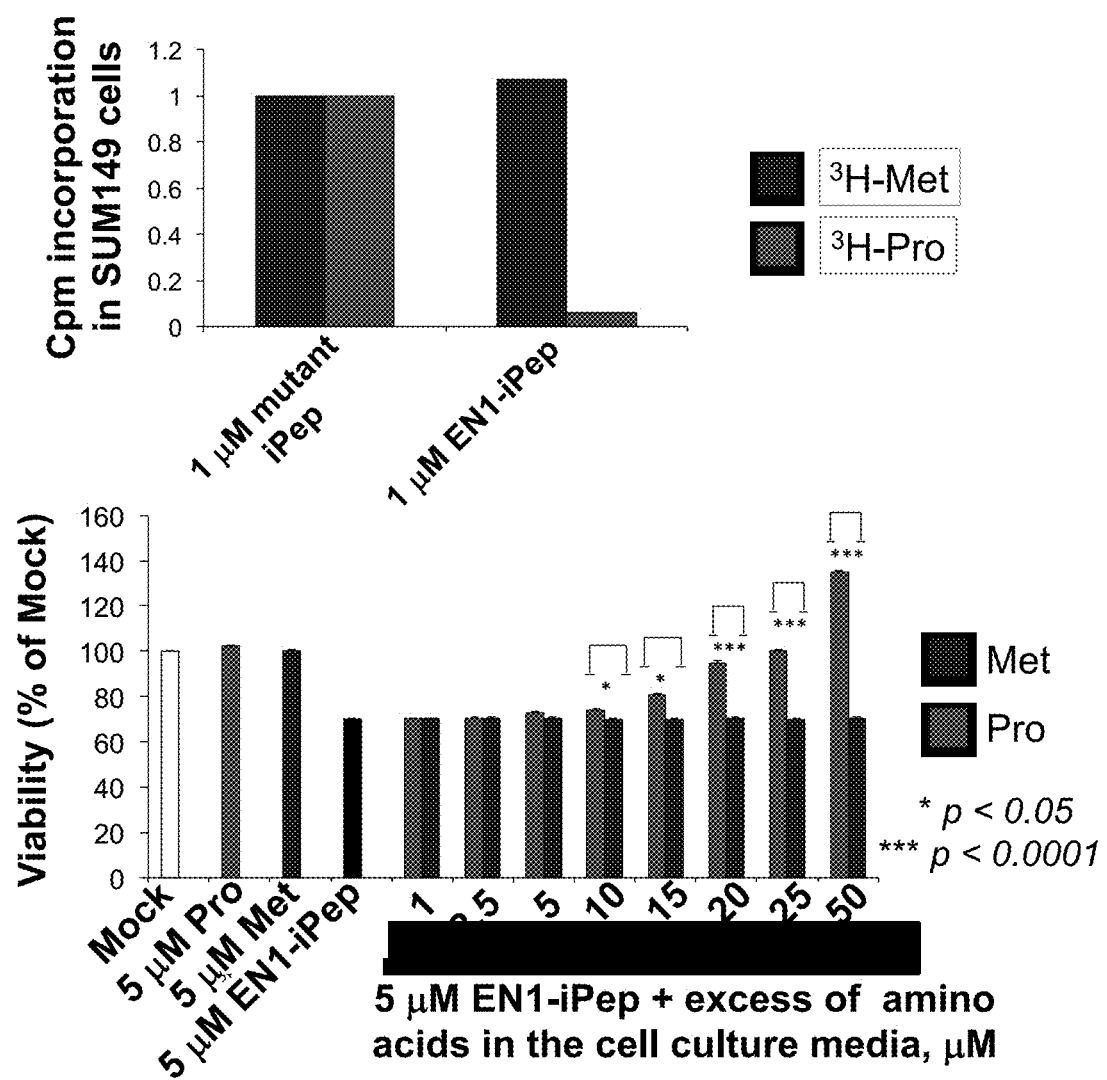

FIG. 20 EN1-iPep inhibits the incorporation of Pro in SUM149 cells (top); Rescue of cell proliferation of SUM149 cells treated with EN1-iPep and excess of Pro (bottom).

BRIEF DESCRIPTION OF THE SEQUENCES

SEQ ID NO:1 is the amino acid sequence of a first variant of the synthesized interference peptide of the invention for $TF_{HD}$ EN1 and EN2, comprising anchorage Protein-Protein and putative DNA-binding domains;

SEQ ID NO:2 is the amino acid sequence of a second variant of the synthesized interference peptide of the invention for $TF_{HD}$ EN1 and EN2;

SEQ ID NO: 3 is the amino acid sequence of a third variant of the synthesized interference peptide of the invention for $TF_{HD}$ EN1 and EN2;

SEQ ID NO: 4 is the amino acid sequence of a fourth variant of the synthesized interference peptide of the invention for $TF_{HD}$ EN1 and EN2;

SEQ ID NO: 5 is the amino acid sequence of the peptide of SEQ ID NO: 1 fused to a CPP/NLS;

SEQ ID NO: 6 is the amino acid sequence of the peptide of SEQ ID NO: 2 fused to a CPP/NLS;

SEQ ID NO: 7 is the amino acid sequence of the peptide of SEQ ID NO: 3 fused to a CPP/NLS; and SEQ ID NO: 8 is the amino acid sequence of the peptide of SEQ ID NO: 4 fused to a CPP/NLS.

DETAILED DESCRIPTION WITH REFERENCE TO THE FIGURES

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (e.g. size, concentration etc.). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

Features of the invention will now be discussed with reference to the following non-limiting description and examples.

Isolated and Purified Peptides

According to the invention the inventors have engineered interference peptides comprising a highly conserved EN1-hexamotif sequence involved in protein-protein interactions as a new, selective therapeutic strategy for inducing potent and selective apoptosis in basal-like breast tumours and other cancers overexpressing EN1 and EN2.

The present invention provides isolated and purified peptides comprising:
a. the amino acid sequences of SEQ ID NOs: 1 to 4; or
b. an amino acid sequence selected from:
  i. $PL_2V_3W_4PAWV_8Y_9C_{10}TRSDR$ (SEQ ID NO: 9); or
  wherein:
    $L_2$ is one of: L, M, or I;
    $V_3$ is one of: V or L;
    $W_4$ is one of: W, Y, or W analog;
    $V_8$ is one of: V or I;
    $Y_9$ is one of: Y or F; and
    $C_{10}$ is one of: C or S.

A peptide of the present invention may be recombinant or synthetic. A peptide of the invention may be mixed with diluents, adjuvants or carriers (including nanoparticles) that will not interfere with the intended purpose of the peptide. A peptide of the invention may also be in a substantially purified form, in which case it will generally comprise the peptide in a preparation in which at least 90%, 95%, 98% or 99% of the protein in the preparation is a peptide of the invention. The term 'peptide' as used herein may be used interchangeably with the term 'polypeptide' as referring to a chain of at least two amino acid monomers.

Cell Penetration

For peptides of the invention to interact with EPRS and PBX1A (or another transcription factor acting as an oncogene such as a PBX, Paired or Distaless family member) in an EN1 and/or EN2 expressing cell, thereby preventing interaction of EPRS to EN1 to initiate downstream signaling pathways in the cell, they must enter an EN1 and/or EN2 expressing cell.

EN1-iPep has a predominantly nuclear and perinuclear distribution with a discrete number of foci, a pattern that becomes more delocalised in the inactive W9;12=>A mutants (FIG. 16). These iPeps enter rapidly into the nucleus of tumour cells with saturation kinetics of ~90 min and with a half-life of ~8-10 hrs.

There are various systems that are known in the art that assist with the transport of peptides of the invention into an EN1 and/or EN2 expressing cell. A preferred means is for attachment of a cell penetrating peptide to the isolated and purified peptides described herein.

Therefore, the present invention provides isolated and purified peptides comprising an amino acid sequence selected from:
a. an amino acid sequences of SEQ ID NOs: 1 to 4; or
b. the amino acid sequence $PL_2V_3W_4PAWV_8Y_9C_{10}TRSDR$ (SEQ ID NO: 9), wherein:
    $L_2$ is one of: L, M, or I;
    $V_3$ is one of: V or L;
    $W_4$ is one of: W, Y, or W analog;
    $V_8$ is one of: V or I;
    $Y_9$ is one of: Y or F; and
    $C_{10}$ is one of: C or S;
attached to a means for introducing the one or more peptides into a cell, and particularly a cancer cell.

Preferably the means for introducing the one or more peptides into a cell is an additional peptide portion that assists or facilitates in the transport of the peptide of the invention into EN1 and/or EN2 expressing cells. That peptide portion may also provides some further benefit, for example, amongst others, identifying the location of a peptide within a cell or provide a nuclear localisation sequence that assists the peptide penetrating the nucleus.

KKKRKV or KKKRK are cell penetrating peptides with a nuclear localisation sequences that assists transport into a cell. Preferably, the additional peptide portion comprises one or both of the amino acids sequences KKKRKV or KKKRK. Further the cell penetrating peptide portion of a peptide of the invention may be synthesized with L amino acids to improve the half-life of the peptide in serum.

The present invention further provides isolated and purified peptides comprising an amino acid sequence selected from:
   a. an amino acid sequences of SEQ ID NOs: 5 to 8; or
   b. KKKRKPL$_2$V$_3$W$_4$PAWV$_8$Y$_9$C$_{10}$TRSDR (SEQ ID NO: 12), wherein:
      L$_2$ is one of: L, M, or 1;
      V$_3$ is one of: V or L;
      W$_4$ is one of: W, Y, or W analog;
      V$_8$ is one of: V or I;
      Y$_9$ is one of: Y or F; and
      C$_{10}$ is one of: C or S.

The peptides of the invention can remove pro-survival pathways and enable apoptotic pathways leading to the death of an EN1 and/or EN2 expressing cell in which they are introduced. Preferably, the EN1 and/or EN2 expressing cell is a cancer cell and these cancer cells are the target for treatment with the peptides of the invention. However, in the treatment of an EN1 and/or EN2 expressing cancer in a subject, it will not be desirable to have peptides of the invention introduced into other EN1 and/or EN2 expressing cells which carry out a normal, important role in the subject. EN1 is expressed in the adult brain, in dopaminergic neural progenitors and dopaminergic neurons in the cerebellum. Strong EN2 expression is also detected in the adult human cerebellum.

Peptide Variants

Functional peptide variants are peptides of the invention which interact with EPRS thereby preventing interaction of EN1 to EPRS, or EN2 to PBX1A, or EN1 and/or EN2 to other transcription factors that can act as oncogenes in tissues such as the mammary gland, for example, but not limited to PBX, Paired and Distaless family members including PBX1, PBX2, PBX4 PAX6 and DLX6. Such variants include the above recited sequences with deletions, insertions, inversions, repeats, and type substitutions. Guidance concerning which amino acid changes are likely to be phenotypically silent can be found in Bowie, J. U., et al, "Deciphering the Message in Protein Sequences: Tolerance to Amino Acid Substitutions," Science 247:1306-1310 (1990).

Thus, a variant peptide of the present invention as described herein may be: (i) one in which one or more of the amino acid residues are substituted with a conserved or non-conserved amino acid residue (preferably a conserved amino acid residue) and such substituted amino acid residue may or may not be one encoded by the genetic code, (ii) one in which one or more of the amino acid residues includes a substituent group, (iii) one in which the peptide is fused with another compound, such as a compound to increase the half-life of the peptide (for example, polyethylene glycol or polypropylene glycol), or (iv) one in which the additional amino acids, such as a leader, signal or secretory sequence or a sequence which is employed for purification of the peptide sequence are fused to the mature peptide. Such fragments, derivatives and analogs are deemed to be within the scope of those skilled in the art from the teachings herein.

In a preferred form, peptide variants for use in the clinic are developed according to the following method. First a detailed mutational study of currently most active ("parent") EN1-iPep is carried out to determine the minimal epitopes necessary for selective anti-cancer activity. Systematic single amino acid alanine scans are then performed in the EN1-iPep followed by nested C-terminal deletions (FIG. 15). In addition, [W$_{9/12}$=>F/Y] and [Y$_{14118}$=>F/W] mutations and incorporation of functionalized unnatural amino acids (e.g. 2-OH—W, 7-Aza-W, 7-OH-coumarinyl) are carried to model the iPeps in their binding pockets.

As indicated above, variants of the peptides of the present invention may include one or more amino acid substitutions, deletions or additions, either from natural mutations or human manipulation. The particular replacements may be determined by a skilled person as detailed more fully hereunder. However, changes are preferably of a minor nature, such as conservative amino acid substitutions that do not significantly affect the folding or activity of the peptide (see for example the table hereunder). Amino acids in the same block in the second column and preferably in the same line in the third column may be substituted for each other:

| ALIPHATIC | Non-polar | G A P |
|---|---|---|
|  |  | I L V |
|  | Polar - uncharged | C S T M |
|  |  | N Q |
|  | Polar - charged | D E |
|  |  | K R |
| AROMATIC |  | H F W Y |

Amino acids in the peptides of the present invention that are essential for function can be identified by methods known in the art, such as site directed mutagenesis or alanine-scanning mutagenesis. The latter procedure introduces single alanine mutations at every residue in the molecule. In an Alanine scan, individual peptides are prepared in which each residue "X" of the wild type full-length peptide is systematically changed to Ala by conventional peptide synthesis. The resulting mutant molecules can then tested for biological activity such as interaction with EPRS (EN1 interacting molecule) or PBX1A (EN2 interacting molecule), and ability to enter cells such as EN1 and/or EN2 expressing cancer cells. Nuclear magnetic resonance or photoaffinity labelling may also be used when developing functional variants. Alternatively, synthetic peptides corresponding to candidate functional variants may be produced and their ability to display one or more activities of the peptides assessed in vitro or in vivo.

Peptide variants of the present invention can also be prepared as libraries comprising sequences according to SEQ ID NOs: 1 to 8. Phage display can also be effective in identifying variants useful according to the invention. Briefly, a phage library is prepared (using e.g. m13, fd, or lambda phage), displaying inserts from 4 to about 80 amino acid residues using conventional procedures. The inserts may represent, for example, a biased degenerate array or may completely restrict the amino acids at one or more positions (e.g., for a library based on a peptide of any one of SEQ ID NOs: 1 to 8). One then can select phage-bearing inserts that have a relevant biological activity of the peptide of the invention, for example, interacting with EPRS at the site of interaction between EN1 and EPRS in an EN1 expressing cancer cell. This process can be repeated through several cycles of reselection of phage. Repeated rounds lead to enrichment of phage bearing particular sequences. DNA sequence analysis can be conducted to identify the sequences of the expressed polypeptides. The minimal linear portion of the sequence that confers the relevant activity can be determined. One can repeat the procedure using a biased library containing inserts containing part or the entire minimal linear portion plus one or more additional degenerate residues upstream or downstream thereof.

Peptides of the invention, including variant peptides, can be tested for retention of any of the given activity. For example, a peptide can be tested for in vitro properties using transient transfection assays with a responsive reporter that assesses the ability of the peptide to interact with EPRS or PBX1A in an EN1 and/or EN2 expressing cancer cell.

Preferred variant peptides of the present invention comprise an amino acid sequence that is at least 70-80% identical, more preferably at least 90% or 95% identical, still more preferably at least 96%, 97%, 98% or 99% identical to any one of SEQ ID NOs: 1 to 8, provided the variant peptides can bind the EPRS or PBX1A of an EN1 and/or EN2 expressing cancer cell or another transcription factor acting as an oncogene.

By a peptide having an amino acid sequence at least, for example, 90% "identical" to a reference amino acid sequence of a peptide of the invention it is intended that the amino acid sequence of the peptide is identical to the reference sequence except that the polypeptide sequence may include up to one amino acid alteration per each 10 amino acids of the reference peptide. In other words, to obtain a peptide having an amino acid sequence at least 90% identical to a reference amino acid sequence, up to 10% of the amino acid residues in the reference sequence may be deleted or substituted with another amino acid, or a number of amino acids up to 10% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

In general, a peptide of the present invention can be synthesized directly or obtained by chemical or mechanical disruption of larger molecules, fractioned and then tested for one or more activity of the peptide. Functional variants may also be produced by Northern blot analysis of total cellular RNA followed by cloning and sequencing of identified bands derived from different tissues/cells, or by PCR analysis of such RNA also followed by cloning and sequencing. Thus, synthesis or purification of a large number of functional variants is possible using the information contained herein.

It may be desirable to use derivatives of peptides of the invention that are conformationally constrained. Conformational constraint refers to the stability and preferred conformation of the three-dimensional shape assumed by a peptide. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure.

The active conformation of the peptide may be stabilized by a covalent modification, such as cyclization or by incorporation of gamma-lactam or other types of bridges. For example, side chains can be cyclized to the backbone to create a L-gamma-lactam moiety on each side of the interaction site. Cyclization also can be achieved, for example, by formation of cysteine bridges, coupling of amino and carboxy terminal groups of respective terminal amino acids, or coupling of the amino group of a Lys residue or a related homolog with a carboxy group of Asp, Glu or a related homolog. Coupling of the alpha-amino group of a peptide of the invention with the epsilon-amino group of a lysine residue, using iodoacetic anhydride, can be also undertaken.

Another approach is to include a metal-ion complexing backbone in the structure of a peptide of the invention. Typically, the preferred metal-peptide backbone is based on the requisite number of particular coordinating groups required by the coordination sphere of a given complexing metal ion. In general, most of the metal ions that may prove useful have a coordination number of four to six. The nature of the coordinating groups in the peptide chain includes nitrogen atoms with amine, amide, imidazole, or guanidino functionalities; sulphur atoms of thiols or disulfides; and oxygen atoms of hydroxy, phenolic, carbonyl, or carboxyl functionalities. In addition, the peptide chain or individual amino acids can be chemically altered to include a coordinating group, such as for example oxime, hydrazino, sulfhydryl, phosphate, cyano, pyridino, piperidino, or morpholino. The peptide construct can be either linear or cyclic, however a linear construct is typically preferred. One example of a small linear peptide is Gly-Gly-Gly-Gly that has four nitrogens (an $N_4$ complexation system) in the backbone that can complex to a metal ion with a coordination number of four.

Other methods for identifying variants of peptides of the invention herein rely upon the development of amino acid sequence motifs to which potential epitopes may be compared. Each motif describes a finite set of amino acid sequences in which the residues at each (relative) position may be (a) restricted to a single residue, (b) allowed to vary amongst a restricted set of residues, or (c) allowed to vary amongst all possible residues. For example, a motif might specify that the residue at a first position may be any one of valine, leucine, isoleucine, methionine, or phenylalanine; that the residue at the second position must be histidine; that the residue at the third position may be any amino acid residue; that the residue at the fourth position may be any one of the residues valine, leucine, isoleucine, methionine, phenylalanine, tyrosine or tryptophan; that the residue at the fifth position must be lysine, and so on.

Thus, the present invention also provides methods for identifying functional variants of peptides of the invention. In general, the methods include selecting a peptide of the invention. Then a first amino acid residue of the peptide is mutated to prepare a variant peptide. In one embodiment, the amino acid residue can be selected and mutated as indicated by a computer model of peptide conformation. Peptides bearing mutated residues that maintain a similar conformation (e.g. secondary structure) can be considered potential functional variants that can be tested for function using the assays described herein. Any method for preparing variant peptides can be employed, such as synthesis of the variant peptide, recombinantly producing the variant peptide using a mutated nucleic acid molecule, and the like. The properties of the variant peptide in relation to the peptides described previously are then determined according to standard procedures as described herein.

Variants of peptides of the invention prepared by any of the foregoing methods can be sequenced, if necessary, to determine the amino acid sequence and thus deduce the nucleotide sequence which encodes such variants.

The present invention also includes non-peptide mimetics of peptides of the invention. A wide variety of techniques may be used to elucidate the precise structure of a peptide. These techniques include amino acid sequencing, x-ray crystallography, mass spectroscopy, nuclear magnetic resonance spectroscopy, computer-assisted molecular modelling, peptide mapping, and combinations thereof. Structural analysis of a peptide provides a large body of data that comprise the amino acid sequence of the peptide as well as the three-dimensional positioning of its atomic components. From this information, non-peptide peptidomimetics may be designed that have the required chemical functionalities for therapeutic activity but are more stable, for example less susceptible to biological degradation.

Thus, variant peptides of the present invention also include mimetics. Nonpeptide analogs of peptides of the invention, such as those that provide a stabilized structure or lessened biodegradation, are within the scope of the present invention. Peptide mimetic analogs can be prepared based on a selected peptide of the invention by replacement of one or more residues by nonpeptide moieties. Preferably, the nonpeptide moieties permit the peptide to retain its natural conformation, or stabilize a preferred, e.g., bioactive, conformation such as a conformation able to bind the site on EPRS which interacts with EN1. Thus, the present invention also provides for the use of a peptide of the invention described herein for designing a mimetic thereof such as a non-peptide peptidomimetic.

Preferably, the peptides of the invention are non-hydrolyzable in that the bonds linking the amino acids of the peptides are less readily hydrolyzed than peptide bonds formed between L-amino acids. To provide such peptides, one may select isolated peptides from a library of non-hydrolyzable peptides, such as peptides containing one or more D-amino acids or peptides containing one or more non-hydrolyzable peptide bonds linking amino acids.

Alternatively, one can select peptides that are optimal for a preferred function in suitable assay systems and then modify such peptides as necessary to reduce the potential for hydrolysis by proteases. For example, to determine the susceptibility to proteolytic cleavage, peptides may be labelled and incubated with cell extracts or purified proteases and then isolated to determine which peptide bonds are susceptible to proteolysis, e.g., by sequencing peptides and proteolytic fragments. Alternatively, potentially susceptible peptide bonds can be identified by comparing the amino acid sequence of an isolated peptide with the known cleavage site specificity of a panel of proteases. Based on the results of such assays, individual peptide bonds that are susceptible to proteolysis can be replaced with non-hydrolyzable peptide bonds by in vitro synthesis of the peptide.

Many non-hydrolyzable peptide bonds are known in the art, along with procedures for synthesis of peptides containing such bonds. Non-hydrolyzable bonds include -psi[CH$_2$ NH]— reduced amide peptide bonds, -psi[COCH$_2$]—ketomethylene peptide bonds, -psi[CH(CN)NH]—(cyanomethylene)amino peptide bonds, -psi[CH$_2$ CH(OH)]—hydroxyethylene peptide bonds, -psi[CH$_2$ O]—peptide bonds, and -psi[CH$_2$ S]—thiomethylene peptide bonds.

Likewise, various changes may be made including the addition of various side groups that do not affect the manner in which the peptides function, or which favourably affect the manner in which the peptides function. Such changes may involve adding or subtracting charge groups, substituting amino acids, adding lipophilic moieties that do not affect binding but that affect the overall charge characteristics of the molecule facilitating a specific outcome with a physiological benefit. For each such change, no more than routine experimentation is required to test whether the molecule functions according to the invention. One simply makes the desired change or selects the desired peptide and applies it in a fashion as described in detail herein.

The peptides of the invention may also be linked to a variety of polymers, such as polyethylene glycol (PEG) and polypropylene glycol (PPG). Replacement of naturally occurring amino acids with a variety of uncoded or modified amino acids such as D-amino acids and N-methyl amino acids may also be used to modify peptides. Another approach is to use bifunctional crosslinkers, such as N-succinimidyl 3-(2 pyridyldithio) propionate, succinimidyl 6-[3-(2 pyridyldithio)propionamido]hexanoate, and sulfosuccinimidyl 6-[3-(2 pyridyldithio) propionamido]hexanoate. To further protect the iPeps and enhance their half-life they may be chemically modified such as by incorporation of D-amino acids isomers.

The present peptide or analogues, such as those recited infra may be derivatized by the attachment of one or more chemical moieties to the peptide sequence. Chemical modification of biologically active peptides provides advantages under certain circumstances, such as increasing the stability and circulation time of the therapeutic peptides, decreasing immunogenicity and to enhance bioavailability and/or to enhance efficacy and/or specificity. See, U.S. Pat. No. 4,179,337, Davis et al., issued Dec. 18, 1979. For a review, see Abuchowski et al., in Enzymes as Drugs. (J. S. Holcerberg and J. Roberts, eds. pp. 367 383 (1981)).

Peptide Modifications

The present invention further comprises peptides of the invention as described herein, said peptides modified so that they can only be introduced into, or expressed in selected cells. These selected cells may be of one or more cell-types, for example, in one non-limiting example, basal-like tumor cells. Said modification of the peptides of the invention will preferably prevent introduction into, or expression in normal cells, for example, non-cancer cells in the cerebellum of a subject and particularly a human subject, including dopaminergic neural progenitors and dopaminergic neurons. Said modifications to the peptides of the invention will be known in the art and will include, but will not be limited to, chemical modifications. In one non-limiting example, modifications on peptides of the invention will identify cell surface markers on cells in which the peptides are to be introduced, therein limiting introduction of peptides of the invention to only cells having said cell surface markers. In another example, modifications on peptides of the invention will prevent movement of the peptides into the brain of a subject. Preferably, modifications on the peptides of the invention prevent movement of the peptides through the blood-brain barrier.

The present invention further comprises methods of introducing peptides of the invention as described herein into selected cells. The selected cells may be of one or more cell-types, for example, in one non-limiting example, basal-like tumor cells. Various techniques for cell-specific peptide introduction or expression will be known in the art. One non-limiting example includes tumor-specific nanoparticles which target tumor cells, for example, basal-like breast tumor cells, to selectively introduce peptides of the invention only into tumor cells. Specific cell-surface markers may be used to identify cells into which peptides of the invention are introduced. Such methods may be used to prevent peptides of the invention entering the brain, for example, preventing the peptides from passing through the blood-brain barrier.

Peptide variants of the present invention also include fusion to further peptides, for example, where an additional peptide sequence is fused to a peptide of the invention to aid in extraction and purification. Examples of additional fusion peptide partners include glutathione-S-transferase (GST), hexahistidine, GAL4 (DNA binding and/or transcriptional activation domains) and β-galactosidase. It may also be convenient to include a proteolytic cleavage site between the additional peptide partner and the peptide of the invention to allow removal of additional peptide sequences. Preferably the additional peptide will not hinder binding of the peptide of the invention to the EN1 interacting molecule such as EPRS.

A peptide of the present invention may also include conjugated peptides. In this regard, a peptide may be modified by attachment of a moiety (e.g. a cell penetrating peptide, a fluorescent, radioactive, or enzymatic label, or an unrelated sequence of amino acids) that does not correspond to a portion of the peptide in its native state. Thus, a peptide of the present invention may comprise chimeric peptides comprising an additional fusion of a peptide of the invention with another peptide. For example, a peptide capable of targeting the peptide of the invention to a cell type or tissue type, enhancing stability of the peptide of the invention under assay conditions, or providing a detectable moiety, such as green fluorescent protein. A moiety fused to a peptide of the invention or a fragment thereof also may provide means of readily detecting the peptide of the invention, for example, by immunological recognition or by fluorescent labelling such as green fluorescent protein. Purified peptides of the invention include peptides isolated by methods including, but are not limited to, immunochromotography, HPLC, size-exclusion chromatography, ion-exchange chromatography and immune-affinity chromatography.

A peptide of the invention can be conjugated by well-known methods, including bifunctional linkers, formation of a fusion peptide, and formation of biotin/streptavidin or biotin/avidin complexes by attaching either biotin or streptavidin/avidin to the peptide and the complementary molecule. Depending upon the nature of the reactive groups in a peptide of the invention and a targeting agent, a conjugate can be formed by simultaneously or sequentially allowing the functional groups of the above-described components to react with one another. Numerous art-recognized methods for forming a covalent linkage can be used. See, e.g., March, J., Advanced Organic Chemistry, 4th Ed., New York, N.Y., Wiley and Sons, 1985), pp. 326-1120.

In general, conjugated fusion peptides of the invention can be prepared by using well-known methods for forming amide, ester or imino bonds between acid, aldehyde, hydroxy, amino, or hydrazo groups on the respective conjugated peptide components. As would be apparent to one of ordinary skill in the art, reactive functional groups that are present in the amino acid side chains of the fusion peptide preferably are protected, to minimize unwanted side reactions prior to coupling the fusion peptide to the derivatizing agent and/or to the extracellular agent. As used herein, "protecting group" refers to a molecule which is bound to a functional group and which may be selectively removed therefrom to expose the functional group in a reactive form. Preferably, the protecting groups are reversibly attached to the functional groups and can be removed therefrom using, for example, chemical or other cleavage methods. Thus, for example, fusion peptides of the invention can be synthesized using commercially available side-chain-blocked amino acids (e.g., FMOC-derivatized amino acids from Advanced Chemtech Inc., Louisville, Ky.). Alternatively, the peptide side chains can be reacted with protecting groups after peptide synthesis, but prior to the covalent coupling reaction. In this manner, conjugated fusion peptides of the invention can be prepared in which the amino acid side chains do not participate to any significant extent in the coupling reaction of the peptide to the other agent, such as a cell-type-specific targeting agent.

If a peptide of the invention does not have a free amino- or carboxyl-terminal functional group that can participate in a coupling reaction, such a group can be introduced, e.g., by introducing a cysteine (containing a reactive thiol group) into the peptide by synthesis or site directed mutagenesis. Disulfide linkages can be formed between thiol groups in, for example, the peptide and the targeting compound. Alternatively, covalent linkages can be formed using bifunctional cross linking agents, such as bismaleimidohexane (which contains thiol-reactive maleimide groups and which forms covalent bonds with free thiols). See also the Pierce Co. Immunotechnology Catalogue and Handbook Vol. 1 for a list of exemplary homo- and hetero-bifunctional cross linking agents, thiol-containing amines and other molecules with reactive groups.

For peptides of the invention that exhibit reduced activity in a conjugated form, the covalent bond between the peptide of the invention and its conjugate is selected to be sufficiently labile (e.g., to enzymatic cleavage) so that it is cleaved following transport to its target, thereby releasing the free peptide at the target. Biologically labile covalent linkages, e.g., imino bonds, and "active" esters can be used to form prodrugs where the covalently coupled peptides are found to exhibit reduced activity in comparison to the activity of the peptide of the invention alone.

It will be appreciated that the amino acids in a peptide of the invention that are required for activity may be incorporated into larger fusion proteins and still maintain their function.

Selective Binding Agent

As used herein, the term "selective binding agent" refers to a molecule that has specificity for peptides of the invention described herein. Suitable selective binding agents include, but are not limited to, antibodies and derivatives thereof, polypeptides and small molecules. Suitable selective binding agents may be prepared using methods known in the art. An exemplary selective binding agent is capable of binding a portion of a peptide of the invention. Such binding agents can be utilised to determine the presence of peptides of the invention in tissue or individual cells and determine binding activity and/or localisation with other molecules.

Selective binding agents such as antibodies and antibody fragments that bind peptides of the invention include monospecific polyclonal, monoclonal (MAbs), recombinant, chimeric, humanized such as CDR-grafted, human, single chain, and/or bispecific, as well as fragments, variants or derivatives thereof. Antibody fragments include those portions of the antibody that bind to an epitope on the peptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies generally are produced in animals (e.g., rabbits or mice) by means of multiple subcutaneous or intraperitoneal injections of the peptide and an adjuvant. It may be useful to conjugate the peptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for antibody titre.

Monoclonal antibodies are produced using any method that provides for the production of antibody molecules by continuous cell lines in culture. Examples of suitable methods for preparing monoclonal antibodies include the hybridoma methods of Kohler et al., Nature, 256:495-497 (1975) and the human B-cell hybridoma method, Kozbor, J. Immunol., 133:3001 (1984); (1984) and Brodeur et al., Monoclonal Antibody Production Techniques and Applications, pp. 51-63 (Marcel Dekker, Inc., New York, 1987). Also provided by the invention are hybridoma cell lines that produce monoclonal antibodies reactive with peptides herein.

In another embodiment, a monoclonal antibody that binds a peptide of the invention is a "humanized" antibody. Methods for humanizing non-human antibodies are well known in the art. Generally, a humanized antibody has one or more amino acid residues introduced into it from a source that is non-human. Humanization can be performed, for example, using methods described in the art (Jones et al., Nature 321:522-525 (1986); Riechmann et al., Nature, 332: 323-327 (1988); Verhoeyen et al., Science, 239:1534-1536 (1988)), by substituting at least a portion of a rodent complementarity-determining region (CDR) for the corresponding regions of a human antibody.

Using transgenic animals (e.g., mice) that are capable of producing a repertoire of human antibodies in the absence of endogenous immunoglobulin production, such antibodies are produced by immunization with a peptide antigen (i.e., having at least 6 contiguous amino acids), optionally conjugated to a carrier. In one method, such transgenic animals are produced by incapacitating the endogenous loci encoding the heavy and light immunoglobulin chains therein, and inserting loci encoding human heavy and light chain proteins into the genome thereof. Partially modified animals, that is, those having less than the full complement of modifications, are then cross-bred to obtain an animal having all of the desired immune system modifications. When administered an immunogen, these transgenic animals produce antibodies with human (rather than e.g., murine) amino acid sequences, including variable regions that are immunospecific for these antigens. See PCT application nos. PCT/US96/05928 and PCT/US93/06926. Additional methods are described in U.S. Pat. No. 5,545,807, PCT application nos. PCT/US91/245, PCT/GB89/01207, and in EP 546073B1 and EP 546073A1. Human antibodies may also be produced by the expression of recombinant DNA in host cells or by expression in hybridoma cells as described herein.

In an alternative embodiment, human antibodies can be produced from phage-display libraries (Hoogenboom et al., J. Mol. Biol., 227:381 (1991); (1991) and Marks et al., J. Mol. Biol., 222:581 (1991)). These processes mimic immune selection through the display of antibody repertoires on the surface of filamentous bacteriophage, and subsequent selection of phage by their binding to an antigen of choice. One such technique is described in PCT Application No. PCT/US98/17364, which describes the isolation of high affinity and functional agonistic antibodies.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The antibodies to peptides of the invention may be employed in any known assay method, such as competitive binding assays, direct and indirect sandwich assays, and immunoprecipitation assays (Sola, Monoclonal Antibodies: A Manual of Techniques, pp. 147-158 (CRC Press, Inc., 1987)) for the detection and quantitation of peptides. The antibodies will bind peptides with an affinity that is appropriate for the assay method being employed.

For diagnostic applications, in certain embodiments, antibodies may be labelled with a detectable moiety. The detectable moiety can be any one that is capable of producing, either directly or indirectly, a detectable signal. For example, the detectable moiety may be a radioisotope, such as $^3$H, $^{14}$C, $^{32}$P, $^{35}$S, or $^{125}$I; a fluorescent or chemiluminescent compound, such as fluorescein isothiocyanate, rhodamine, or luciferin; or an enzyme, such as alkaline phosphatase, β-galactosidase, or horseradish peroxidase.

Competitive binding assays rely on the ability of a labelled standard (e.g., a peptide described herein or an immunologically reactive portion thereof) to compete with the test sample (a candidate polypeptide) for binding with a limited amount of antibody. The amount of the candidate polypeptide in the test sample is inversely proportional to the amount of standard that becomes bound to the antibody. To facilitate determining the amount of standard that becomes bound, the antibodies typically are insolubilized before or after the competition, so that the standard and candidate polypeptide that are bound to the antibodies may conveniently be separated from the standard and candidate polypeptide which remain unbound.

Sandwich assays typically involve the use of two antibodies, each capable of binding to a different immunogenic portion, or epitope, of the peptide to be detected and/or quantitated. In a sandwich assay, the test sample (analyte) is typically bound by a first antibody that is immobilized on a solid support, and thereafter a second antibody binds to the analyte, thus forming an insoluble three-part complex. The second antibody may itself be labelled with a detectable moiety (direct sandwich assays) or may be measured using an anti-immunoglobulin antibody that is labelled with a detectable moiety (indirect sandwich assays). For example, one type of sandwich assay is an enzyme-linked immunosorbent assay (ELISA), in which case the detectable moiety is an enzyme.

The selective binding agents, including antibodies, are also useful for in vivo imaging of administered peptides of the invention. An antibody labelled with a detectable moiety may be administered to an animal, preferably into the bloodstream, and the presence and location of the labelled antibody in the host is assayed. The antibody may be labelled with any moiety that is detectable in an animal, whether by nuclear magnetic resonance, radiology, or other detection means known in the art.

The invention also relates to a kit comprising selective binding agents (such as antibodies) and other reagents useful for detecting the levels and localisation of the peptides described herein in biological samples. Such reagents may include, a detectable label, blocking serum, positive and negative control samples, and detection reagents.

In particular, antibodies may be used to detect peptides of the invention present in biological samples. Suitable samples are preferably from tumours or cancer cells but may also include extracts of tissues such as brain, skin, breast, ovary, lung, colon, pancreas, testes, liver, muscle, prostate and bone tissues. Such antibodies of the invention may be bound to a solid support and/or packaged into kits in a suitable container along with suitable reagents, controls, instructions and the like.

Biomarkers

In another aspect, the present invention provides a use for EN1 as a biomarker for identifying EN1-expressing cancer cells. More particularly, EN1 can be used as a biomarker for cancer cells including basal-like breast cancer cells, ovarian cancer cells, medulloblastomas or other tumors originating in the cerebellum, or salivary gland adenoid cystic carcinoma cells. These cells are preferably human cells.

The cells may be removed from a subject before EN1 is used as a biomarker to detect EN1-expressing cancer cells. Alternatively, cells or tissue within a subject may be assayed for the presence of EN1-expressing cancer cells.

The present invention also provides a method for identifying basal-like breast cancer cells in a subject comprising the steps of:

(i) quantifying the levels of expression of EN1 in cells that are in or have been removed from a subject; and
(ii) comparing the expression levels to EN1 expression levels of known basal-like breast cancer cells.

The skilled person will be aware of the various available techniques for assaying cells and tissues of a subject for the expression of EN1. Such techniques may comprise use of selective binding agents such as those described above. Preferably, EN1 expression can be detected by ELISA on nipple aspirates or milk as a way to diagnose basal-like breast cancer.

Polynucleotides

The present invention also provides an isolated polynucleotide encoding a peptide of the present invention as described herein including peptides comprising SEQ ID NOs. 1 to 8. It will be understood by a skilled person that due to the degeneracy of the amino acid code, numerous different polynucleotides can encode the same peptide as a result of the degeneracy of the genetic code. In addition, it is to be understood that skilled persons may, using routine techniques, make nucleotide substitutions that do not affect the peptide sequence encoded by the polynucleotides of the invention to reflect the codon usage of any particular host organism in which the polypeptides of the invention are to be expressed.

Polynucleotides of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand. They may also be polynucleotides that include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention.

Where the polynucleotide of the invention is double-stranded, both strands of the duplex, either individually or in combination, are encompassed by the present invention. Where the polynucleotide is single-stranded, it is to be understood that the complementary sequence of that polynucleotide is also included within the scope of the present invention.

Reference to "isolated" polynucleotide(s) means a polynucleotide, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution.

Isolated RNA molecules include in vivo or in vitro RNA transcripts of the DNA molecules of the present invention. Isolated peptides of the present invention further include such molecules produced synthetically.

The present invention also provides isolated polynucleotides that selectively hybridize with at least a portion of a polynucleotide of the present invention. As used herein to describe nucleic acids, the term "selectively hybridize" excludes the occasional randomly hybridizing nucleic acids under at least moderate stringency conditions. Thus, selectively hybridizing polynucleotides preferably hybridize under at least moderate stringency conditions and more preferably under high stringency conditions. The hybridising polynucleotides may be used, for example, as probes or primers for detecting the presence of polynucleotides encoding peptides of the invention, for example, cDNA or mRNA.

A nucleic acid molecule is "hybridizable" to another nucleic acid molecule, such as a cDNA, genomic DNA, or RNA, when a single-stranded form of the nucleic acid molecule can anneal to the other nucleic acid molecule under the appropriate conditions of temperature and solution ionic strength. The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived and are known to those skilled in the art. For hybridization with shorter nucleic acids, i.e., oligonucleotides, the position of mismatches becomes more important, and the length of the oligonucleotide determines its specificity. Preferably a minimum length for a hybridizable nucleic acid is at least about 10 nucleotides; more preferably at least about 15 nucleotides; most preferably the length is at least about 20, 30 or 40-70 nucleotides.

Of course, a polynucleotide which hybridizes only to a poly A sequence (such as a 3' terminal poly(A) tail of a polynucleotide of the present invention), or to a complementary stretch of T (or U) residues, would not be included as a selectively hybridizable polynucleotide of the invention, since such a polynucleotide would hybridize to any nucleic acid molecule containing a poly (A) stretch or the complement thereof (e.g., practically any double-stranded cDNA clone).

Using the nucleic acid sequences taught herein and relying on cross-hybridization, one skilled in the art can identify polynucleotides in other species that encode peptides of the invention. If used as primers, the invention provides compositions including at least two nucleic acids that selectively hybridize with different regions of the target nucleic acid so as to amplify a desired region. Depending on the length of the probe or primer, the target region can range between 70% complementary bases and full complementarity.

The selectively hybridisable polynucleotides described herein or more particularly portions thereof can be used to detect the nucleic acid of the present invention in samples by methods such as the polymerase chain reaction, ligase chain reaction, hybridization, and the like. Alternatively, these sequences can be utilized to produce an antigenic protein or protein portion, or an active protein or protein portion.

In addition, portions of the selectively hybridisable polynucleotides described herein can be selected to selectively hybridize with homologous polynucleotides in other organisms. These selectively hybridisable polynucleotides can be used, for example, to simultaneously detect related sequences for cloning of homologues of the peptides of the present invention.

As indicated above, the polynucleotides of the present invention that encode a peptide of the present invention include, but are not limited to, those peptides encoded by the amino acid sequences of SEQ ID No: 1 to 8. Rather the polynucleotides of the present invention may comprise the coding sequence for the peptides and additional sequences, such as those encoding a leader or secretory sequence, such as a pre-, or pro- or prepro-protein sequence; the coding sequence of the peptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example ribosome binding and stability of mRNA; an additional coding sequence which codes for additional amino acids, such as those which provide additional functionalities. Preferably, the additional sequence codes for the KKKRKV (SEQ ID NO: 10) or KKKRK (SEQ ID NO: 11) cell penetrating/nuclear localisation sequence portions of the peptides of SEQ ID NO: 5 to 8. Polynucleotides according to the present invention also include those encoding a peptide lacking the N terminal methionine.

Thus, polynucleotides of the present invention include those with a sequence encoding a peptide of the invention fused to a marker sequence, such as a sequence encoding a peptide that facilitates purification of the fused peptide. In certain preferred embodiments of this aspect of the invention, the marker amino acid sequence is a hexa histidine peptide, such as the tag provided in a pQE vector (Qiagen, Inc.), among others, many of which are commercially available. The "HA" tag is another peptide useful for purification which corresponds to an epitope derived from the influenza hemagglutinin protein.

The present invention further relates to variants of the nucleic acid molecules of the present invention, which encode variants of the peptides of the present invention.

Such variants include those produced by nucleotide substitutions, deletions or additions that may involve one or more nucleotides. Non-naturally occurring variants may be produced using mutagenesis techniques known to those in the art. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the encoded peptide. Also especially preferred in this regard are conservative substitutions.

It will be further recognized in the art that, for such nucleic acid molecules that are not degenerate variants, a reasonable number will also encode a peptide of the invention having one or more properties of the full peptide such as being able to interact with the EN1-interacting EPRS molecule (or another transcription factor acting as an oncogene such as a PBX, Paired or Distaless family member). This is because the skilled artisan is fully aware of amino acid substitutions that are either less likely or not likely to significantly effect protein function (e.g., replacing one aliphatic amino acid with a second aliphatic amino acid).

A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

cDNA or genomic libraries of various types may be screened as natural sources of the polynucleotides encoding the peptides of the invention. Such polynucleotides may be provided by amplification of sequences resident in genomic DNA or other natural sources, e.g., by PCR. The choice of cDNA libraries normally corresponds to a tissue source that is abundant in mRNA for the desired proteins. Phage libraries are normally preferred, but other types of libraries may be used. Clones of a library are spread onto plates, transferred to a substrate for screening, denatured and probed for the presence of desired sequences.

Techniques for nucleic acid manipulation are described generally, for example, in Sambrook et al., 1989: "Molecular Cloning: a laboratory manual. Sambrook, J., Fritsch, E. F. and Maniatis, T. (1989). Coldspring Harbour Laboratory Press, Coldspring Harbour, N.Y. or Ausubel et al., 1992 Current Protocols in Molecular Biology. Ausubel, F. M., Brent, R., Kingston, R. E., Moore, D. D., Seidman, J. G., Smith, J. G. and Struhl, K. (1987). John Wiley and Sons, NY. Reagents useful in applying such techniques, such as restriction enzymes and the like, are widely known in the art and commercially available from such vendors as New England BioLabs, Boehringer Mannheim, Amersham, Promega Biotec, U.S. Biochemicals, New England Nuclear, and a number of other sources. The recombinant nucleic acid sequences used to produce peptides of the present invention may be derived from natural or synthetic sequences. Many natural gene sequences are obtainable from various cDNA or from genomic libraries using appropriate probes. See, GenBank, National Institutes of Health.

Probe sequences may also hybridize specifically to duplex DNA under certain conditions to form triplex or other higher order DNA complexes. The preparation of such probes and suitable hybridisation conditions are well known in the art.

The probes include an isolated polynucleotide attached to a label or reporter molecule and may be used to isolate other polynucleotide sequences, having sequence similarity by standard methods. For techniques for preparing and labeling probes see, e.g. Sambrook et al., 1989: "Molecular Cloning: a laboratory manual. Sambrook, J., Fritsch, E. F. and Maniatis, T. (1989). Coldspring Harbour Laboratory Press, Coldspring Harbour, N.Y. or Ausubel et al., 1992 Current Protocols in Molecular Biology. Ausubel, F. M., Brent, R., Kingston, R. E., Moore, D. D., Seidman, J. G., Smith, J. G. and Struhl, K. (1987). John Wiley and Sons, NY. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of a peptide of the invention, perhaps to change ligand-binding affinities, interchain affinities, or the polypeptide degradation or turnover rate.

Probes comprising synthetic oligonucleotides or other polynucleotides encoding peptides of the present invention may be derived from naturally occurring or recombinant single- or double-stranded polynucleotides, or be chemically synthesized. Probes may also be labelled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding a peptide according to the present invention or fragment thereof are preferred as probes. The probes may also be used to determine whether mRNA encoding the peptide is present in a recombinant cell.

Vectors and Host Cells

The present invention provides an expression vector comprising a polynucleotide encoding a peptide of the invention as described herein.

A nucleic acid molecule encoding the amino acid sequence of a peptide of the invention may be inserted into an appropriate expression vector using standard ligation techniques. The vector is typically selected to be functional in the particular host cell employed (i.e., the vector is compatible with the host cell machinery such that amplification of the nucleic acid molecule and/or expression of the nucleic acid molecule can occur). A nucleic acid molecule encoding the amino acid sequence of a peptide of the invention may be amplified/expressed in prokaryotic, yeast, insect (baculovirus systems), and/or eukaryotic host cells. Selection of the host cell will depend in part on whether the peptide is to be post-translationally modified (e.g., glycosylated and/or phosphorylated). If so, yeast, insect, or mammalian host cells are preferable.

Typically, expression vectors used in any of the host cells will contain sequences for plasmid maintenance and for cloning and expression of exogenous nucleotide sequences. Such sequences, collectively referred to as "flanking sequences" in certain embodiments, will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for secretion of the peptide, a ribosome binding site, a polyadenylation sequence, a polylinker region for inserting the nucleic acid encoding the peptide to be expressed, and a selectable marker element. Each of these sequences is discussed below.

Optionally, the vector may contain a "tag"-encoding sequence, i.e., an oligonucleotide molecule located at the 5' or 3' end of the peptide coding nucleic acid sequence; the oligonucleotide sequence encodes polyHis (such as hexa-His), or another "tag" such as FLAG, HA (hemaglutinin influenza virus) or myc for which commercially available antibodies exist. This tag is typically fused to the peptide upon expression of the peptide, and can serve as a means for affinity purification of the peptide from the host cell. Affinity purification can be accomplished, for example, by column chromatography using antibodies against the tag as an affinity matrix. Optionally, the tag can subsequently be removed from the purified peptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source) or synthetic, or the flanking sequences may be native sequences that normally function to regulate polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

The flanking sequences useful in the vectors of this invention may be obtained by any of several methods well known in the art. Typically, flanking sequences useful herein other than the gene flanking sequences will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with suitable oligonucleotide and/or flanking sequence fragments from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of the peptide. If the vector of choice does not contain an origin of replication site, one may be chemically synthesized based on a known sequence, and ligated into the vector. For example, the origin of replication from the plasmid pBR322 (Product No. 303-3s, New England Biolabs, Beverly, Mass.)

is suitable for most Gram-negative bacteria, and various origins (e.g., SV40, polyoma, adenovirus, vesicular stomatitus virus (VSV) or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the nucleic acid molecule that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure that only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes a peptide of the invention. As a result, increased quantities of the peptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the peptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct the peptide out of the host cell. Typically, a nucleotide sequence encoding the signal sequence is positioned in the coding region of the nucleic acid molecule encoding the peptide, or directly at the 5' end of the polypeptide coding region. Many signal sequences have been identified, and any of those that are functional in the selected host cell may be used in conjunction with the nucleic acid molecule. Therefore, a signal sequence may be homologous (naturally occurring) or heterologous to the gene or cDNA encoding the peptide. Additionally, a signal sequence may be chemically synthesized using methods described herein. In most cases, the secretion of the peptide from the host cell via the presence of a signal peptide will result in the removal of the signal peptide from the secreted peptide. The signal sequence may be a component of the vector, or it may be a part of the nucleic acid molecule that is inserted into the vector.

Included within the scope of this invention is the use of either a nucleotide sequence encoding a native signal sequence joined to a peptide coding region or a nucleotide sequence encoding a heterologous signal sequence joined to a peptide coding region. The heterologous signal sequence selected should be one that is recognized and processed, i.e., cleaved by a signal peptidase, by the host cell. For prokaryotic host cells that do not recognize and process the native polypeptide signal sequence, the signal sequence is substituted by a prokaryotic signal sequence selected, for example, from the group of the alkaline phosphatase, penicillinase, or heat-stable enterotoxin II leaders. For yeast secretion, the native polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add presequences, which also may affect glycosylation. The final protein product may have, in the −1 position (relative to the first amino acid of the mature protein), one or more additional amino acids incidental to expression, which may not have been totally removed. For example, the final protein product may have one or two amino acid residues found in the peptidase cleavage site, attached to the N-terminus. Alternatively, use of some enzyme cleavage sites may result in a slightly truncated form of the desired polypeptide, if the enzyme cuts at such area within the mature polypeptide.

The expression and cloning vectors of the present invention will each typically contain a promoter that is recognized by the host organism and operably linked to the molecule encoding a peptide of the invention. Promoters are untranscribed sequences located upstream (5') to the start codon of a structural gene (generally within about 100 to 1000 bp) that control the transcription of the structural gene. Promoters are conventionally grouped into one of two classes, inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual polynucleotide product production; that is, there is little or no control over expression. A large number of promoters, recognized by a variety of potential host cells, are well known. A suitable promoter is operably linked to the DNA encoding the peptide of the invention by removing the promoter from the source DNA by restriction enzyme digestion and inserting the desired promoter sequence into the vector. A native gene promoter sequence may be used to direct amplification and/or expression of a nucleic acid molecule encoding a fusion protein of the invention. A heterologous promoter is preferred, if it permits greater transcription and higher yields of the expressed peptide as compared to the native promoter, and if it is compatible with the host cell system that has been selected for use.

Promoters suitable for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their sequences have been published, thereby enabling one skilled in the art to ligate them to the desired DNA sequence(s), using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowl pox virus, adenovirus (such as Adenovirus 2), bovine papilloma virus, avian sarcoma virus, cytomegalovirus (CMV), a retrovirus, hepatitis-B virus and most preferably Simian Virus 40 (SV40). Other suitable mammalian promoters include heterologous mammalian promoters, e.g., heat-shock promoters and the actin promoter.

Additional promoters which may be of interest in controlling transcription of the polynucleotide encoding a peptide of the invention include, but are not limited to: the SV40 early promoter region; the CMV promoter, the promoter contained in the 3' long terminal repeat of Rous sarcoma virus; the herpes thymidine kinase promoter, the regulatory sequences of the metallothionine gene, prokaryotic expression vectors such as the beta-lactamase promoter; or the tac promoter. Also of interest are the following animal transcriptional control regions, which exhibit tissue specificity and have been utilized in transgenic animals: the elastase I gene control region which is active in pancreatic acinar cells; the insulin gene control region which is active in pancreatic beta cells; the immunoglobulin gene control region which is active in lymphoid cells; the mouse mammary tumour virus control region which is active in testicular, breast, lymphoid and mast cells; the albumin gene control region which is active in liver; the alphafetoprotein gene control region which is active in liver; the alpha 1-antitrypsin gene control region which is active in the liver; the beta-globin gene control region which is active in myeloid cells; the myelin basic protein gene control region which is active in oligodendrocyte cells in the brain; the myosin light chain-2 gene control region which is active in skeletal muscle;

and the gonadotropic releasing hormone gene control region which is active in the hypothalamus.

An enhancer sequence may be inserted into the vector to increase the transcription of a polynucleotide encoding the peptide of the invention by higher eukaryotes. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (for example, globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a nucleic acid molecule, it is typically located at a site 5' from the promoter.

Expression vectors of the invention may be constructed from a starting vector such as a commercially available vector. Such vectors may or may not contain all of the desired flanking sequences. Where one or more of the desired flanking sequences are not already present in the vector, they may be individually obtained and ligated into the vector. Methods used for obtaining each of the flanking sequences are well known to one skilled in the art.

Preferred vectors for practicing this invention are those that are compatible with bacterial, insect, and mammalian host cells. Such vectors include, inter alia, pCRII, pCR3, and pcDNA3.1 (Invitrogen Company, Carlsbad, Calif.), pBSII (Stratagene Company, La Jolla, Calif.), pET15□ (Novagen, Madison, Wis.), pGEX (Pharmacia Biotech, Piscataway, N.J.), pEGFP-N2 (Clontech, Palo Alto, Calif.), pETL (Blue-BacII; Invitrogen), pDSR-alpha (PCT Publication No. WO 90/14363) and pFastBacDual (Gibco/BRL, Grand Island, N.Y.).

Additional suitable vectors include, but are not limited to, cosmids, plasmids or modified viruses, but it will be appreciated that the vector system must be compatible with the selected host cell. Such vectors include, but are not limited to, plasmids such as Bluescript® plasmid derivatives (a high copy number ColE1-based phagemid, Stratagene Cloning Systems Inc., La Jolla Calif.), PCR cloning plasmids designed for cloning Taq-Taq-amplified PCR products (e.g., TOPO™ TA Cloning® Kit, PCR2.1® plasmid derivatives, Invitrogen, Carlsbad, Calif.), and mammalian, yeast, or virus vectors such as a baculovirus expression system (pBacPAK plasmid derivatives, Clontech, Palo Alto, Calif.).

After the vector has been constructed and a polynucleotide molecule encoding a peptide of the invention has been inserted into the proper site of the vector, the completed vector may be inserted into a suitable host cell for amplification and/or fusion protein expression. The transformation of an expression vector for a peptide of the invention into a selected host cell may be accomplished by well-known methods including transfection, infection, calcium chloride, electroporation, microinjection, lipofection or the DEAE-dextran method or other known techniques. The method selected will in part be a function of the type of host cell to be used. These methods and other suitable methods are well known to the skilled artisan, and are set forth, for example, in Sambrook et al., supra.

The present invention provides a host cell comprising nucleic acid encoding a peptide of the invention as described herein.

Host cells may be prokaryotic host cells (such as E. coli) or eukaryotic host cells (such as a yeast cell, an insect cell or a vertebrate cell). The host cell, when cultured under appropriate conditions, synthesizes the peptide that can subsequently be collected from the culture medium (if the host cell secretes it into the medium) or directly from the host cell producing it (if it is not secreted). The selection of an appropriate host cell will depend upon various factors, such as desired expression levels, peptide modifications that are desirable or necessary for activity, such activity (such as glycosylation or phosphorylation), and ease of folding into a biologically active molecule.

A number of suitable host cells are known in the art and many are available from the American Type Culture Collection (ATCC), 10801 University Boulevard, Manassas, Va. 20110-2209. Examples include, but are not limited to, mammalian cells, such as Chinese hamster ovary cells (CHO) (ATCC No. CCL61); CHO DHFR-cells (Urlaub et al., Proc. Natl. Acad. Sci. USA, 97:4216-4220 (1980)); human embryonic kidney (HEK) 293 or 293T cells (ATCC No. CRL1573); or 3T3 cells (ATCC No. CCL92). The selection of suitable mammalian host cells and methods for transformation, culture, amplification, screening and screening, product production and purification are known in the art. Other suitable mammalian cell lines, are the monkey COS-1 (ATCC No. CRL1650) and COS-7cell lines (ATCC No. CRL1651) cell lines, and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include, but are not limited to, mouse neuroblastoma N2A cells, HeLa, mouse L-L-929 cells, 3T3 lines derived from Swiss, Balb-c or NIH mice, BHK or HaK hamster cell lines, which are available from the ATCC. Each of these cell lines is known by and available to those skilled in the art of protein expression.

Similarly useful as host cells suitable for the present invention are bacterial cells. For example, the various strains of *E. coli* (e.g., HB101, (ATCC No. 33694) DH5α, DH10, and MC1061 (ATCC No. 53338)) are well-well known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for the expression of peptides of the present invention. Preferred yeast cells include, for example, *Saccharomyces cerivisae* and *Pichia pastoris*.

Additionally, where desired, insect cell systems may be utilized in the methods of the present invention. Such systems are described for example in Kitts et al., *Biotechniques*, 14:810-817 (1993); Lucklow, *Curr. Opin. Biotechnol.*, 4:564-572 (1993); and Lucklow et al. (J al., *J. Virol.*, 67:4566-4579 (1993). Preferred insect cells are Sf-9 and Hi5 (Invitrogen, Carlsbad, Calif.).

One may also use transgenic animals to express glycosylated peptides of the invention. For example, one may use a transgenic milk-producing animal (a cow or goat, for example) and obtain the present glycosylated peptide in the animal milk. One may also use plants to produce peptides of the invention. However, in general, the glycosylation occurring in plants is different from that produced in mammalian cells, and may result in a glycosylated product which is not suitable for human therapeutic use.

Methods and Uses for Peptides of the Invention

In a further aspect, the present invention provides methods and uses for purified and isolated peptides of the invention, the peptides comprising:
(i) the amino acid sequences of SEQ ID NOs: 1 to 8; or
(ii) the amino acid sequence $PL_2V_3W_4PAWV_8Y_9C_{10}TRSDR$ (SEQ ID NO: 4) or $KKKRKPL_2V_3W_4PAWV_8Y_9C_{10}TRSDR$ (SEQ ID NO: 8), wherein:
$L_2$ is one of: L, M, or I;
$V_3$ is one of: V or L;
$W_4$ is one of: W, Y, or W analog;
$V_8$ is one of: V or I;
$Y_9$ is one of: Y or F; and
$C_{10}$ is one of: C or S.

The peptides of the invention described herein comprise variants of the anchorage protein-protein and putative DNA binding domains of $TF_{HD}$ EN1. They can be used as interference peptides which can interact with EPRS and PBX1A (or another transcription factor acting as an oncogene such as a PBX, Paired or Distaless family member) in a cell thereby preventing interaction of EPRS to EN1 or PBX1A to EN2.

For example, one or more peptides of the invention may be used to interact with EPRS (or another transcription factor acting as an oncogene such as a PBX, Paired or Distaless family member) and prevent or block binding of EN1 to EPRS in a cell which expresses EN1. The invention provides a method for preventing interaction of EN1 to EPRS in a cell, comprising introducing into the cell a peptide of the invention which interacts with EPRS therein preventing interaction of EPRS to EN1. This interference by the peptides of the invention prevents or blocks downstream signaling events commonly initiated by the interaction of EN1 and EPRS in an EN1 expressing cell. EN1 signaling through EPRS alters transcription of a high number of inflammatory molecules, notably chemokines and chemokine receptors, which can mediate pro-survival signaling pathways. EN1 signaling also confers resistance of EN1 expressing cancer and other cells to chemotherapeutic agents. Blocking or preventing binding of EN1 to EPRS (or another transcription factor acting as an oncogene such as a PBX, Paired or Distaless family members) in a cell using peptides of the invention can in turn prevent signaling to the pro-survival signaling pathways, and caspase 3 and other apoptotic signaling pathways can be activated or no longer blocked by signaling through EN1. Thus, peptides of the invention can be used to activate the caspase 3 pathway in an EN1 and/or EN2 expressing cell. The invention also provides a method of activating the caspase 3 pathway in a cell expressing either or both of EN1 and EN2, the method comprising introducing into the cell a peptide of the invention. The peptides of the invention can also be used to induce apoptosis of an EN1 and/or EN2 expressing cell. The invention also provides a method of inducing apoptosis in a cell expressing EN1 and/or EN2, the method comprising introducing into the cell a peptide of the invention.

Cancer cells expressing EN1 and/or EN2 are protected from cell death by the EN1 and/or EN2 signaling to pro-survival pathways resulting in cancer cells which are difficult to kill, even using chemotherapeutic agents. Peptides of the invention can be used to block or prevent binding of EN1 to EPRS in an EN1 expressing cancer cell. Thus, the invention provides a method of treating an EN1 or EN2 expressing cancer in a subject including the step of introducing peptides of the invention into the cancer cells. One example of an EN1 expressing cancer that can be treated using peptides of the invention is basal-like breast cancer. Other examples include some ovarian cancers medulloblastomas or other tumors originating in the cerebellum, and salivary gland adenoid cystic carcinomas. Examples of EN2 cancers that can be treated using peptides of the invention include neuroblastoma, breast cancer, and prostate cancers. Thus, the invention provides a method for treating a basal-like breast tumor or another EN1 and/or EN2 expressing cancer in a subject, and preferably a human subject, the method comprising the step of introducing peptides of the invention into the cells of the cancer. The peptides of the invention then prevent downstream signaling to pro-survival pathways in the cancer cell and can promote caspase 3 pathway and apoptosis of the cancer cell. Examples of EN2 expressing cancers that can be treated using peptides of the invention include, but are not limited to, neuroblastoma, breast cancer and prostate cancer.

Anti-cancer activity was monitored in high-throughput cell viability assays (CellTiter Glo) followed by caspase-3 apoptosis assays in a panel of breast cell lines expressing different amounts of EN1 as shown in FIG. 15 (top panel) and FIG. 16 for the parent peptide.

To validate the specificity of the EN1-iPeps in competing with the EN1 TF, SUM149 cells are transduced with the EN1 cDNA and then challenged with the peptides (4). The EN1 cDNA will rescue the cell proliferation defect of the active EN1-iPeps. To determine the internalization and half-life of the iPeps in the cells, the real-time incorporation of FITC-labelled iPeps is quantitated by confocal microscopy.

The peptides may be administered via a variety of methods, for example, as a therapeutic depending on the particular circumstances and as deemed appropriate by a medical practitioner.

Therapeutic Methods and Compositions

Pharmaceutical Compositions

In another aspect, the present invention provides a composition, and in particular a pharmaceutical composition comprising one or more of the peptides of the invention which comprise:
(i) the amino acid sequences of SEQ ID NOs: 1 to 8; or
(ii) the amino acid sequence $PL_2V_3W_4PAWV_8Y_9C_{10}TRSDR$ (SEQ ID NO: 4) or $KKKRKPL_2V_3W_4PAWV_8Y_9C_{10}TRSDR$ (SEQ ID NO: 8), wherein:
$L_2$ is one of: L, M, or I;
$V_3$ is one of: V or L;
$W_4$ is one of: W, Y, or W analog;
$V_8$ is one of: V or I;
$Y_9$ is one of: Y or F; and
$C_{10}$ is one of: C or S.

A used herein the term "subject" preferably refers to a human subject. However, it will also include reference to other animals, in particular animals, which are considered of high value by humans.

It may be preferable to administer the peptides of the invention in combination with other therapeutic agents that are useful for treating cancer.

Effective doses of the compositions of the present invention, for the treatment of the above described conditions vary depending upon many different factors, including means of administration, target site, physiological state of the patient, whether the patient is human or an animal, and other medications administered. Treatment dosages need to be titrated to optimize safety and efficacy.

Therapeutic Compositions

Therapeutic compositions are within the scope of the present invention. Peptides of the invention may be combined with various components to produce compositions of the invention. Such compositions may comprise a therapeutically effective amount of a peptide of the invention in admixture with a pharmaceutically or physiologically acceptable formulation agent selected for suitability with the mode of administration. The present invention provides the use of an effective amount of a peptide of the invention as described herein, in the manufacture of a medicament for treating an EN1 or EN2 expressing cancer, for example, EN1 expressing cancers including ovarian cancer, medulloblastoma and other cancers originating in the cerebellum, salivary gland adenoid cystic carcinoma, and preferably a basal-like breast tumor; and EN2 expressing cancers including neuroblastoma, breast cancer, and prostate cancers.

Medicaments including pharmaceutical compositions may also comprise a therapeutically effective amount of one or more peptide of the invention in admixture with a pharmaceutically or physiologically acceptable formulation agent selected for suitability with the mode of administration. Preferably the compositions are combined with a pharmaceutically acceptable carrier or diluent to produce a pharmaceutical composition (which may be for human or animal use). Suitable carriers and diluents include isotonic saline solutions, for example phosphate-buffered saline. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. See, for example, Remington's Pharmaceutical Sciences, 19th Ed. (1995, Mack Publishing Co., Easton, Pa.) which is herein incorporated by reference.

The pharmaceutical composition may contain formulation materials for modifying, maintaining or preserving, for example, the pH, osmolarity, viscosity, clarity, colour, isotonicity, odour, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin), fillers; monosaccharides, disaccharides; and other carbohydrates (such as glucose, mannose, or dextrins); proteins (such as serum albumin, gelatin or immunoglobulins); colouring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapol); stability enhancing agents (sucrose or sorbitol); tonicity enhancing agents (such as alkali metal halides, preferably sodium or potassium chloride), delivery vehicles, diluents, excipients and/or pharmaceutical adjuvants.

The optimal pharmaceutical composition will be determined by one skilled in the art depending upon, for example, the intended route of administration, delivery format, and desired dosage. Such compositions may influence the physical state, stability, rate of in vivo release, and rate of in vivo clearance of the peptide of the invention. The preferred form of the pharmaceutical composition depends on the intended mode of administration and therapeutic application. Pharmaceutical compositions prepared according to the invention may be administered by any means that leads to the peptides of the invention coming in contact with a causative agent of a disease or disorder as herein described including EN1 and/or EN2 expressing cancer cells.

The primary vehicle or carrier in a pharmaceutical composition may be either aqueous or non-aqueous in nature. For example, a suitable vehicle or carrier may be water for injection, physiological saline solution, solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefor. In one embodiment of the present invention, pharmaceutical compositions may be prepared for storage by mixing the selected composition having the desired degree of purity with optional formulation agents in the form of a lyophilized cake or an aqueous solution. Further, the peptide product may be formulated as a lyophilizate using appropriate excipients such as sucrose.

The pharmaceutical compositions can be capable of parenteral delivery. Alternatively, the compositions may be capable of inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired peptide of the invention in a pharmaceutically acceptable vehicle. A particularly suitable vehicle for parenteral injection is sterile distilled water in which the active agent is formulated as a sterile, isotonic solution, properly preserved. Yet another preparation can involve the formulation of the desired molecule with an agent, such as injectable microspheres, bio-erodible particles, polymeric compounds (such as polylactic acid, acid or polyglycolic acid), or beads or liposomes, that provides for the controlled or sustained release of the product which may then be delivered as a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, a peptide may be formulated as a dry powder for inhalation. The peptide inhalation solution may also be formulated with a propellant for aerosol delivery. In yet another embodiment, solutions may be nebulized. Pulmonary administration is further described in PCT application no. PCT/US94/001875, which describes pulmonary delivery of chemically modified proteins.

It is also contemplated that certain formulations may be administered orally. In one embodiment of the present invention, peptides of the present invention that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the active agent. Diluents, flavourings, low melting point waxes, vegetable oils, lubricants, suspending agents, tablet disintegrating agents, and binders may also be employed.

Another pharmaceutical composition may involve an effective quantity of a peptide of the invention in a mixture with non-toxic excipients that are suitable for the manufacture of tablets. By dissolving the tablets in sterile water, or another appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving a peptide of the invention in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT Application No. PCT/US93/00829 that describes the controlled release of porous polymeric microparticles for the delivery of pharmaceutical compositions. Additional examples of sustained-sustained-release preparations include semipermeable polymer matrices in the form of shaped articles, for example, films, or microcapsules. Sustained release matrices may include polyesters, hydrogels, polylactides, copolymers of L-glutamic acid and gamma ethyl-L-glutamate, ethylene vinyl acetate or poly-D(-)-3-hydroxybutyric acid. Sustained-release compositions may also include liposomes, which can be prepared by any of several methods known in the art.

The pharmaceutical composition to be used for in vivo administration typically must be sterile. This may be accomplished by filtration through sterile filtration membranes. Where the composition is lyophilized, sterilization using these methods may be conducted either prior to, or following, lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

The effective amount of the active agent in the pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the active agent is being used, the route of administration, and the size (body weight, body surface or organ size) and condition (the age and general health) of the patient. Accordingly, the clinician may titre the dosage and modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

The frequency of dosing will depend upon the pharmacokinetic parameters of the active agent and the formulation used. Typically, a clinician will administer the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g., orally, through injection by intravenous, intracoronary, intraperitoneal, intracerebral (intra-parenchymal), intracerebroventricular, intramuscular, intra-ocular, intraarterial, intraportal, or intralesional routes; by sustained release systems or by implants. Where desired, the compositions may be administered by bolus injection or continuously by infusion, or by implantation device.

Alternatively or additionally, the composition may be administered locally via implantation of a membrane, sponge or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use the pharmaceutical compositions herein in an ex vivo manner. In such instances, cells, tissues, or organs that have been removed from the subject to be treated are exposed to the pharmaceutical compositions after which the cells, tissues and/or organs are subsequently implanted back into the subject.

In another form, nanoparticles may be employed as carriers for delivery of peptides of the invention. Nanoparticles have been shown to overcome some limitations of conventional therapeutic delivery such as nonspecific biodistribution and targeting, and lack of water solubility, amongst others. Thus, nanoparticles such as tumor-specific nanoparticles may be used for delivering peptides of the invention to EN1 and/or EN2 expressing cancer cells for treatment of a subject with the peptides.

The routes of administration described herein are intended only as a guide since a skilled practitioner will be able to determine readily the optimum route of administration and dosage for any particular subject requiring treatment.

For EN1 expressing cancers such as basal-like breast tumors, chemotherapy has previously been shown to have limited success because the tumors develop resistance to the chemotherapeutic drugs resulting in recurrence of the tumors and patient death. However, the peptides of the present invention may be used in combination with chemotherapeutic drugs to sensitize cancer cells to chemotherapy and other treatments, for example, to reduce the $IC_{50}$ of the chemotherapeutic drugs. Thus, the present invention further provides the use of a combination of one or more chemotherapeutic drugs, and a peptide of the invention as described herein, for treating a subject with cancer, wherein the cancer cells express either or both of EN1 and EN2. For example, EN1 expressing cancers including ovarian cancer, medulloblastoma and other cancers originating in the cerebellum, salivary gland adenoid cystic carcinoma, and preferably a basal-like breast tumor; and EN2 expressing cancers including neuroblastoma, breast cancer, and prostate cancers.

The combination of one or more chemotherapeutic drugs, and a peptide of the invention as described herein may be administered to a subject concomitantly or sequentially. Preferably, the peptide of the invention is administered to the subject following treatment with the one or more chemotherapeutic drugs.

Encapsulation of EN1-iPeps.

In order to be utilised in a clinical setting, functionalized iPeps are desirably encapsulated in nanoparticles (NPs) to protect the peptides from degradation in plasma and to avoid the targeting of EN1+ dopaminergic cells in the brain. (i) In particular such particles have improved therapeutic or diagnostic properties and can be designed to carry a large therapeutic 'payload' (e.g. drugs and peptides); (ii) such a platform can be attached to multivalent targeting ligands, which yield high affinity and specificity for target cells without the need to completely reformulate the composition; (iii) it can accommodate multiple drug molecules that simultaneously enable combinatorial cancer therapy and most importantly (iv) it has demonstrated zero off-target toxicity following treatment. The core platform of the formulation is composed of polymer nanospheres prepared from rhodamine B (RhB)-modified poly(glycidyl methacrylate) (PGMA), along with encapsulated magnetite ($Fe_3O_4$). This enables tracking of the NPs using magnetic resonance imaging (MRI) and fluorescence microscopy.

The advantage of using such a formulation is that the technology provides epoxide groups on PGMA (FIG. 17), which enable tethering of a range of functional moieties by means of a simple ring-opening to tailor the surface properties (Evans C W, Fitzgerald M, Clemons T D, et al. Multimodal analysis of PEI-mediated endocytosis of nanoparticles in neural cells. ACS nano. 2011 Nov. 22; 5(11): 8640-8). The mobility of the reactive loops of PGMA ensures a 2-3 fold greater attachment of targeting ligands when compared to traditional nanoformulations enabling very high propensity to reach the desired site of therapy whilst minimizing off-target toxicity (Evans C W, Fitzgerald M, Clemons T D, et al. Multimodal analysis of PEI-mediated endocytosis of nanoparticles in neural cells. ACS nano. 2011 Nov. 22; 5(11):8640-8).

Specifically herein the inventors used: (i) Near infrared (IR) dye for the in vivo imaging of NP in future whole-animal studies. (ii) EN1-iPep and HF to induce tumour cell apoptosis. (iii) Polyethylene glycol (PEG), which protects the NP from degradation in the blood stream.

NPs with high density of PEG demonstrated unprecedented levels (60-80% injected dose/gram of tissue) of tumour accumulation, and decreased uptake by the reticuloendothelial system while evading opsonisation and internalization by the liver (Li S D, Huang L. Surface-modified LPD nanoparticles for tumor targeting. Annals of the New York Academy of Sciences. 2006 October; 1082:1-8). (iv) Attachment of chemical ligand for specific tumor cell internalization e.g anisamide (AA, which targets sigma receptors overexpressed in breast cancer cells (Banerjee R, Tyagi P, Li S, et al. Anisamide-targeted stealth liposomes: a potent carrier for targeting doxorubicin to human prostate cancer cells. International journal of cancer Journal international du cancer. 2004 Nov. 20; 112(4):693-700) to the PEG chain on the NP surface or alternatively by coupling RGD peptide (Sugahara K N, Teesalu T, Karmali P P, et al. Tissue-penetrating delivery of compounds and nanoparticles into tumors. Cancer cell. 2009 Dec. 8; 16(6):510-20) or folic acid to the epoxy groups. (v) Incorporation of MRI contrast agent to study NP distribution in organs using magnetic resonance relaxometry (Harrison J, Bartlett C A, Cowin G, et al. In vivo imaging and biodistribution of multimodal polymeric nanoparticles delivered to the optic nerve. Small. 2012 May 21; 8(10):1579-89).

In vitro transfection of NPs encapsulating the EN1-iPep and HF is performed in a panel of breast cancer cell lines (Lara H, Wang Y, Beltran A S, et al. Targeting serous epithelial ovarian cancer with designer zinc finger transcription factors. J Biol Chem. 2012 Aug. 24; 287(35):29873-86) to rapidly determine the NP formulations carrying stronger anti-cancer activity with minimal toxicity to normal mammary epithelial cells (HUMECs). NPs loaded with the inactive EN1-iPep and untargeted NPs (in absence of targeting AA ligand) were used as a control. Single treatments (iPep/HF) were also be tested.

The combination [iPep+HF] was anticipated to be superior to single agents in decreasing breast cancer cell viability as demonstrated in aim 2a. To test whether the targeted NPs can effectively induce apoptosis in clinically relevant specimens TNBC spheroids (tumorspheres) were derived from surgically removed primary or if available, metastatic tissue. Primary cultures of these cells were then subsequently tested with NPs for anti-cancer activity as described above. Feasibility and progress: Multifunctional NPs loading small molecules together with other cargoes (peptides and siRNAs) have been previously reported. Currently NPs encapsulating the EN1-iPep have been successfully assembled (FIG. 18).

For pre-clinical studies, mice were implanted subcutaneously with the following EN1+ cell lines: 1) T11 cells from a p53−/− mice implanted in a BALB/c syngeneic host. 2) Human SUM149 line implanted as an s.c xenograft in nude mice. To determine the off-target effects of the NPs in non-basal lines, the EN1-MDA-MB-231 cell line. 5×106 tumour cells will be implanted with matrigel in the flank of the mice (N=12/group). When tumours reach 50 mm3 (~2-3 weeks post-injection) NP groups ([iPep-EN1+HF]; EN1-iPep; HF) and NP controls (untargeted NPs; NPs loaded with a mutated EN1-iPep) were injected into the tail vein in a solution of 500 ul of NP suspension (2.3 mg/kg).

Treatments were performed every other day with a total of 5 injections. Mice were monitored for reduction of tumour growth by caliper measurements every 2 days before and after the first injection. Differences in tumour growth between targeted active NP groups and controls were determined by student t test (p<0.05). In vivo fluorescence imaging of the animals injected with IR-containing NPs will determine the % uptake in the tumour and other organs and the % of red fluorescent cells were quantitated by IF in tissue sections.

Statistically significant reduction of tumour growth in NPs carrying either active EN1-iPeps or HF, with EN1-iPeps in combination with HF being highly potent combination. Potential synergistic interactions between EN1-iPep and HF were calculated with the combinatorial index method. Potential Pitfalls/alternative approaches: To determine the background of our approach, the % of tumour growth reduction of the EN1-MDA-MB-231 cell line were monitored, which was anticipated to be significantly lower than that in T11 and SUM149 grafts based on the selectivity of targeting provided by the EN1-iPep.

Synergistic Combinations

In accordance with the invention combinatorial treatment between the EN1-iPeps and agents such as those identified below have utility in the treatment of TNBCs: EGFR inhibitors (erlotinib, cetuximab), PARP inhibitors (olaparib), paclitaxel, gemcitabine, cisplatin, anthracyclines cyclophosphamide, methotrexate and fluorouracil (5-FU)

Kits

In another aspect, the present invention provides a kit for treating an EN1 and/or EN2 expressing cancer in a subject, comprising at least one of the following:
(i) one or more of the peptides of the invention comprising:
i. the amino acid sequences of SEQ ID NOs: 1 to 8; or
ii. the amino acid sequence PL$_2$V$_3$W$_4$PAWV$_8$Y$_9$C$_{10}$TRSDR (SEQ ID NO: 4) or KKKRKPL$_2$V$_3$W$_4$PAWV$_8$Y$_9$C$_{10}$TRSDR (SEQ ID NO: 8), wherein:
L$_2$ is one of: L, M, or I;
V$_3$ is one of: V or L;
W$_4$ is one of: W, Y, or W analog;
V$_8$ is one of: V or I;
Y$_9$ is one of: Y or F; and
C$_{10}$ is one of: C or S;
(ii) isolated polynucleotides encoding one or more of the herein described peptides of the invention;
(iii) one or more expression vectors encoding one or more of the herein described peptides of the invention; and
(iv) one or more host cells capable of expressing one or more of the herein described peptides of the invention.

Examples

Results

EN1 Expression is Restricted to the Basal-Like Subtype of Breast Cancer.

Figure 1:
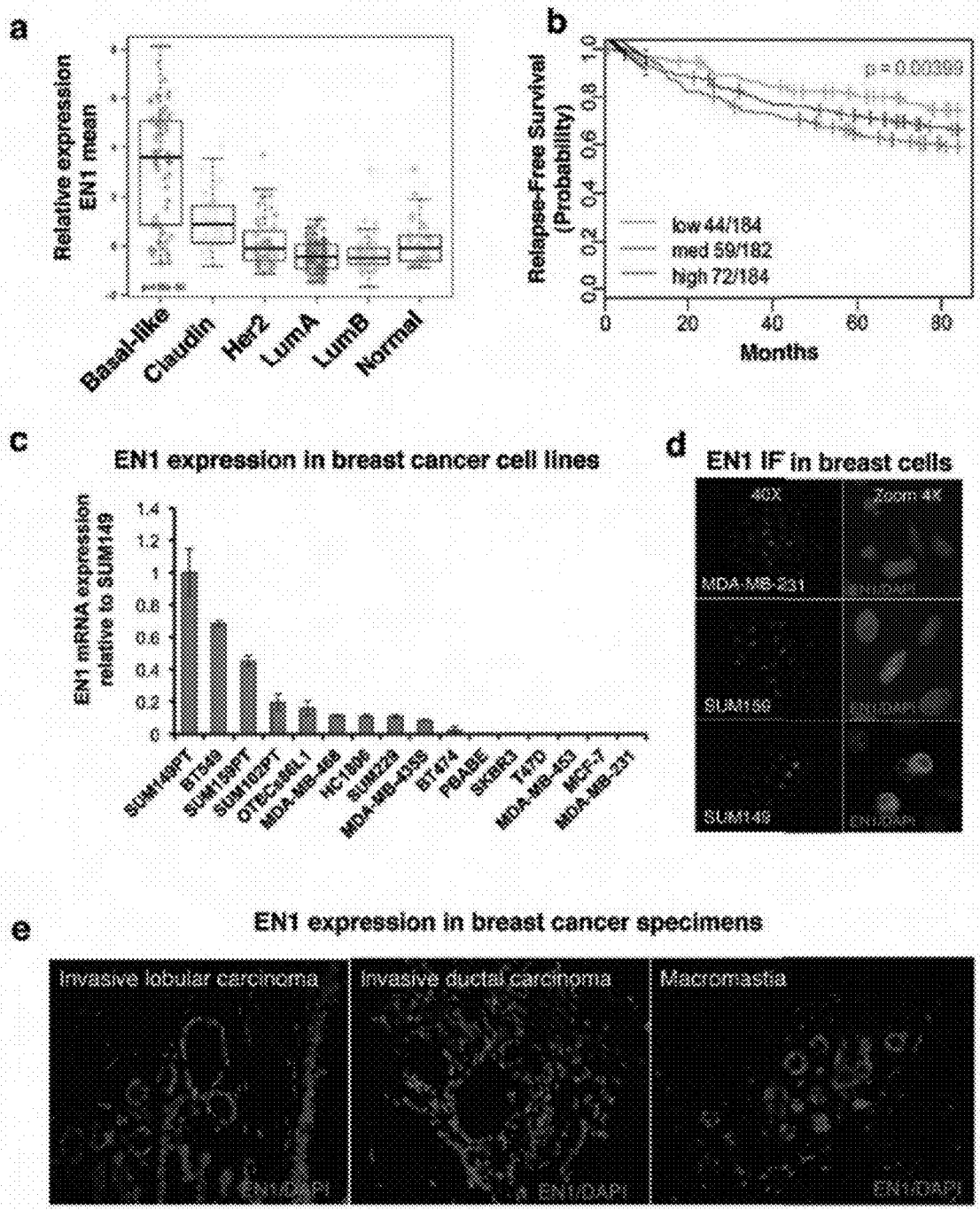
FIG. 1 Engrailed 1 (EN1) is expressed in basal-like breast cancer. (a) Box-and-whisker plot for the mean expression of EN1 across the intrinsic molecular subtypes of breast cancer on the UNC337 breast cancer patient database. P values were calculated by comparing gene expression means across all subtypes. BL=Basal-like; CL=Claudin-low; Her2=HERB-b2 enriched; LA=Luminal A; LB=Luminal B; NL=Normal-like. (b) Kaplan-Meier (KM) plot of relapse-free survival indicates that EN1 positivity in basal-like breast carcinoma from the Merge 550 tumor database is correlated with poor survival (p=0.00399) in high expressing tumors. (c) EN1 mRNA levels by qRT-PCR in a panel of breast cancer cell lines. Data was normalized to SUM149PT cell line and represents the average and standard deviation (SD) of three independent experiments. (d) EN1 immunofluorescence detection in representative high-(SUM149PT, SUM159PT) and low-(MDA-MB-231) EN1-expressing cell lines. EN1 (red) was labeled with Alexa 594 and nucleus (blue) with DAPI. A representative picture is shown. (e) EN1 immunofluorescence detection in clinical specimens. The tumor 1 represents an invasive lobular carcinoma; Tumor 2, invasive ductal carcinoma; Sample 3, normal-like tissue (macromastia).

To identify oncogenic TF$_{FD}$s in basal-like breast cancers, the inventors first examined the mRNA expression of more than 200 TF$_{HD}$s using the UNC337 gene expression tumor database. A total of 114 TF$_{HD}$s were significantly differentially expressed (p<0.05) across tumor subtypes, with high representation of neural specific TF$_{HD}$s. The TF$_{HD}$s EN1 and EN2 were differentially expressed across the intrinsic subtypes (FIG. 1a). However, EN1 had the highest and most selective enrichment in the basal-like breast cancers with four-fold increased expression (p=4.65e$^{-50}$) over normal-like, HER2, Luminal A and B subtypes (FIG. 1a, 12).

To address whether EN1 expression in cancer patients correlated with poor survival the inventors took advantage of the MERGE 550 tumor database. Cancer patients with higher EN1 expression had the lowest relapse-free survival (p=0.00399), indicating an association of high EN1 expression with poor clinical outcome (FIG. 1b). Conversely, EN2 expression did not exhibit a significant impact on overall survival (data not shown).

To validate the gene expression microarray data, the inventors quantified EN1 mRNA levels in a panel of breast cancer cell lines encompassing all of the four different intrinsic subtypes of breast cancer. In accordance with the microarray data, the EN1 gene was highly expressed in basal-like cell lines with highest expression in SUM149PT, and absent in luminal lines, such as MCF-7 and normal breast epithelial cells (HUMEC, FIG. 1c). The EN1 protein expression levels in the cell lines were in accordance with mRNA levels, as assessed by immunofluorescence. EN1 protein expression was detected in a sub-population of cells, which displayed mostly strong nuclear staining (FIG. 1d).

The EN1 expression in basal-like tumor specimens revealed some cytoplasmic and mostly nuclear localization. Similar to the detection pattern in the cell lines, the EN1 staining in the tissue sections was heterogeneous. In contrast, none of the luminal tumors or normal tissue examined revealed any detectable EN1 staining (FIG. 1e). In summary, these results indicate that high expression of EN1 is restricted to breast tumors and representative cell lines belonging to the basal-like subtype.

EN1 Expression Confers Survival Features to Breast Cells

Figure 2:
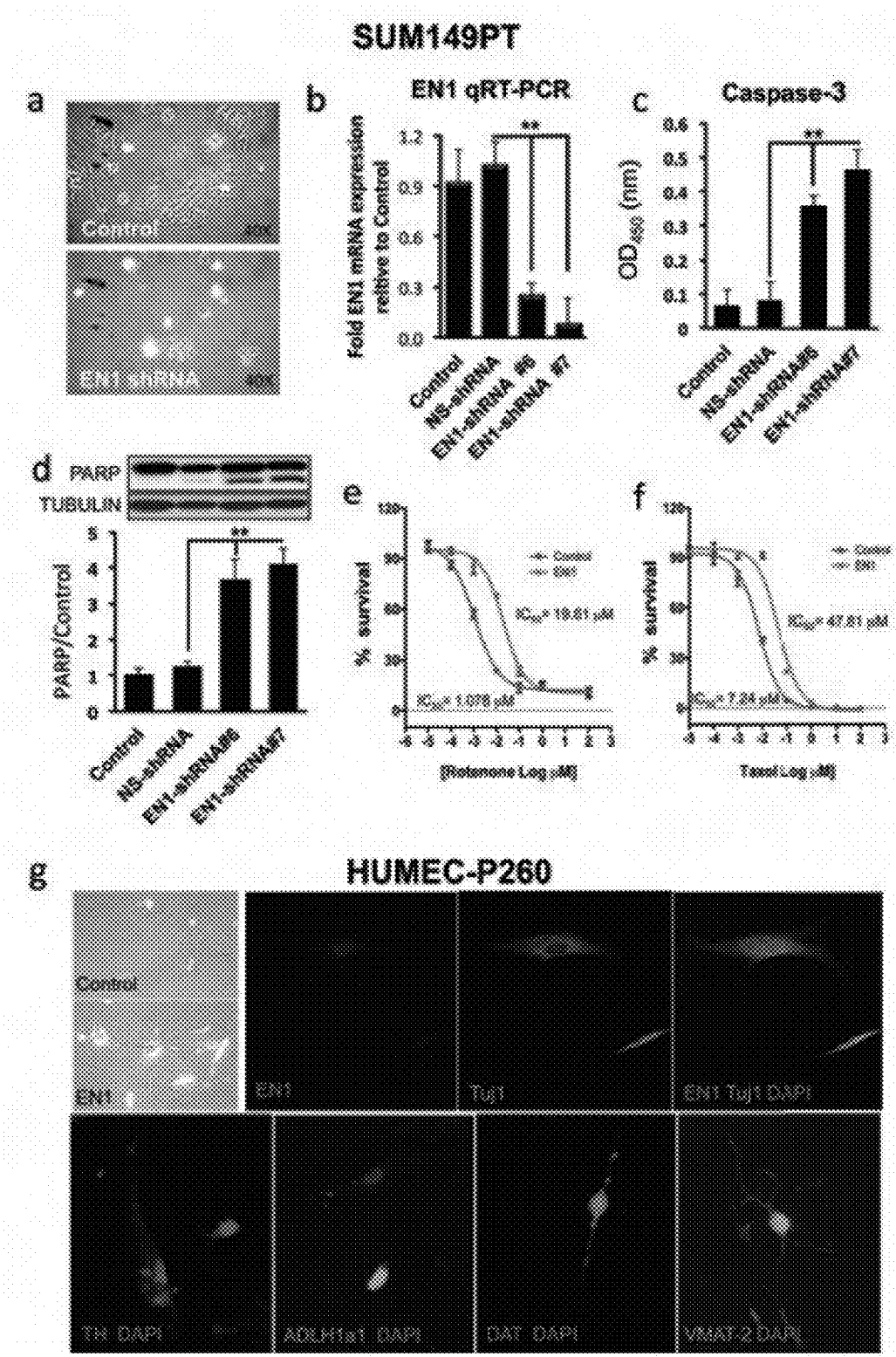
FIG. 2 EN1 confers survival features to breast epithelial cells. (a) Representative light microscopy picture of SU149PT cells after shRNA-mediated knockdown of EN1 at 40× magnification. Cells were transduced with a non-specific shRNA (upper panel) or EN1-specific shRNAs (shRNA#6 and shRNA#7, lower panel). (b) EN1 mRNA levels assessed by qRT-PCR in shRNA-transduced cells. C. Caspase 3 activity after shRNA-mediated knockdown of EN1. (d) Upper panel: representative western blot of PARP-cleavage levels in cells after shRNA-mediated knockdown of EN1. Tubulin was used as loading control. Data in (b-d) was normalized to control (non-transduced cells); the average error and standard deviation (SD) of three independent experiments is indicated. Statistical significance was analyzed using the Student t-Test ( p<0.01, * p<0.001). (e) Dose-response plots of stable SUM149PT cell lines over-expressing the EN1 cDNA or EGFP (control cells) treated with increasing concentrations of taxol and rotenone for 72 hours. (f) Cell viability was assessed by Cell Titer Glo (CTG) assay and percentage of survival (%) was normalized to the vehicle treated cells. Determination of fifty percent inhibitory concentrations (IC50) was performed using a non-linear regression method (curve fit) with the GraphPath software. (g) Light and fluorescent imaging of HUMEC-P260 overexpressing EN1. Light imaging pictures show cells transduced with a control (empty vector) and EN1 cDNA. Fluorescent images show the detection of neural specific markers (in red); tyrosine hydroxylase (TH), vesicular monoamine transporter 2 (VMAT-2), dopamine transporter (DAT), Neuron-specific class III beta-tubulin (β-III) and aldehyde dehydrogenase 1 family member A1 (ALDH1A1). Nucleus was stained with DAPI. Pictures were taken at 40×.

To decipher the role of EN1 in breast cancer cells, the inventors used lentivirally-delivered shRNAs to knockdown EN1 expression in the basal cancer cell line SUM149PT cells. Forty-eight hours post-transduction, the EN1-specific shRNAs (but not control shRNA) triggered a strong cell death (FIG. 2a) that was due to induction of apoptosis, as assessed by caspase-3 (FIG. 2c) and PARP-cleavage assays (FIG. 2d). In contrast, transfection of EN1-shRNAs in the low-EN1 expressing MDA-MB-231 cell line did not reveal any significant changes in caspase-3 activity relative to control (FIG. 7). The above results indicated that shRNA-mediated knockdown of EN1 selectively impacted survival pathways in cell lines expressing high levels of EN1.

In the neural system it has been proposed that EN1 protects neurons from mitochondrial complex I insults. Likewise, the inventors investigated whether EN1 could play a similar role in the basal-like breast cancer cell lines. The EN1 cDNA was overexpressed in SUM149PT cells using a lentiviral vector, and the transduced cells were treated with increasing concentrations of rotenone, a mitochondrial complex I toxin, and taxol, a microtubule-destabilizing agent. The transfection of the EN1 cDNA increased EN1 protein expression (FIG. 8a) and significantly increased the IC50 for rotenone (from 1.078 to 19.61 µM, FIG. 2e) and taxol (from 7.24 to 47.81 µM, FIG. 2f) relative to control transduced cells. In fact, EN1 overexpression in breast cancer cells did not result in enhanced cell proliferation (FIG. 8b-c) or tumorigenic potential, as shown by soft agar colony formation assays (FIG. 8d-e).

Lastly, the inventors examined potential downstream transcriptional targets of EN1 by performing genome-wide gene expression microarray analysis of SUM149PT cells overexpressing the EN1 cDNA and control vector (FIG. 13). Gene ontology analysis of differentially regulated genes revealed the up-regulation of pathways involved in inflammation, cytokine and chemokine activity and angiogenesis (e.g. CXCL11, CD69, IL23A, URI/2, CXCL6, IL8 and VEGF-A; FIG. 14). These results suggest a potential link between EN1 expression and inflammatory breast cancer via the activation of downstream chemokine signaling pathways.

Given the role of EN1 as a TF, the inventors reasoned that the active EN1-iPep, as a dominant negative form of the EN1 protein, should modulate transcription of EN1-dependent targets. To test this hypothesis, breast cancer cells (EN1+: SUM149; EN1−: HUMEC) were treated with the iPeps for a period of 2, 4, 8 and 10 hrs and RNA was processed for sequencing to determine global transcriptome changes. Sequencing and analysis was performed at the Australian Genome Research Facility (AGRF) in Perth, Western Australia by comparing [W9;12=>A] EN1-iPep with EN1-iPep groups.

Preliminary data demonstrate that early iPep transcriptional changes begin at 2 hrs after the addition of the peptides, reaching a maximum at 6 hrs and a decay at 10 hrs, which might be due to the half-life of the iPeps (~8-10 hrs) (FIG. 17). Significantly regulated early targets of the EN1-iPep include tumour suppressive TFs (e.g up-regulated FOXA2) and a large number of inflammatory cytokines (e.g. upregulated IL11). In addition, the inventors observed regulation of targets at later time points, which could reflect downstream (indirect) transcriptional cascades. Intriguingly, they found that the T cell antigen CD69, overexpressed in T-cell leukemias, was 99% down-regulated by the EN1-iPep at 10 hrs.

To further validate direct transcriptional changes at these loci, chromatin immunoprecipitation sequencing (ChIP-Seq) was conducted using an anti-FLAG antibody to physically detect the binding of EN1 in chromatin, and streptavidin beads to detect chromatin complexes bound to biotinlylated EN1-iPeps.

Proteins identified by MS were analysed for interaction with iPeps in vitro using CID Bond's ARC LIEF-funded Protein Production and Structure Facility and Biomolecular Interactions Facility. Following a comprehensive construct design process for overexpression of target proteins and complexes in E. coli, and purification, interactions were evaluated by electrophoretic mobility shift assays, affinity capture, microscale thermophoresis and isothermal titration calorimetry.

Validated complexes were advanced to co-crystallisation experiments, for structure solution. In the case of EPRS/HF/EN1-iPep, feasibility was high, as an X-ray structure of EPRS/HF has been recently reported (Zhou H, Sun L, Yang X L, et al. ATP-directed capture of bioactive herbal-based medicine on human tRNA synthetase. Nature. 2013 Feb. 7; 494(7435):121-4).

The inhibition of activity of EPRS upon EN1-iPep binding was quantitated in vitro as described Zhou H, Sun L, Yang X L, et al. ATP-directed capture of bioactive herbal-based medicine on human tRNA synthetase. Nature. 2013 Feb. 7; 494(7435):121-4.

To better understand the function of EN1 in the pathology of breast cancer, the EN1 cDNA was overexpressed using a lentiviral vector in primary preparations of HUMECs generated from reduction mammoplasties. HUMEC cells were transduced with either EN1 cDNA or a control EGFP, and seventy-two hours post-transduction these cells were seeded in fibroblast feeder cultures with human embryonic stem-cell medium, conditions that favor the propagation of mammary stem/progenitor cells. While the control cells underwent senescence after three weeks, the EN1 overexpressing cells survived for more than six months in culture with a very low division rate (FIG. 2g). Furthermore, the HUMECEN1 cells differentiated into neural-like cells within a period of 3 weeks when placed in neural differentiation medium. Since EN1 is normally expressed in mesencephalic dopaminergic (mDA) neurons, the expression of mDA specific markers such as tyrosine hydroxylase (TH), vesicular monoamine transporter 2 (VMAT-2), dopamine transporter (DAT), neuron-specific class III beta-tubulin (Tuj1) and aldehyde dehydrogenase 1 family member A1 (ALDH1A1) was assessed by immunofluorescence. The HUMEC-EN1 cells displayed strong EN1 nuclear and faint cytoplasmic staining; the later overlapping with Tuj1 expression (FIG. 2g top right panel). Interestingly, these cells also displayed strong DAT and VMAT expression (FIG. 2g lower left panel) as well as TH and ALDH1A1 (FIG. 2g lower right panel). Despite the increase in dopaminergic markers, the HUMEC-EN1 cells failed to display typical neuronal excitability as assessed by whole cell electrophysiological recording (data non shown), suggesting that more than a single TF is necessary for full conversion to functional dopaminergic neurons. Alternatively, transduction of EN1 could give rise to dopaminergic neurons at a very low frequency. Overall, these results suggest that expression of EN1 in breast cells could activate developmental pathways similar to those of dopaminergic neurons, providing cells a means to sustain survival against apoptotic stimuli.

Targeting EN1 with Interference Peptides (iPeps)

To inhibit the function of EN1 as a TF in basal-like breast cells the inventors engineered synthetic interference peptides (iPeps) comprising the EN1-specific hexamotif and flanking protein sequences from the N-terminus of the homeodomain. Synthetic peptides comprising either the murine EN2 or HOXA9 hexamotifs have been previously shown to compete in vitro with the EN2-PBX1 or HOXA9-PBX1 complexes and disrupt $TF_{HD}$-$TF_{HD}$ interactions necessary for cooperative DNA-binding. As shown in FIG. 3a, the interaction between PBX1 and HOXA9 is mediated by a hexamotif-like sequence. A similar hexamotif sequence (WPAWVY) (SEQ ID NO: 13) is present in human EN1 protein, and located at the N-terminus of the HD. The inventors reasoned that the delivery of a synthetic peptide comprising the human EN1 hexamotif and flanking sequences would phenocopy the effect of the EN1-specific shRNAs and induce selective cell death in the basal-like breast cancer cells.

Sequence comparison showed that the hexamotif WPAWVY (SEQ ID NO: 13) and the CTRYSDRPS (SEQ ID NO: 16)C-terminal sequence of the human EN1 protein were highly conserved among vertebrate and invertebrate species (FIG. 3b). A specific cell penetrating peptide (CPP; sequence KKKRKV) (SEQ ID NO: 10) that acts as nuclear localization sequence (NLS) was included in the N-terminus of the iPep sequence variants (FIG. 3c). The inventors chose this specific NLS/CPP sequence since it has been shown to be effective in mediating penetration of peptide cargos containing hydrophobic residues, such as W and Y.

The EN1-iPeps and iPep controls were first tested in SUM149PT cells carrying high EN1 expression. Cells were first treated with a full-length 29-mer peptide (iPep624) comprising the N-terminal, less conserved amino acid sequences, the hexamotif, and the C-terminal tail. As a control, the inventors generated the iPep624ΔHEX in which the hexamotif was mutated from the wild type (wt) WPAWVY (SEQ ID NO: 13) to the GAAGAG (SEQ ID NO: 15) sequence. These mutations were expected to dramatically abolish the activity of the peptide. Both peptides were included in the culture medium of the basal cancer cells in increasing (0-100 μM) concentrations and incubated for 8 hours at 37° C. Treated cells were first analyzed using the Cell Titer Glo assay, which monitors metabolic viability. While cells treated with the iPep624ΔHEX did not show significant changes in cell viability, even at 100 μM, the cells treated with iPep624 strongly reduced viability in a dose-dependent manner with an IC50 of 17.5 μM (FIG. 3d). This calculated value of IC50 is in the range of concentrations observed with other peptides delivered with CPPs. Both caspase 3 activity (FIG. 3e) and the number of apoptotic nuclei (FIG. 30 were significantly higher in the iPep624-treated cells as compared with non-treated or iPep624ΔHEX-treated cells. Furthermore, the cell viability defect provoked by the iPep624 was rescued by ectopic transfection of the EN1 cDNA (FIG. 3g), suggesting that with greater EN1 more peptide is needed to inhibit its function. These experiments indicate that the apoptotic response induced by EN1-iPep624 was specific and dependent on the expression of EN1.

To rule out the possibility that differences in apoptosis were the consequence of differential internalization and/or intracellular distribution of the peptides, real-time peptide internalization studies were performed. Both active and mutant iPeps were coupled to a C-terminal fluorescein and delivered into SUM149PT cells. Cells were imaged every two minutes for a total of 60 minutes using a confocal microscope and total fluorescence per image was measured as total number of pixels captured at 488 nm at each specific time point. The inventors found that both, active and inactive iPeps entered in the cytoplasm in less than two minutes and reached a plateau with saturating levels of fluorescence in ~40 minutes (FIG. 4a-b; FIG. 9).

EN1-iPeps Selectively Target Basal-Like Breast Cancer Lines Expressing EN1

To test the specificity of the EN1-iPep in cell lines expressing EN1, the inventors delivered the iPeps into a panel of breast cancer cell lines expressing different amounts of EN1. The iPep624 selectively decreased cell viability of basal-like EN1-expressing cell lines such as SUM149PT, SUM159PT, SUM102, and SUM229 but had no effect on cell viability in low or non-expressing EN1 cell lines, such as the MCF7, MDA-MB-231, and HUMEC cell lines (FIG. 5a). In addition, the mutant iPep624ΔHEX peptide did not significantly affect cell viability of any of the breast cancer cell lines at the maximum tested concentrations (100 μM) (FIG. 5b).

To investigate the requirement of the two W residues in the activity of the peptide, mutant iPeps were generated with either the first (iPep624W1ΔA) or the second tryptophan (iPep624W2ΔA) mutated to alanine and delivered into SUM149PT cells. These mutations were expected to disrupt the structure of the hydrophobic pocket necessary for EN1 to cooperatively bind other binding partners in the cell. Both W mutants retained activity but significantly increased the IC50 as compared with the wt iPep62. Molecular modelling analysis of the alanine mutations suggests a wide hydrophobic pocket in the iPep624W2ΔA and a narrow interacting interface in iPep624W1ΔA (FIG. 5c, right). These results highlight the structural selectivity of the peptide and the requirement of the W residues in the EN1 hexamotif for inhibitory activity.

Next, the inventors mapped the minimal EN1-iPep sequence retaining cell growth inhibitory activity in vitro. They generated peptide EN1-iPep682 (FIG. 3c) lacking the less evolutionary conserved five N-terminal residues, and two C-terminal residues of the parent peptide iPep624. The iPep682 was even more effective than the parent full-length iPep624 peptide decreasing the IC50 from 17.5 to 12.5 μM (FIG. 5d). Interestingly, a 13-mer peptide lacking all the N-terminal residues upstream of the hexamotif (iPep697) was less active than the wt EN1-p624 peptide (FIG. 5d), suggesting that the N-terminal arm of the peptide immediately adjacent to the hexamotif (comprising the Proline-Valine-Leucine residues) also provides sequence-specific determinants essential for inhibitory activity.

Lastly, the inventors investigated the capability of the active EN1-iPep (iPep682) to sensitize breast cancer cells to FDA-approved drugs, such as taxol and 5-Fluorouracil (5-FU). SUM149PT cells were particularly resistant to these agents with an IC50 of 7.6 μM for taxol (FIG. 5e) and 610 μM for 5-FU (FIG. 5f) after 48 hours of treatment with these agents. However, cells treated for 48 hours with drug and for 8 hours with low concentration of the iPep682 (500 nM) significantly decreased the IC50 of taxol from 7.6 μM to 49 nM (FIG. 4e), and 5-FU from 610 to 29.47 μM (FIG. 5f). These experiments demonstrate the low doses of iPeps could further sensitize highly resistant breast cancer cells to chemotherapy agents.

EN1-iPeps Capture Intracellular Targets Involved in Control of Translation and Transcriptional Regulation.

To investigate the binding partners of the iPeps in cancer cells, the inventors carried out affinity capture immunoprecipitation experiments using the biotinylated active iPep624 as bait, and the iPep624ΔHEX as negative control. They used total protein extracts from SUM149PT cells to capture endogenous proteins able to bind these peptides in vitro. Elutes were loaded in a 1D-SDS PAGE gel to visualize the enrichment of individual proteins. As shown in FIG. 10, a protein of ~170 KDa was found differentially enriched in the iPep624-elutes relative to iPep624ΔHEX. Protein identification using MALDI-TOF/TOF mass spectrometry revealed a highly significant score for the Glutamyl-Prolyl tRNA synthetase (EPRS), an enzyme that controls transcript-specific mRNA and protein synthesis, particularly of inflammatory proteins and downstream effectors of the amino acid stress pathway. The preferential binding interaction EPRS with iPep624 over control peptide was validated by immunoprecipitation and immunoblotting (FIG. 6b). In addition, overexpression of EN1 cDNA into two different breast cell lines confirmed the interaction of the full length EN1 with the endogenous EPRS inside the cells (FIG. 6c). To ascertain whether some downstream well-known effectors of EPRS were also differentially regulated by the iPeps, we performed real time PCR to detect mRNA levels of COLA1, COLA2, S1004A and DDIT3 (CHOP). The inventors chose these targets since they are transcriptionally modulated by both, siRNA knockdown of EPRS and pharmacological inhibition of EPRS by halofuginone, a februgine derivative of a natural product used to treat cancer, malaria, fibrosis and inflammation recently shown to specifically inhibit EPRS. COLA1 and COLA2 encode collagen proteins highly enriched by the amino acid proline and S1004A is a protein involved in metastasis and fibrosis. These targets have been shown to be differentially downregulated upon inhibition of EPRS. In contrast, the amino acid stress factor DDIT3 is stimulated upon EPRS inhibition. To investigate if these targets were modulated by the EN1 cDNA and the EN1-iPeps, both control and EN1-overexpressing SUM149PT cells where challenged to active iPep624 or inactive iPep624ΔHEX and processed by real-time PCR. As expected, the targets COLA1, COLA2 and S1004A were significantly up-regulated in the EN1-overexpressing cells, and this up-regulation was significantly reverted by addition of active peptide. Conversely, the DDIT3 target was significantly up-regulated in EN1-overexpressing cells by the active iPep over control, in accordance with the specific pharmacological inhibition of EPRS by halofuginone. Interestingly, treatment of SUM149PT cells with halofuginone, iPep624 (FIG. 6d) or an EPRS-specific shRNA (data not shown) induced very potent breast cancer cell death. Co-treatment of SUM149PT cells with iPep624, but not peptide control, sensitized even more the basal-like breast cancer cells to halofuginone (FIG. 6e-f). As expected from EN1 providing resistance to cell death, the combination of iPep624 and halofuginone was more effective in SUM149PT-Control cells than of SUM149PT-EN1 cells (0.041 nM versus 0.49 nM). Overall, these studies indicated that EPRS was bound by iPep624 and full length EN1 in the cancer cells, and suggest that pharmacological inhibition of EPRS using iPeps and in combination with specific inhibitors of EPRS, such as halofuginone could be extremely effective for treatment basal-like breast cancer. Lastly, the inventors examined whether iPep624 could also interact with other $TF_{HD}s$ expressed in basal-like cancers, using immunoprecipitation and western blotting. They observed specific interactions of iPep624, but not control, with PBX family members (notably, PBX1) and with PAX6 (FIG. 11), which are well known partners of Engrailed proteins in other cell systems, particularly in dopaminergic neurons. They also discovered a specific interaction between EN1-iPep and the $TF_{HD}$ Distalless 6 (DLX6), which was found expressed at very high levels in the basal cancers in the inventor's tumor gene expression database (FIG. 12). DLX6 expression has been associated with organ-specific breast cancer metastases. In summary, the inventor's data demonstrates that the EN1-iPeps are able to inhibit the oncogenic function of EN1 in basal cancer cells expressing EN1, by interacting with multiple intracellular partners involved in transcriptional regulation (particularly in the neural system) and suggest that EPRS could be a novel downstream effector of EN1.

Physical and Functional Interaction Between EN1-iPep and EPRS

The physical and functional interaction between EN1-iPep and EPRS is supported by the following findings: (i) IPs using biotinylated EN1-iPeps and flagged EN1 full-length protein as baits following by an anti-EPRS detection demonstrate physical association (FIG. 19, top left). (ii) IF analysis reveal a remarkable perinuclear and nuclear co-localisation of EPRS with the EN1-iPep (FIG. 19, top right). (iii) Molecular dynamics modelling performed on the available structure of HF in complex with EPRS suggest that the EN1-iPep could utilize the hexamotif and the essential W12 to lock the HF into the hydrophobic catalytic pocket of the enzyme, which would prevent the binding of the substrate Pro and stabilize EPRS in an inactive conformation (FIG. 19, bottom). iv) Pulse and chase experiments of SUM149 cells incubated with 3H-Pro and subsequently with EN1-iPep (4 hrs) demonstrates a dramatic decay (~97%) of 3H-Pro (but not 3H-Met) incorporation in the breast cancer cells (FIG. 20, top). v) incorporation of excess of amino acid Pro in the media of SUM149 cells (but not Met) is able to rescue the cell proliferation defect of the EN1-iPep (FIG. 20, bottom). Based on these data, it is believed that EN1-iPep binds the catalytic pocket of EPRS, competing with the binding of Pro, and activating cell death mechanisms.

Combination Treatments

To exploit combinatorial treatments between the EN1-iPeps were combined with a panel of agents reported to have utility in the treatment of TNBCs: EGFR inhibitors (erlotinib, cetuximab), PARP inhibitors (olaparib), paclitaxel, gemcitabine, cisplatin, carboplatin, anthracyclines cyclophosphamide, methotrexate and fluorouracil (5-FU) to rapidly determine the combinations of iPeps and drugs giving rise to the most potent pharmacological synergisms.

Cells were processed by cell-viability assays as described above and toxicity to non-transformed breast epithelial cells was evaluated.

Methods and Methods

Lentivirus Preparation and Transduction of Breast Cell Lines

Plasmids expressing the EN1 cDNA (Genecopoeia, vector EX-T1021-Lv07) or EN1 shRNAs (Open Biosystems, pLKO-EN1) were transfected with Gagpol-, VSVG-, and RSV-REV-coding plasmids in HEK 293T cells using Lipofectamine and Plus Reagent cationic lipids (Invitrogen, Carlsbad, Calif.) and transduction of breast cells was performed as described in Beltran, A. S. et al. *Breast Cancer Res* 13, R94 (2011).

EN1 Expression and Prediction of Relapse-Free Survival (RFS)

To estimate the expression of EN1 across the intrinsic molecular subtypes of breast cancer the inventors calculated the mean expression of EN1 in the entire median centered UNC337 patient database using the subtype calls described in Prat et al. *Breast Cancer Res* 12, R68, (2010). Relapse-free survival was calculated using MERGE-550 database (Beltran, A. S. et al. *PLoS One* 6, (2011)).

Quantitative Real-Time PCR

The qRT-PCR reaction was performed with TaqMan Fast Universal Master Mix (Applied Biosystems, Carlsbad, Calif.) as described in Beltran, A. S. et al. *Breast cancer research: BCR* 13, R94 (2011)).

Immunofluorescence

Tumor tissue sections were obtained from the Tissue Procurement Facility of the UNC Lineberger Comprehensive Cancer Center (Chapel Hill, N.C.). Sections were incubated with antibodies (as described in Beltran, A. S. et al. *Breast cancer research: BCR* 13, R94, (2011)). HUMEC and other cultured cells were incubated at 4° C. overnight with primary antibodies (anti-EN1, anti-VMAT, anti-DAT, anti-TH and anti-Bill tubulin) diluted 1:250 and imaged using Zeiss 510 Meta Inverted Laser Scanning Confocal Microscope.

Peptide and Drug Treatment

All peptides were synthetized at the UNC High-Throughput Peptide Synthesis and Array Facility at UNC. Taxol, Rotenone and Halofuginone (Sigma-Aldrich, St Louis, Mo.) were dissolved in DMSO. A total of $1\times10^8$ or $1\times10^3$ breast cells for peptide and drug treatment respectively, were seeded in 96-well plates. Cells were exposed for 8 hours to the peptide and 48 to 72 hours for drug treatment. The cell viability after peptide/drug treatment was assayed with the Cell Titer Glo (CTG) assay (Promega, Madison, Wis., USA).

Caspase-3 Detection

Detection of apoptosis was performed with a Caspase-3 colorimetric assay (Sigma-Aldrich, St Louis, Mo.) according to the manufacturer's instructions.

Immunoprecipitation/Western Blotting

The iPep624 and iPep624ΔHEX were coupled to a C-terminal biotin and immobilized in streptavidin-coated beads. SUM149PT protein extract (500 μg) was incubated with 20 μL of iPep-beads for 2 hours with tumbling and the beads were washed 3 times with PBS. The supernatant was removed; the beads boiled and loaded on a 12% SDS-PAGE gel. The immunoprecipitations were blotted and probed with antibodies specific for PAX6, DLX6, PBX1, PBX2 and PBX3 (Santa Cruz Biotechnology, Texas, USA). Detection was performed with ECL Detection System (GE Healthcare) and quantitated using Image J v1.46 (ImageJ, NCBI).

Mass Spectrometry/Identification of EPRS

Proteins were eluted from the streptavidin beads coated with biotinylated iPep624 or iPep624ΔHEX, resuspended with SDS PAGE sample buffer and applied to SDS-PAGE (10% acrylamide; FIG. 10). Gels were stained with Coomassie brilliant blue and select bands unique to the EN1 immunoprecipitates were excised, digested with trypsin, and the peptides were extracted and analyzed using a MALDI-TOF/TOF mass spectrometer (AB Sciex 4800 Plus). MS spectra were obtained in reflector positive ion mode and peaks with signal-to-noise ratio above 10 were selected for MS/MS analysis (maximum of 45 MS/MS spectra per spot). All spectra will be searched using GPS Explorer, Version 3.6 (AB Sciex) linked to the Mascot (Matrix Science, Inc.) search engine and a Human IPI database was used.

Gene Expression Microarrays

The stable cell lines SUM149PT-EGFP and SUM149PT-EN1 (N=3) were used for gene expression analyses. RNA was purified, amplified, labeled and hybridized (as described in Hu, Z. et al. *BMC Genomics* 7, 96, (2006)), using Agilent 4X44K oligo microarrays (Agilent Technologies, United States; platform G2514F). The probes/genes were filtered by requiring the lowest normalized intensity values in all samples to be >10. The normalized log 2 ratios (Cy5 sample/Cy3 control) of probes mapping to the same gene were averaged to generate independent expression estimates.

Flag

Flag EN1 is a commercially available cDNA construct (Genecopeia) in which the C-terminal DNA sequence of EN1 is attached in frame with the sequence DYKDDDDK (SEQ ID NO: 17). This "tag" is recognized by a commercially available specific anti-FLAG antibody followed by western blot or immunoprecipitation.

Conclusions

The inventor's results provide evidence for a critical role of the neural-specific $TF_{HD}$ EN1, in controlling inflammatory signals, survival and resistance to cell death in highly aggressive basal-like breast cancers having stem/progenitor cell characteristics. The inventors also provide evidence that novel synthetic peptides or interference peptides (iPeps) comprising the highly conserved EN1-hexamotif sequence involved in protein-protein interactions, induce potent and selective apoptosis in highly resistant basal-like breast cancer cells.

The invention claimed is:

1. A purified and isolated peptide comprising an amino acid sequence selected from:
   a. the amino acid sequence of any one of SEQ ID NOs: 5 to 8; and
   b. KKKRKPL$_2$V$_3$W$_4$PAWV$_8$Y$_9$C$_{10}$TRSDR, (SEQ ID NO: 12), wherein:
   L$_2$ is one of: L, M, or I;
   V$_3$ is one of: V or L;
   W$_4$ is one of: W, Y, or W analog;
   V$_8$ is one of: V or I;
   Y$_9$ is one of: Y or F; and
   C$_{10}$ is one of: C or S
   wherein the peptide (i) prevents the interaction of EN1 with its binding partner in an EN1 expressing cell, and (ii) induces apoptosis of an EN1 or EN2 expressing cell.

2. A pharmaceutical composition comprising a peptide according claim 1.

3. A kit for treating an EN1 or EN2 expressing cancer in a subject, comprising a peptide according to claim 1.

4. A purified and isolated peptide comprising an amino acid sequence selected from the amino acid sequence of any one of SEQ ID NOs: 5 to 8 wherein the peptide induce apoptosis in basal-like breast tumors and other cancers expressing EN1 and EN2 when administered to a patient in need of treatment therefrom.

* * * * *